US012748032B2

(12) United States Patent
Somers et al.

(10) Patent No.: US 12,748,032 B2
(45) Date of Patent: Sep. 29, 2026

(54) PRINTED COIL SENSORS FOR MONITORING FLUID CONDITION

(71) Applicant: Gastops Ltd., Ottawa (CA)

(72) Inventors: Michael Somers, Ottawa (CA); Omar Masaud, Ottawa (CA); Oleg Sosnovski, Ottawa (CA)

(73) Assignee: GASTOPS LTD., Ottawa (CA)

( * ) Notice: Subject to any disclaimer, the term of this patent is extended or adjusted under 35 U.S.C. 154(b) by 0 days.

(21) Appl. No.: 19/375,376

(22) Filed: Oct. 31, 2025

(65) Prior Publication Data

US 2026/0140034 A1 May 21, 2026

Related U.S. Application Data

(60) Provisional application No. 63/722,420, filed on Nov. 19, 2024.

(51) Int. Cl.
*G01N 15/06* (2024.01)
*G01N 33/28* (2006.01)

(52) U.S. Cl.
CPC ..... *G01N 15/0656* (2013.01); *G01N 33/2858* (2013.01)

(58) Field of Classification Search
CPC ..................... G01N 15/0656; G01N 33/2858
USPC ........................................... 73/53.07
See application file for complete search history.

(56) References Cited

U.S. PATENT DOCUMENTS 5,811,664 A 9/1998 Whittington et al.
6,707,043 B2 3/2004 Coates et al.
7,015,484 B2 3/2006 Gillispie et al.
7,391,035 B2 6/2008 Kong et al.
8,155,891 B2 4/2012 Kong et al.
(Continued)

FOREIGN PATENT DOCUMENTS

CN 106568691 B 3/2019
CN 213022751 U * 4/2021
(Continued)

OTHER PUBLICATIONS

Rahmanian, M. et al. "A micropillar array-based microfluidic chip for label-free separation of circulating tumor cells: The best micropillar geometry?", Journal of Advanced Research 47 (2023), pp. 105-121.

(Continued)

*Primary Examiner* — Marrit Eyassu

(57) ABSTRACT

Various methods and systems for monitoring one or more characteristics of a fluid in a mechanical device are disclosed herein. In at least one embodiment, the system includes an optical sensor including an excitation light aperture and an emission light aperture. The excitation light aperture transmits an excitation light to the fluid and the emission light aperture receives an emission light from the fluid. The system may further include an inductive sensor including a printed circuit board including a first field coil trace, a second field coil trace, and a sense coil trace. The methods disclosed include transmitting the excitation light to the fluid; receiving the emission light from the fluid; and operating a processor to obtain one or more fluorescence spectra based on the received emission light; and determine a fluid condition indicator and/or a remaining useful life of the fluid based on the one or more fluorescence spectra.

19 Claims, 55 Drawing Sheets

(56) References Cited

U.S. PATENT DOCUMENTS

| | | | | |
|---|---|---|---|---|
| 9,063,075 | B2 | 6/2015 | Gorritxategi et al. | |
| 9,322,773 | B2 | 4/2016 | Coates et al. | |
| 9,488,617 | B2 | 11/2016 | Jirgal | |
| 10,060,899 | B2 | 8/2018 | Hegazi et al. | |
| 10,254,210 | B2 | 4/2019 | Weiser | |
| 10,330,497 | B1 * | 6/2019 | Moore | H01F 27/2885 |
| 10,974,241 | B2 | 4/2021 | Haeberle et al. | |
| 11,061,010 | B2 | 7/2021 | Wang et al. | |
| 11,300,106 | B2 | 4/2022 | Redding et al. | |
| 11,366,181 | B2 * | 6/2022 | Schulz | G01R 33/0052 |
| 11,674,838 | B2 | 6/2023 | Brewer et al. | |
| 11,709,121 | B2 | 7/2023 | Sipperley et al. | |
| 11,777,376 | B2 * | 10/2023 | Frampton | H02K 29/12 310/68 B |
| 2006/0117839 | A1 | 6/2006 | Fortin et al. | |
| 2016/0282499 | A1 * | 9/2016 | Miyamoto | G01N 27/72 |
| 2017/0269036 | A1 * | 9/2017 | Foord | G01N 27/023 |
| 2018/0017541 | A1 | 1/2018 | Kinard | |
| 2021/0139040 | A1 | 5/2021 | Ganiger et al. | |
| 2021/0231597 | A1 | 7/2021 | Emokpae et al. | |
| 2022/0072456 | A1 | 3/2022 | Pelkey et al. | |
| 2023/0349987 | A1 | 11/2023 | O'Donnell et al. | |

FOREIGN PATENT DOCUMENTS

| | | | |
|---|---|---|---|
| DE | 102010027130 | A1 | 1/2012 |
| EP | 4375639 | A1 | 5/2024 |
| ES | 2455465 | A2 | 4/2024 |

OTHER PUBLICATIONS

International Search Report and Written Opinion issued Jan. 27, 2026 in international patent application No. PCT/CA2025/051447 (6 pages).

* cited by examiner

PRINTED COIL SENSORS FOR MONITORING FLUID CONDITION

CROSS-REFERENCE TO RELATED APPLICATIONS

This application claims priority from U.S. provisional application No. 63/722,420, filed Nov. 19, 2024, the contents of which are hereby incorporated herein by reference.

FIELD

The embodiments described herein generally relate to monitoring fluid using printed coil sensors, and in particular to monitoring machinery and fluid condition for debris, contaminants, additives, and/or other indicators of machinery or machinery fluid health using printed coil sensors.

BACKGROUND

The following is not an admission that anything discussed below is part of the prior art or part of the common general knowledge of a person skilled in the art.

Machinery can include various fluid systems. For example, machinery can include lubrication systems that enable the machinery to operate efficiently and durably. However, over time, machinery components can wear and release debris particles into the lubrication system. Furthermore, seals within the lubrication system can become damaged and/or faulty, which can result in leakage of contaminants, such as fuel and/or water and/or coolant, into the lubrication system. Changes to the composition of a machine's fluid system can significantly impact the machine's performance and risk critical damage to the mechanical components of the machinery.

Fluid monitoring systems can be used to detect fluid health, debris and contaminants within machinery fluid systems. However, some existing solutions are limited to offline applications (e.g., requiring a fluid sample to be analyzed in an external laboratory). Although some existing solutions provide online applications (e.g., the fluid is monitored in-situ), these solutions generally measure macroscopic properties of the fluid. For example, existing solutions generally are unable to distinguish which components within a fluid mixture contributed to various portions of a measured signal. Furthermore, existing solutions, such as sensors, tend to be bulky, expensive and/or heavy. Accordingly, the usefulness of existing solutions is limited.

SUMMARY

This summary is intended to introduce the reader to the more detailed description that follows and not to limit or define any claimed or as yet unclaimed invention. One or more inventions may reside in any combination or sub-combination of the elements or process steps disclosed in any part of this document.

In accordance with at least one aspect, there is provided a system for monitoring one or more properties of a fluid in a mechanical device, the system comprising: a printed circuit board (PCB)-based inductive sensor for detecting one or more metallic particles in the fluid, the PCB-based inductive sensor comprising: at least one printed circuit board (PCB) comprising: one or more layers comprising each of a first field coil trace and a second field coil trace; and one or more layers comprising a sense coil trace, wherein the first field coil trace and the second field coil trace generate a magnetic field when electrically driven and the sense coil trace detects a change in the magnetic field produced by the one or more metallic particles in the fluid.

In accordance with another aspect, there is provided a system for monitoring one or more properties of a fluid in a mechanical device, the system comprising: a printed circuit board (PCB)-based inductive sensor for detecting one or more metallic particles in the fluid, the PCB-based inductive sensor comprising: at least one printed circuit board (PCB) comprising: one or more layers comprising a field coil trace; and one or more layers comprising each of a first sense coil trace and a second sense coil trace, wherein the field coil trace is configured to generate a magnetic field when electrically driven and each of the first sense coil trace and the second sense coil trace are configured to detect a change in the magnetic field produced by the one or more metallic particles in the fluid.

In accordance with a further aspect, there is provided a system for monitoring one or more properties of a fluid in a mechanical device, the system comprising: a printed circuit board (PCB)-based inductive sensor for detecting one or more metallic particles in the fluid, the PCB-based inductive sensor comprising: one or more printed circuit board (PCBs) comprising one or more layers forming at least one field coil trace and at least one sense coil trace, wherein the at least one field coil trace is configured to generate a magnetic field when electrically driven and the at least one sense coil is configured to detect a change in the magnetic field produced by the one or more metallic particles in the fluid.

In accordance with another aspect, there is provided a method of monitoring one or more properties of a fluid in a mechanical device, the method comprising: providing a printed circuit board (PCB)-based inductive sensor for detecting one or more metallic particles in the fluid, the PCB-based inductive sensor comprising: at least one printed circuit board (PCB) comprising: one or more layers comprising each of a first field coil trace and a second field coil trace; and one or more layers comprising a sense coil trace, wherein the first field coil trace and the second field coil trace generate a magnetic field when electrically driven and the sense coil trace detects a change in the magnetic field produced by the one or more metallic particles in the fluid.

In accordance with another aspect, there is provided a method for monitoring one or more properties of a fluid in a mechanical device, the method comprising: providing a printed circuit board (PCB)-based inductive sensor for detecting one or more metallic particles in the fluid, the PCB-based inductive sensor comprising: at least one printed circuit board (PCB) comprising: one or more layers comprising a field coil trace; and one or more layers comprising each of a first sense coil trace and a second sense coil trace, wherein the field coil trace is configured to generate a magnetic field when electrically driven and each of the first sense coil trace and the second sense coil trace are configured to detect a change in the magnetic field produced by the one or more metallic particles in the fluid.

In accordance with a further aspect, there is provided a method for monitoring one or more properties of a fluid in a mechanical device, the method comprising: providing a printed circuit board (PCB)-based inductive sensor for detecting one or more metallic particles in the fluid, the PCB-based inductive sensor comprising: one or more printed circuit board (PCBs) comprising one or more layers forming at least one field coil trace and at least one sense coil trace, wherein the at least one field coil trace is configured to generate a magnetic field when electrically driven and the at least one sense coil is configured to detect a change in the magnetic field produced by the one or more metallic particles in the fluid.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the embodiments described herein and to show more clearly how they may be carried into effect, reference will now be made, by way of example only, to the accompanying drawings which show at least one exemplary embodiment, and in which.

Figure 1:
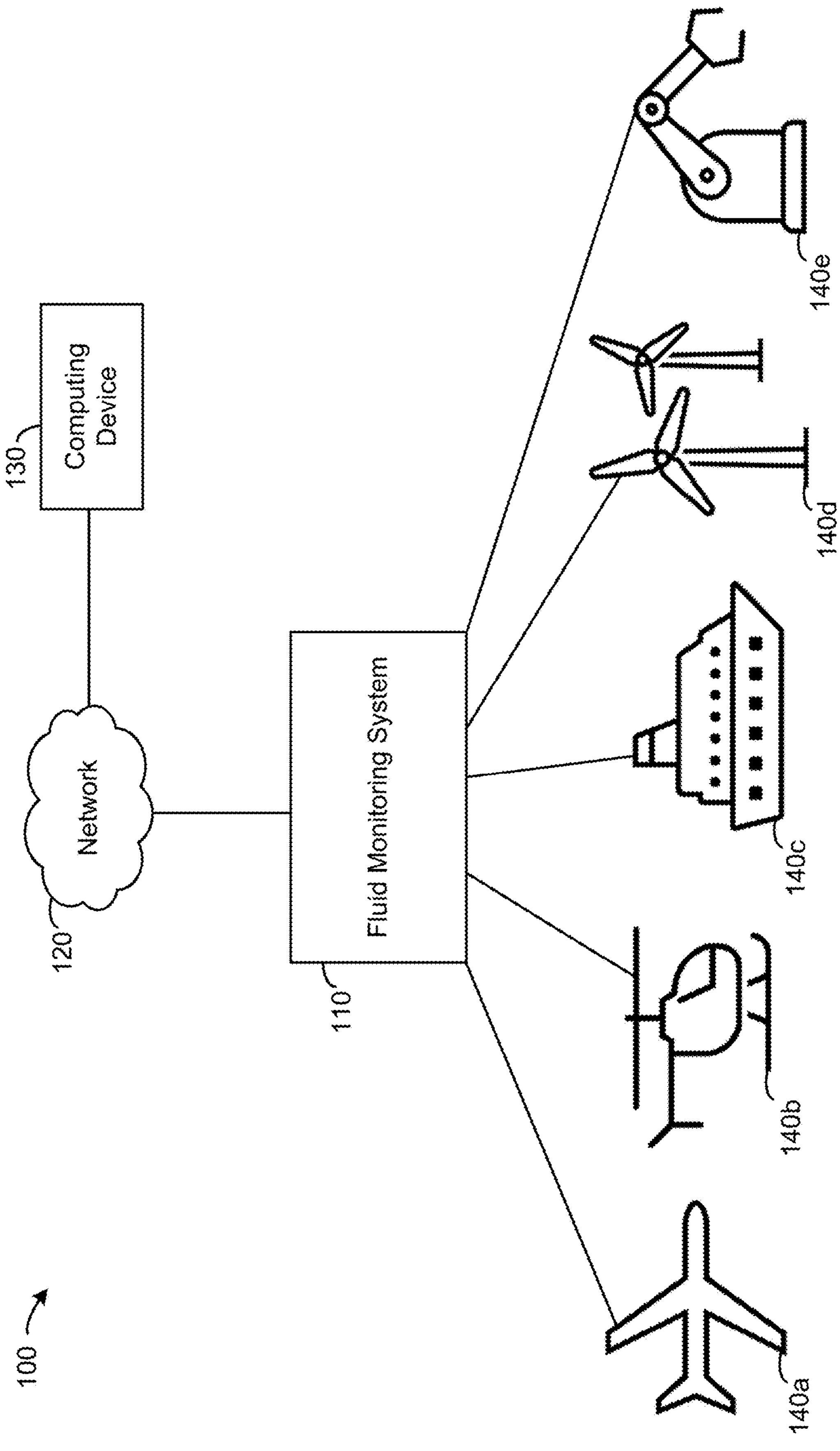
FIG. 1 is a block diagram of an example fluid monitoring system in accordance with an embodiment.

The skilled person in the art will understand that the drawings, described below, are for illustration purposes only. The drawings are not intended to limit the scope of the applicants' teachings in any way. Also, it will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DESCRIPTION OF VARIOUS EMBODIMENTS

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein.

It should be noted that terms of degree such as "substantially", "about" and "approximately" when used herein mean a reasonable amount of deviation of the modified term such that the end result is not significantly changed. These terms of degree should be construed as including a deviation of the modified term if this deviation would not negate the meaning of the term it modifies.

In addition, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

The terms "including," "comprising" and variations thereof mean "including but not limited to," unless expressly specified otherwise. A listing of items does not imply that any or all of the items are mutually exclusive, unless expressly specified otherwise. The terms "a," "an" and "the" mean "one or more," unless expressly specified otherwise.

As used herein and in the claims, two or more elements are said to be "coupled", "connected", "attached", or "fastened" where the parts are joined or operate together either directly or indirectly (i.e., through one or more intermediate parts), so long as a link occurs. As used herein and in the claims, two or more elements are said to be "directly coupled", "directly connected", "directly attached", or "directly fastened" where the element are connected in physical contact with each other. None of the terms "coupled", "connected", "attached", and "fastened" distinguish the manner in which two or more elements are joined together.

The terms "an embodiment," "embodiment," "embodiments," "the embodiment," "the embodiments," "one or more embodiments," "some embodiments," and "one embodiment" mean "one or more (but not all) embodiments of the present invention(s)," unless expressly specified otherwise.

The embodiments of the systems and methods described herein may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication interface. For example and without limitation, the programmable computers may be a server, network appliance, embedded device, computer expansion module, a personal computer, laptop, personal data assistant, cellular telephone, smartphone device, tablet computer, a wireless device or any other computing device capable of being configured to carry out the methods described herein.

In some embodiments, the communication interface may be a network communication interface. In embodiments in which elements are combined, the communication interface may be a software communication interface, such as those for inter-process communication (IPC). In still other embodiments, there may be a combination of communication interfaces implemented as hardware, software, and combination thereof.

Program code may be applied to input data to perform the functions described herein and to generate output information. The output information is applied to one or more output devices, in known fashion.

Each program may be implemented in a high-level procedural or object oriented programming and/or scripting language, or both, to communicate with a computer system. However, the programs may be implemented in assembly or machine language, if desired. In any case, the language may be a compiled or interpreted language. Each such computer program may be stored on a storage media or a device (e.g. ROM, magnetic disk, optical disc) readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloadings, magnetic and electronic storage media, digital and analog signals, and the like. The computer useable instructions may also be in various forms, including compiled and non-compiled code.

Mechanical devices, such as machinery, generally require fluids to operate efficiently and maintain healthy components. Such fluids include lubricating oils, hydraulic fluids, thermal transfer fluids such as coolants, greases, fuel, and other tribological fluids etc. As machinery operates, the machinery components undergo wear and tear over time. Such wear and tear can produce debris and other contaminants that can enter the machinery fluids.

Even small changes to machinery fluid composition can significantly impact machinery performance and increase the risk of damage to mechanical components of the machinery. This is because even small changes to the composition of machinery fluids can cause changes to the fluid viscosity, increase the fluid acidity, increase the risk of corrosion, cause deposition of sludge and/or varnish, and/or other common machinery fluid degradation issues.

The fluid monitoring system disclosed herein can measure properties of the machinery fluid, including characterization of additives and/or contaminants within the machinery fluid.

In some cases, it can be helpful to perform the analysis for diagnostic purposes. For example, when a seal within the machinery is faulty (i.e., leaky) due to damage and/or a defect, machinery fluid, such as lubricant oil, can become contaminated with other fluids from the machinery, such as fuel and/or coolant. In such scenarios, it is helpful to be able to measure the lubricant oil to detect and identify the contaminant fuel and/or coolant, which can further help diagnose a leaky seal or other sources of leaks within the machinery. As another example, as machinery operates over time, components of the machinery can deteriorate and release debris, such as metallic particles, in the machinery fluid system. The diagnostics can be qualitative (e.g., fuel contamination present in lubricant oil) and/or quantitative (e.g., fuel contamination is 1.1 wt %).

In other cases, it can be helpful to perform the analysis for prognostic purposes. For example, the fluid monitoring system can determine, based on the measurements of the machinery fluid over time, when the debris and/or contaminants within the fuel will reach a critical level that would likely lead to damage and/or critical failure of the machinery. This can include determining the remaining useful lifetime of a machinery fluid before it requires replacement or treatment. A maintenance recommendation could be determined based on these prognostics, such as a recommendation to "drain and replace the machinery lubricant oil within the next 45 hours", for example. Such prognostics and maintenance recommendations could reduce the costs and/or labor requirements for operating and maintaining the machinery. The prognostics can be quantitative (e.g., based on a current fuel contamination of 1 wt %, and a linear rate of fuel contamination increase of 0.25 wt % per day, there will be 10 days before a critical concentration of 3.5 wt % of fuel contamination in the lubricant oil is reached).

In some cases, it can be useful to screen a fluid before introducing it into machinery. For example, marine bunker fuel can often be contaminated. Accordingly, it can be useful to determine the quality of the fuel received from a supplier before adding it to the machinery.

It can be helpful to analyze the machinery fluid composition based on measurements of certain machinery fluid properties. Several conventional solutions for such analysis exist. Generally, these solutions are performed in an offline manner. That is, a fluid sample is obtained from machinery and is analyzed in an external laboratory off-site. Fluid samples are commonly analyzed on a monthly or quarterly basis. Such approaches are sufficient for slow contamination events or slow deterioration of the machinery fluid. However, such approaches are insufficient for contamination or deterioration that occur at faster rates than fluid samples are obtained and analyzed. Furthermore, offline monitoring requires additional time and labor to collect fluid samples, transport the fluid samples to a laboratory, and analyze the fluid samples at the laboratory.

Accordingly, it can be helpful to analyze the machinery fluid composition in an online manner. That is, obtaining measurements of the machinery fluid properties while the machinery fluid is still within the machinery (i.e., online measurements do not require a fluid sample to be removed from the machinery). This further provides the possibility of automated analysis, such that measurements and analysis can be performed on the machinery fluid in real-time or near real-time to obtain a current health status of the machinery fluid.

Existing (online) solutions generally use electrical methodologies. However, electrical methods generally only measure macroscopic properties of the machinery fluid. That is, various chemical species within the machinery fluid contribute to the electrical measurements that are obtained, and distinguishing the relative contributions from the different chemical species can be challenging.

Some existing solutions use absorptive approaches using wavelengths of light in the infrared, near infrared, visible, or ultraviolet (UV) ranges, with infrared and near infrared ranges being the most commonly employed. Many approaches using light in the visible range are not reliable since many chemical species within the machinery fluid can contribute to visible light absorption within the machinery fluid. Some existing solutions use Raman spectroscopy, which typically requires a high-powered laser source and specialty detection equipment. Another commonly used method is Fourier Transform Infrared (FTIR) spectroscopy which also requires specialty interferometric detection equipment.

Embodiments described herein provide systems, methods and devices for monitoring conditions and/or physiochemical properties of fluid, such as machinery fluid. The systems described herein can include one or more probes having one or more sensors. For example, the one or more probes can include one or more of an optical sensor, an electrical properties sensor, and inductive sensor, and a temperature sensor. In some embodiments, the one or more sensors are in physical contact with the fluid to be monitored. In various embodiments, the systems described herein are implemented in an online manner (i.e., the fluid being monitored is in-situ). In alternative embodiments, the systems described herein can be implemented in an offline manner (i.e., the fluid being monitored is ex-situ).

As discussed above, in various embodiments, the systems, methods and devices disclosed herein detect constituents, debris and/or contaminants within the fluid being monitored. For example, in various embodiments, the systems, methods and devices described herein can detect one or more of water contamination, fuel contamination, additive concentrations (e.g., antioxidants or fluorescent additives), fluorescent antioxidant oxidation products, soot, and/or metal debris. In some embodiments, the systems, methods and devices can further detect additive depletion (e.g., antioxidant depletion) in fuels and degradation of coolants.

In some embodiments, the systems can classify the fluid type and/or quality. For example, such classification can be used to ensure that the correct fluid is being added to a particular machine.

Referring now to FIG. 1, shown therein is a block diagram 100 of a fluid monitoring system 110. As shown in the example of FIG. 1, the fluid monitoring system 110 is connected to a computing device 130 via a network 120.

As further shown in the example of FIG. 1, the fluid monitoring system 110 can monitor fluid conditions in a plurality of applications. For example, the fluid monitoring system 110 monitors fluid conditions (e.g., physiochemical properties of lubricating fluid) in aircraft applications 140*a*, rotorcraft applications 140*b*, watercraft applications 140*c*, wind turbine applications 140*d*, and/or other machinery applications 140*e*. Applications 140*a-e* are provided as examples only, and it should be understood that fluid monitoring system 110 can monitor fluid conditions in other applications.

In some embodiments, fluid monitoring system 110 monitors fluid in an online manner. That is, the fluid monitoring system 110 monitors fluid in-situ, while the machinery in which the monitored fluid is located is in normal operation. In alternative embodiments, fluid monitoring system 110 monitors fluid in an offline manner. That is, the fluid monitoring system 110 monitors fluid ex-situ by analyzing a fluid sample that is obtained from the machinery.

The computing device 130 may be any networked device operable to connect to the network 120. A networked device is a device capable of communicating with other devices through a network such as the network 120. A networked device may couple to the network 120 through a wired or wireless connection. These computing devices 130 may include at least a processor and memory, and may be an electronic tablet device, a personal computer, workstation, server, portable computer, mobile device, personal digital assistant, laptop, smart phone, WAP phone, an interactive television, video display terminals, gaming consoles, and portable electronic devices or any combination of these.

Although only one computing device 130 is shown in FIG. 1, it will be understood that more than one computing device 130 can communicate with the fluid monitoring system 110 at any one time. In some embodiments, a connection request initiated from the computing device 130 may be initiated from a web browser and directed at the browser-based communications application on the fluid monitoring system 110. In some embodiments, computing device 130 includes separate computing devices for different users interacting with the fluid monitoring system 110.

Although not shown in FIG. 1, in some embodiments, fluid monitoring system 110 may also include a computing device. In some embodiments, system 110 comprises a computing device that may be a microprocessor, laptop, portable computer, small form-factor personal computer, workstation, server, portable computer, mobile device, personal digital assistant, laptop, smart phone, WAP phone, an interactive television, video display terminals, gaming consoles, and portable electronic devices or any combination of these.

The network 120 may be any network capable of carrying data, including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these, capable of interfacing with, and enabling communication between, the fluid monitoring system 110 and the computing device 130. In various embodiments, the network 120 includes on-vehicle or industrial networks, such as, for example, including but not limited to Aeronautical Radio, Incorporated (ARINC) standard (a communication protocol widely used in avionics or aerospace), Controller Area Network (CAN) bus (a communication protocol widely used in automotive, marine and industrial systems), or Modbus (a communication protocol widely used in marine or industrial systems).

Figure 2:
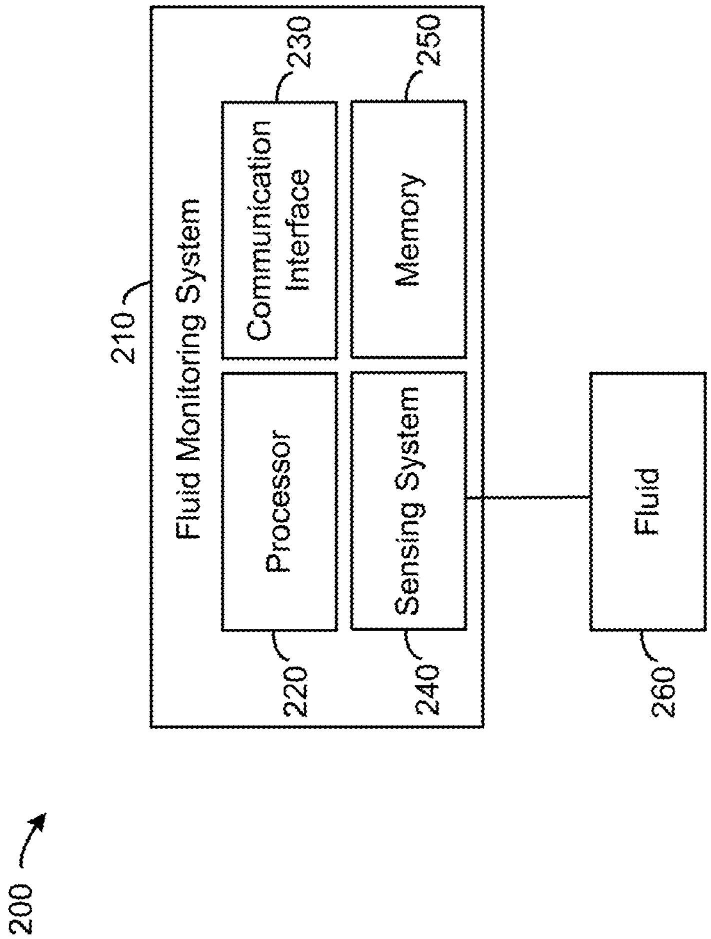
FIG. 2 is a block diagram of another example of a fluid monitoring system in accordance with an embodiment.

Referring now to FIG. 2, shown therein is a block diagram 200 of fluid monitoring system 210 for monitoring properties of the fluid 260. As shown in the example in FIG. 2, fluid monitoring system 210 includes a processor 220, a communication interface 230, a sensing system 240, and a memory 250.

In some other embodiments, the fluid monitoring system 210 only includes a sensing system 240 and a communication interface 230. In such embodiments, some other components, such as, the processor 220 and the memory 250 are located remotely from the fluid monitoring system 210. In some further embodiments, the fluid monitoring system 210 includes a sensing system 240, a communication interface 230 and a memory 250, whereas the processor 220 is located remotely from the fluid monitoring system 210.

The processor 220 may be any suitable processors, controllers, digital signal processors, or application specific circuitry that can provide sufficient processing power depending on the configuration, purposes and requirements of the fluid monitoring system 210. In some embodiments, the processor 220 can include more than one processor with each processor 220 being configured to perform different dedicated tasks. In some cases, the processor 220 may include an on-site processor and an external processor working in collaboration to carry out the functionalities of the processor 220.

The processor 220 can be configured to control the operation of the various components of the fluid monitoring system 210. For example, the processor 220 can control operation of the sensing system 240. The processor 220 can also be configured to control communications between the fluid monitoring system 210 and external devices, such as the computing device 130.

In some examples, the processor 220 may be configured to process measurement data received from the sensing system 240. For example, the measurement data may correspond to unprocessed sensor measurements from one or more sensors included in the sensing system 240 and the processor 220 may be configured to receive and process this data to determine one or more properties of the fluid 260. Alternately or in addition, processor 220 may be configured to calibrate at least a portion of the measurement data based on one or more calibration parameters for the sensing system 240 and/or based on at least another portion of the measurement data. For example, calibration parameters may be stored in memory 250. Processor 220 may use the stored calibration parameters to adjust/calibrate the measurement data based on the specific parameters of the given sensing system 240.

Alternately, processor 220 may not perform any processing on the received measurement data. For example, processor 220 may store and/or transmit the measurement data without any processing and/or adjustments.

In some examples, processor 220 may be configured to store the measurement data received from the sensing system 240 in memory 250. Processor 220 may store the measurement data in memory 250 in an unprocessed form. Alternately or in addition, processor 220 may be configured to store processed measurement data and/or determined fluid properties in memory 250.

In some examples, processor 220 may be configured to transmit the measurement data (whether raw, processed or partially processed) to an external analysis system and/or device, such as computing device 130. Processor 220 may transmit the measurement data to external devices using communication interface 230. Alternately, the processor 220 may simply receive the measurement data and provide the data to the communication interface 230 in an unprocessed form (i.e. without performing any processing on the received measurement data). Alternately or in addition, processor 220 may be configured to provide partially processed measurement data and/or determined fluid properties data to an external analysis system and/or device using communication interface 230.

The communication interface 230 may be any interface that enables the fluid monitoring system 210 to communicate with other devices and systems, such as, but not limited to, a computing device 130 using a network such as the network 120. In some embodiments, the communication interface 230 can include at least one of a serial port, a parallel port or a USB port. The communication interface 230 may also include at least one of an Internet, Local Area Network (LAN), Ethernet, Firewire, modem or digital subscriber line connection. In some embodiments, the communication interface 230 may be a wireless communication interface, which can transmit various data to other devices or systems via Bluetooth, WiFi, or other suitable wireless communication standard. In other embodiments, the communication interface 230 can support industrial and automotive communication protocols, such as, for example, Modbus (e.g., in industrial and marine applications), CAN bus or J1939 (e.g., in automotive and heavy-duty vehicle), and AIRINC (e.g., in aerospace avionics). In some cases, the communication interface 230 may be omitted. For example, where the memory 250 is a removable data storage device, the communication interface 230 may not be needed.

The sensing system 240 includes at least one component that is configured to make physical contact with, or near physical contact with, the fluid 260. The sensing system 240 can include one or more sensors to measure one or more physicochemical properties and/or conditions of fluid 260. The sensing system 240 can be in communication with the processor 220 via a wired and/or wireless connection. For example, the sensing system 240 can be configured to transmit measurement data to the processor 220. Further detail about the sensing system 240 will be provided with reference to FIGS. 3A-D.

The memory 250 may store various data, such as, but not limited to data measured by the sensing system 240. In some cases, the memory 250 may store calibration data specific to the fluid monitoring system 210 that can be used to calibrate the data measured by the sensing system 240. The memory 250 may also store processed data determined by the processor 220. The memory 250 can include RAM, ROM, one or more hard drives, one or more flash drives or some other suitable data storage elements such as disk drives, etc. In some cases, the memory 250 may be removable from the fluid monitoring system 250.

The fluid 260 to be monitored can include any machinery fluid. For example, the fluid 260 can include oil (such as lubricating oil), coolant (such as water or water/glycol mixtures), hydraulic fluid, thermal transfer fluid, fuel, tribological fluid, and/or any other fluid used in machinery and/or mechanical devices. In some embodiments, the fluid 260 includes semi-solid lubricant, such as grease.

In some embodiments, fluid 260 includes one or more contaminants. Some fluids are deemed contaminants when present in machinery fluid, such as lubricating oil. For example, fuel, coolant, and/or water may be considered contaminants when present within machinery fluid. Contaminants may not be present in fluid 260 in substantial quantities immediately after fluid 260 has been changed (e.g., after an oil change when fluid 260 is a lubricating oil) and the concentration of contaminants present in fluid 260 may increase over time. In some embodiments, even small amounts of contaminants relative to the combined mass of fluid 260 (e.g., less than 5% by weight) can negatively impact performance of the machine in which fluid 260 is located.

In various embodiments, the fluid monitoring system 210 is embodied as a probe. The probe is a device or instrument designed to penetrate or interact with a fluid medium, such as fluid 260, to monitor its properties.

Figure 3A:
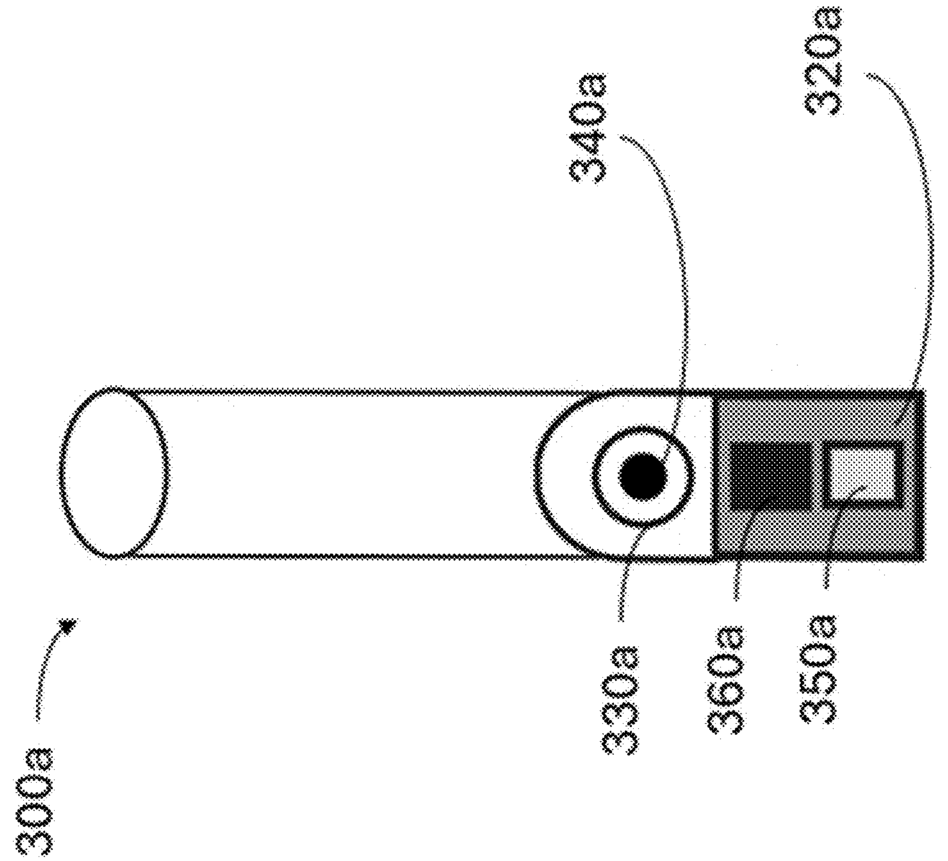
FIG. 3A is an example probe of the example fluid monitoring system shown in FIG. 2 in accordance with an embodiment.

Referring to FIG. 3A, shown therein is an example probe 300*a*. In the example shown in FIG. 3A, probe 300*a* includes an inductive sensor 320*a*, a window 330*a*, an optical sensing system 340*a*, an electrical properties sensor 350*a* and a temperature sensor 360*a*.

As shown in the example in FIG. 3A, at least a portion of the probe 300*a* has a generally cylindrical shape. In alternative embodiments, at least a portion of the probe 300*a* has another shape, such as a generally polygonal shape. In some embodiments, the general width of the probe 300*a* is between approximately 1 millimeter to 1000 millimeters.

The inductive sensor 320*a* can include any suitable inductive sensor. The inductive sensor 320*a* is used to monitor debris within a fluid. Further detail about the inductive sensor 320*a* is provided with reference to FIGS. 8 and 10A-24B.

The window 330*a* can allow optical sensing system 340*a* to operate without directly contacting the fluid to be monitored, such as fluid 260. That is, the window 330*a* protects the optical sensing system 340*a* from direct exposure to contaminants that may be present in fluid 260, such as solids that could deposit on or near optical sensing system 340*a* (e.g., soot, varnish, and/or sludge) thereby impacting the efficacy of optical sensing system 340*a*.

The window 330*a* can include an optically transparent material that transmits light in the ultraviolet and/or visible wavelength ranges. For example, the window 330*a* can transmit excitation light from optical sensing system 340*a* to fluid, such as fluid 260, and/or emitted light from fluid 260 to be received by optical sensing system 340*a*. In some embodiments, the window 330*a* is made of sapphire. In some embodiments, the window 330*a* is made of quartz. In some embodiments, the window 330*a* includes an optically transparent material that transmits light in the infrared wavelength range.

The electrical properties sensor 350*a* can include any suitable electrical properties sensor. The electrical properties sensor 350*a* is used to monitor contaminants, such as water and/or soot, within a fluid. Further detail about the electrical properties sensor 350*a* is provided with reference to FIG. 7A.

The temperature sensor 360*a* can include any suitable temperature sensor. The temperature sensor 360*a* can be used to monitor temperature of a fluid. Further detail about the temperature sensor 360*a* is provided with reference to FIGS. 9A-C. In the example shown in FIG. 3A, the entirety of window 330*a* includes an optically transparent material. In alternative embodiments, a portion of window 330*a* includes an optically transparent material while another portion of window 330*a* includes a different material.

In some embodiments, the surface of window 330*a* is angled at approximately 45 degrees. In some embodiments, the surface of window 330*a* is at an angle between 0 degrees and 90 degrees with respect to the longitudinal axis of the probe 300*a*. For example, in some embodiments, the window 330*a* is at an angle between 10 and 80 degrees, 20 and 70 degrees, 30 and 60 degrees, or 40 and 50 degrees.

In some embodiments, the window 330*a* is omitted. In such embodiments, optical sensing system 340*a* is configured to directly contact fluid, such as fluid 260.

The optical sensing system 340*a* can include any suitable optical sensing system for monitoring contaminants within a fluid. The optical sensing system 340*a* can include one or more optical elements such as spectrometer, focusing optics, fiber optics, and/or light sources. In some embodiments, the optical sensing system 340*a* is fluorescence-based system. For example, the optical sensing system 340*a* can operate based on fluorescence spectrometry techniques. In some embodiments, the optical sensing system 340*a* is non-fluorescence based. For example, the optical sensing system 340*a* can operate based on techniques such as optical absorbance (Near Infrared or Infrared), Raman spectroscopy and variants thereof, hyperspectral imaging, surface plasmon resonance, and/or other non-linear optical techniques. Further detail about the optical sensing system 340*a* is provided with reference to FIGS. 10-20.

Figure 3B:
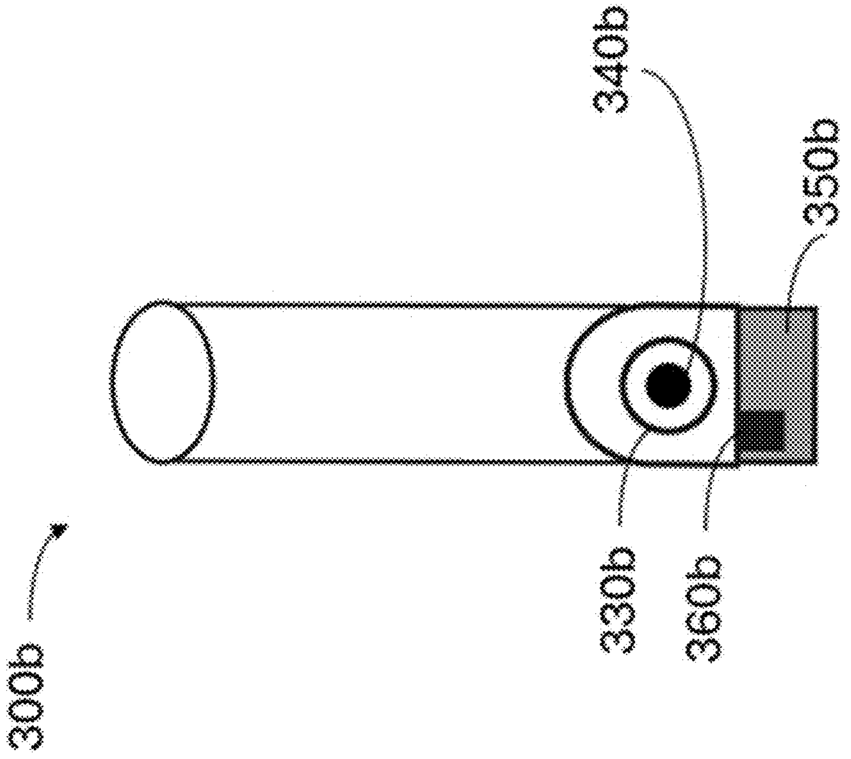
FIG. 3B is another example probe of the example fluid monitoring system shown in FIG. 2 in accordance with an embodiment.

Referring to FIG. 3B, shown therein is an example probe 300*b*. In the example shown in FIG. 3B, probe 300*b* includes a window 330*b*, an optical sensing system 340*b*, an electrical properties sensor 350*b*, and a temperature sensor 360*b*.

The window 330*b* is analogous to window 330*a*. The optical sensing system 340*b* is analogous to optical sensing system 340*a*. The electrical properties sensor 350*b* is analogous to electrical properties sensor 350*a*. The temperature sensor 360*b* is analogous to temperature sensor 360*a*.

Figure 3C:
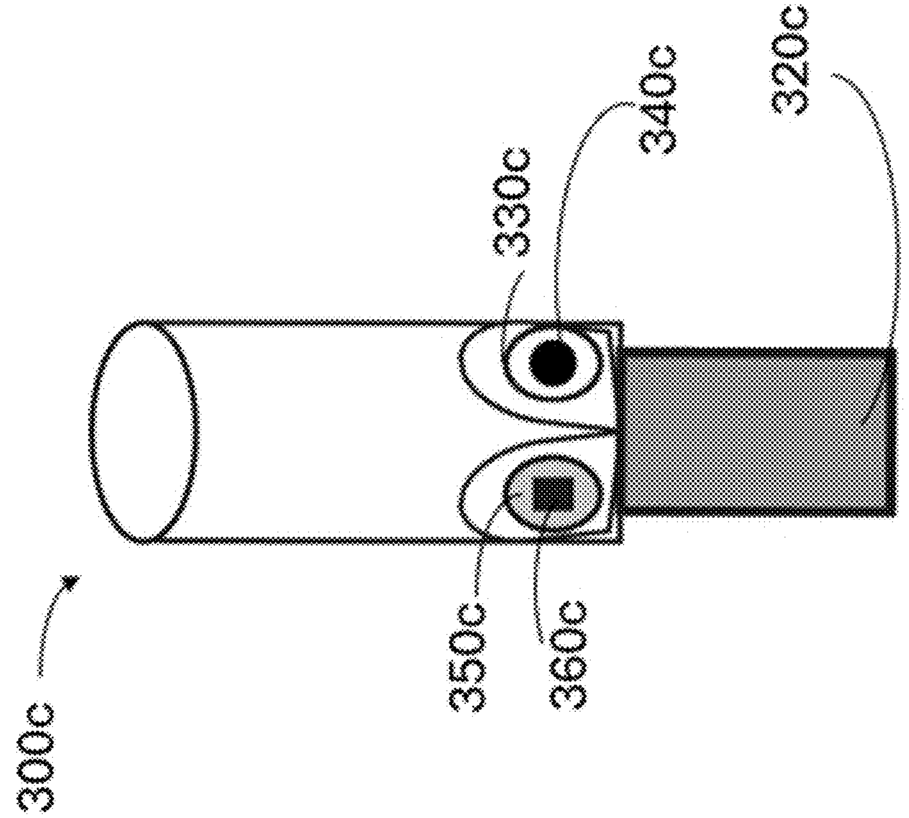
FIG. 3C is another example probe of the example fluid monitoring system shown in FIG. 2 in accordance with an embodiment.

Referring to FIG. 3C, shown therein is an example probe 300*c*. In the example shown in FIG. 3C, probe 300*c* includes an inductive sensor 320*c*, a window 330*c*, an optical sensing system 340*c*, an electrical properties sensor 350*c*, and a temperature sensor 360*c*.

The inductive sensor 320*c* is analogous to inductive sensor 320*a*. The optical sensing system 340*c* is analogous to optical sensing system 340*a-b*. As shown in the example of FIG. 3C, probe 300*c* includes a window 330*c* adjacent to optical sensing system 340*c*. In alternative embodiments, probe 300*c* may not include window 330*c*.

The electrical properties capacitive sensor 350*c* is analogous to electrical properties sensor 350*a-b*. The temperature sensor 360*c* is analogous to temperature sensor 360*a-b*.

Figure 3D:
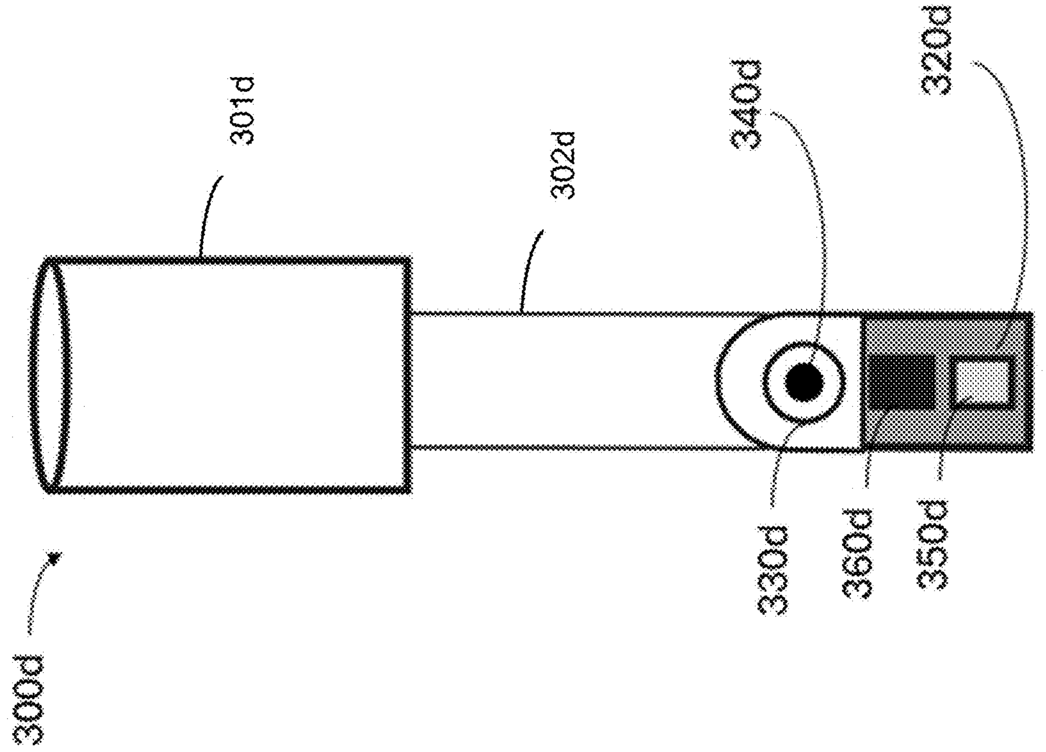
FIG. 3D is another example probe of the example fluid monitoring system shown in FIG. 2 in accordance with an embodiment.

Referring to FIG. 3D, shown therein is an example probe 300*d*. In the example shown in FIG. 3D, probe 300*d* includes an inductive sensor 320*d*, a window 330*d*, an optical sensing system 340*d*, an electrical properties sensor 350*d* and a temperature sensor 360*d*.

The inductive sensor 320*d* is analogous to inductive sensors 320*a* and 320*c*. The window 330*d* is analogous to windows 330*a-c*. The optical sensing system 340*d* is analogous to optical sensing system 340*a-c*. The electrical properties sensor 350*d* is analogous to electrical properties sensor 350*a-c*. The temperature sensor 360*d* is analogous to temperature sensor 360*a-c*.

As shown in the example in FIG. 3D, probe 300*d* can have two concentric portions 301*d* and 302*d*, which are shown as generally cylindrical portions in probe 300*d*. In alternative embodiments, at least a portion of the probe 300*d* has another shape, such as a generally polygonal shape. In some embodiments, the ratio of the width of the first concentric portion 301*d* to the width of the second concentric portion 302*d* is in the range of 1000 to 1.01.

Figure 4A:
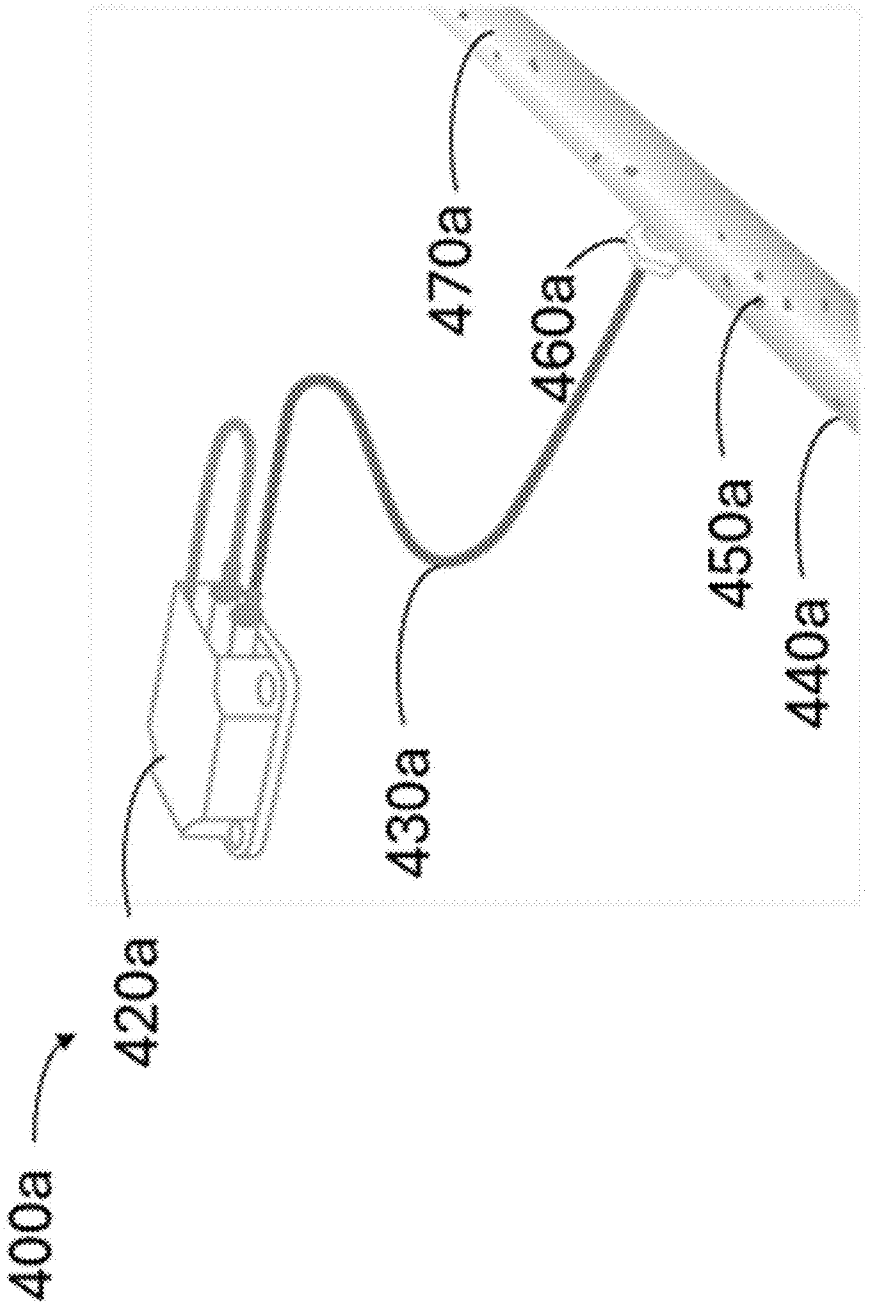
FIG. 4A is an illustration of an example fluid monitoring system in accordance with an embodiment.

Referring to FIG. 4A, shown therein is an example illustration 400*a* of a fluid monitoring system, such as fluid monitoring system 210, in an online application. As shown in the example in FIG. 4A, the fluid monitoring system includes one probe 460*a*. Probe 460*a* is installed in-line of a pipe 440*a* carrying fluid 470*a*. Fluid 470*a* is shown to have particulates 450*a*, which can be detected by the fluid monitoring system. Cable 430*a* connects the probe 460*a* to a processing unit 420*a*.

The processing unit 420*a* can include, for example, a processor such as processor 220, a memory such as memory 250, and/or a communication interface such as communication interface 230. The processing unit 420*a* can further include other components for sending and/or receiving data and/or signals to and/or from probe 460*a*.

Cable 430*a* can include a fiber optic cable and/or electronic cables to transmit data and/or signals to and/or from the probe 460*a*. In some embodiments, cable 430*a* includes a fiber optic cable having one or more fiber optic strands. In some embodiments, the fiber optic cable has 1 to 20 fiber optic strands. In some embodiments, the fiber optic cable has 2 to 5 fiber optic strands. Although FIG. 4A only shows one cable 430*a*, it should be understood that other example embodiments can include more than one cable 430*a*.

Figure 4B:
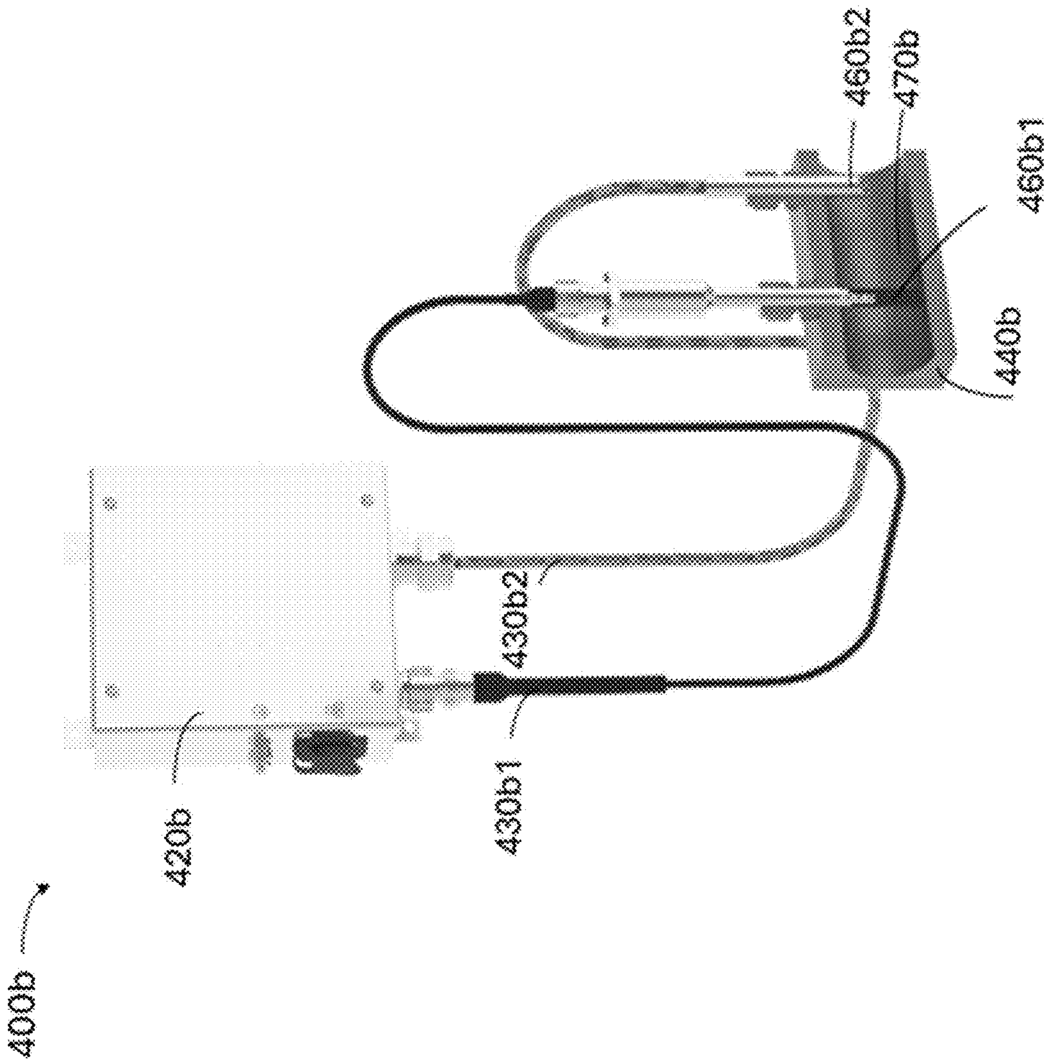
FIG. 4B is an illustration of another example fluid monitoring system in accordance with an embodiment.

Referring to FIG. 4B, shown therein is an example illustration 400*b* of a fluid monitoring system, such as fluid monitoring system 210, in an on-line application. As shown in the example in FIG. 4B, the fluid monitoring system includes two probes. Probes 460*b*1 and 460*b*2 are installed on-line of pipe 440*b* carrying fluid 470*b*. Each of probes 460*b*1 and 460*b*2 can include one or more sensors. For example, probe 460*b*1 can include an inductive sensor, and probe 460*b*2 can include one or more of an electrical properties sensor, a temperature sensor, and an optical sensing system. Cable 430*b*1 connects probe 460*b*1 to the processing unit 420*b*. Cable 430*b*2 connects probe 460*b*2 to the processing unit 420*b*. Each of cables 430*b*1 and 430*b*2 is analogous to cable 430*a*.

Although not shown in the example of FIG. 4B, in some embodiments the fluid monitoring system comprises more than two probes, wherein each probe can include one or more sensors and/or sensing systems.

Figure 5:
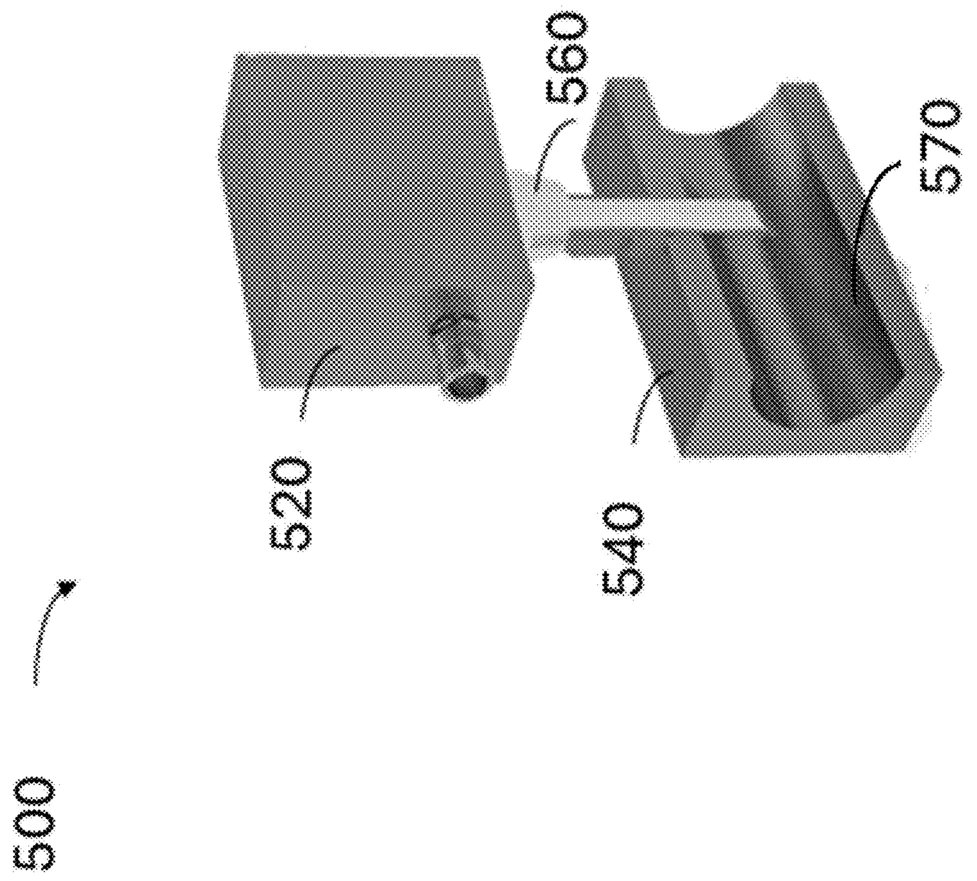
FIG. 5 is an illustration of another example fluid monitoring system in accordance with an embodiment.

Referring to FIG. 5, shown therein is an example illustration 500 of a fluid monitoring system, such as fluid monitoring system 210, in an online application. As shown in the example in FIG. 5, probe 560 is installed on-line of pipe 540 carrying fluid 570. Probe 560 can include one or more sensors. As shown in FIG. 5, the probe 560 is connected directly to the processing unit 520 without the use of cables, such as cable 430*a*.

In some embodiments, multiple probes, such as probes 460*a* (FIG. 4A), 460*b*1, 460*b*2 (FIG. 4B), or 560 (FIG. 5), are used at different locations throughout the pipe to capture measurement data from the fluid at those different locations. This may provide the advantage of more accurately detecting the properties of the fluid in the pipe.

Figure 6A:
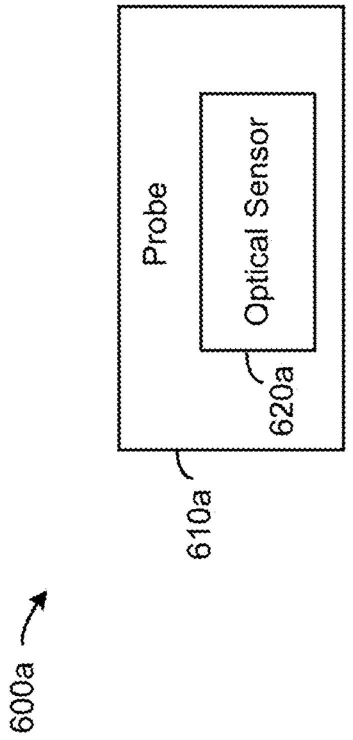
FIG. 6A is a block diagram of an example probe of the fluid monitoring system of FIG. 2 in accordance with an embodiment.

Referring to FIG. 6A, shown therein is a block diagram 600*a* of an example probe 610*a*. As shown in FIG. 6A, the probe 610*a* can include an optical sensor 620*a*. The optical sensor 620*a* is analogous to optical sensors of optical sensing systems 340*a-d*.

Figure 6B:
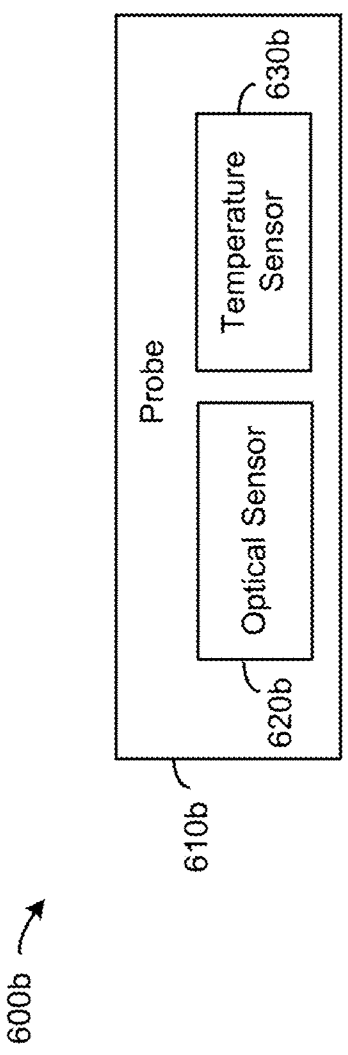
FIG. 6B is a block diagram of another example probe of the fluid monitoring system of FIG. 2 in accordance with an embodiment.

Referring to FIG. 6B, shown therein is a block diagram 600*b* of an example probe 610*b*. As shown in FIG. 6B, probe 610*b* can include an optical sensor 620*b* and a temperature sensor 630*b*. Optical sensor 620*b* is analogous to optical sensor 620*a*. Temperature sensor 630*b* is analogous to temperature sensor 360*c*.

Figure 6C:
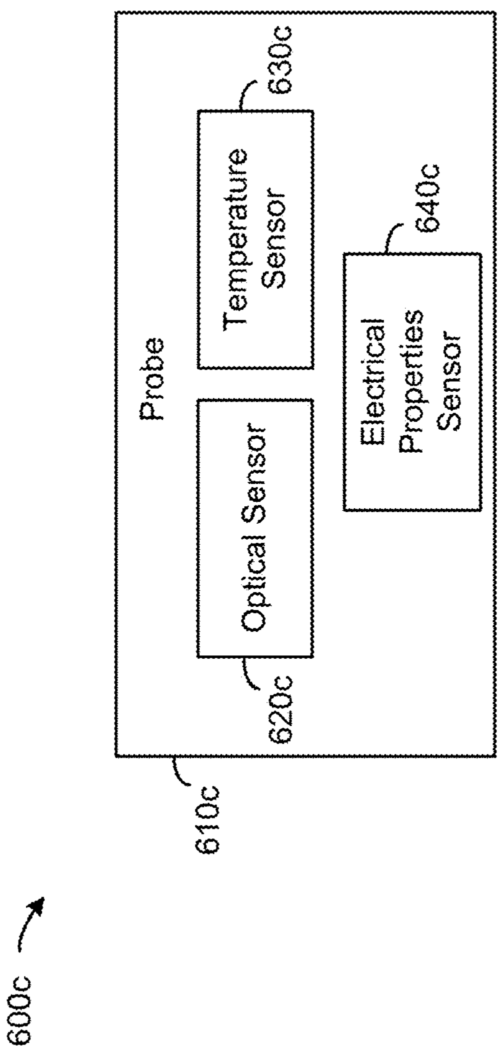
FIG. 6C is a block diagram of another example probe of the fluid monitoring system of FIG. 2 in accordance with an embodiment.

Referring to FIG. 6C, shown therein is a block diagram 600*c* of an example probe 610*c*. As shown in FIG. 6C, probe 610*c* can include an optical sensor 620*c*, a temperature sensor 630*c*, and an electrical properties sensor 640*c*. Optical sensor 620*c* is analogous to optical sensors 620*a-b*. Temperature sensor 630*c* is analogous to temperature sensor 630*b*. Electrical properties sensor 640*c* is analogous to electrical properties sensor 350*b*.

Figure 6D:
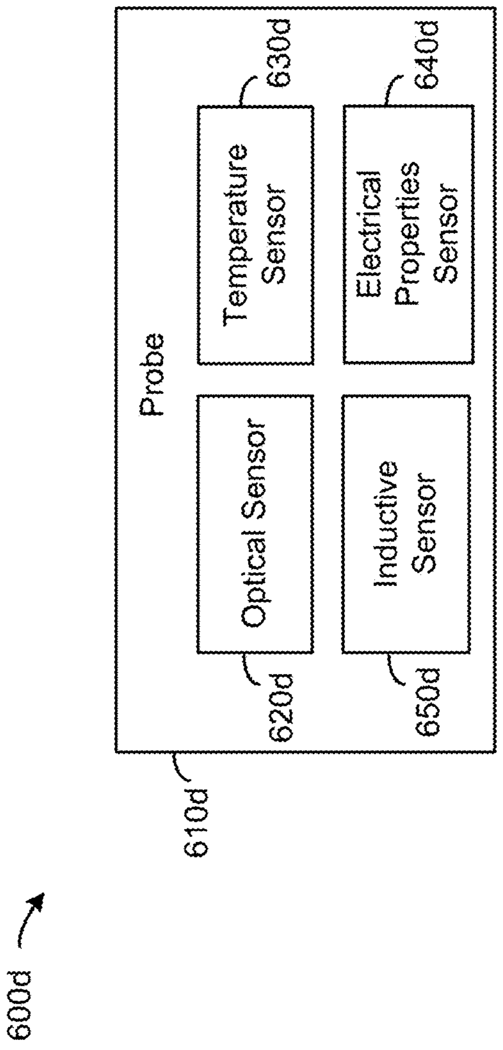
FIG. 6D is a block diagram of another example probe of the fluid monitoring system of FIG. 2 in accordance with an embodiment.

Referring to FIG. 6D, shown therein is a block diagram 600*d* of an example probe 610*d*. As shown in FIG. 6D, probe 610*d* can include an optical sensor 620*d*, a temperature sensor 630*d*, an electrical properties sensor 640*d*, and an inductive sensor 650*d*. Optical sensor 620*d* is analogous to optical sensors 620*a-c*. Temperature sensor 630*d* is analogous to temperature sensors 630*b-c*. Electrical properties sensor 640*d* is analogous to electrical properties sensor 640*c*. Inductive sensor 650*d* is analogous to inductive sensors 320*a*, and 320*c-d*.

Figure 6E:
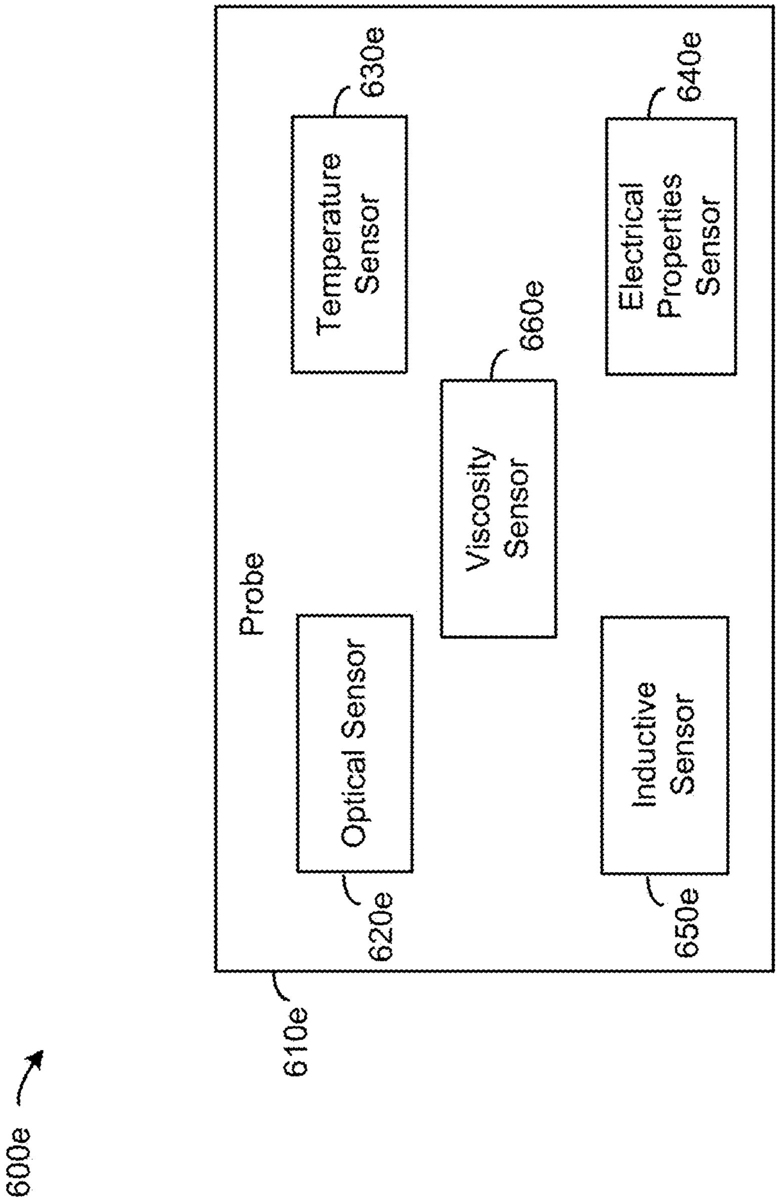
FIG. 6E is a block diagram of another example probe of the fluid monitoring system of FIG. 2 in accordance with an embodiment.

Reference is next made to FIG. 6E, shown therein a block diagram 600*e* of an example probe 610*e*. Probe 610*e* includes an optical sensor 620*e*, a temperature sensor 630*e*, an electrical properties sensor 640*e*, an inductive sensor 650*e*, and a viscosity sensor 660*e*. Optical sensor 620*e* is configured to measure optical properties of the fluid, such as fluorescence. Temperature sensor 630*e* monitors the fluid temperature. Electrical properties sensor 640*e* measures dielectric constant, conductivity, or other electrical characteristics. Inductive sensor 650*e* detects metallic or ferrous debris particles. Viscosity sensor 660*e* measures fluid viscosity in real-time, providing additional diagnostic information about fluid condition. In some embodiments, viscosity sensor 660*e* is a tuning fork viscosity sensor, such as, for example, a quartz tuning fork sensor. In some other embodiments, a density sensor may be included in addition to or alternative to the viscosity sensor to monitor fluid density.

The data from all sensors 620*e*-660*e* can be collected and transmitted to a processing unit for diagnostic and prognostic analysis. In some embodiments, sensor readings are analyzed independently or in combination to detect contaminants, degradation, or abnormal fluid conditions. Probe 610*e* may be integrated into a fluid monitoring system similar to probes 610*a-d*.

Figure 7A:
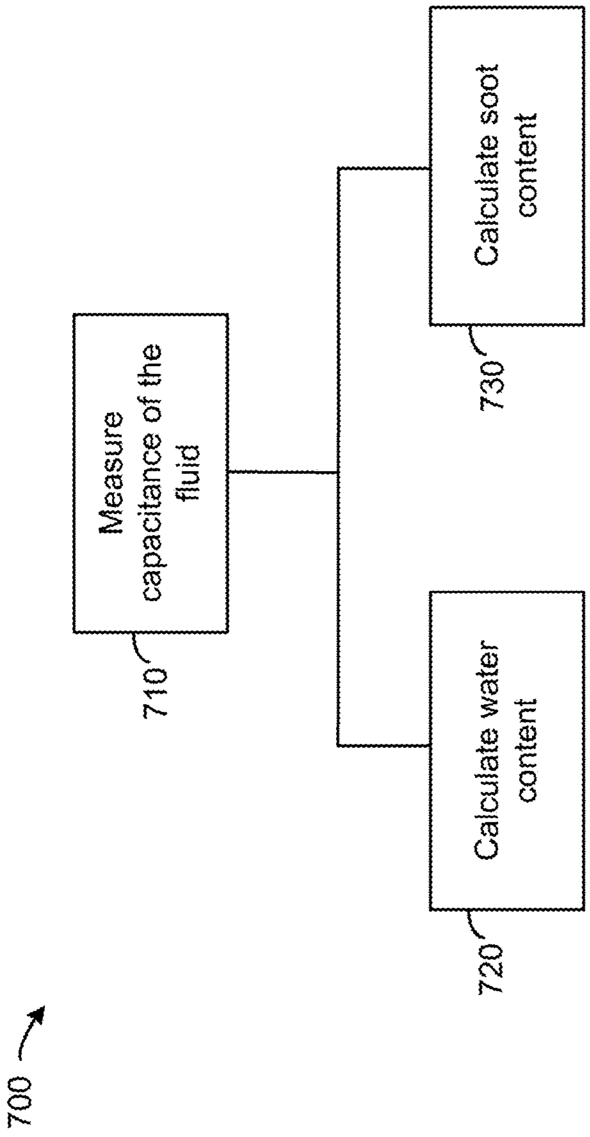
FIG. 7A is a flowchart of an example use of the probe of the fluid monitoring system of FIG. 2 in accordance with an embodiment.

Referring to FIG. 7A, shown therein is a flowchart 700 of an example use of a probe, such as probe 610*c* or 610*d*, that includes an electrical properties sensor. As shown in FIG. 7A, at 710, the electrical properties of the fluid are measured. For example, the electrical properties sensor of the probe can be used to measure the electrical properties of the fluid. In some embodiments, the electrical properties measurement obtained at 710 is calibrated using temperature data from a temperature sensor since electrical properties can be temperature dependent. For example, the temperature sensor can be located on the same probe as the electrical properties sensor, or on a different probe. In one embodiment, the electrical property of the fluid is the capacitance of the fluid.

At 720, the water content of the fluid is calculated based on the electrical properties measured at 710. Water has a dielectric constant that is significantly higher than the fluid, such as machinery fluid, that may be monitored by the fluid monitoring systems described herein. For example, the relative dielectric constant ($\varepsilon_r$) of water is approximately 80.1 whereas the relative dielectric constant of a lubricant, such as hexadecane, is approximately 2.04. Since water generally comprises a large portion of coolant formulations, the fluid monitoring systems described herein can identify coolant contamination of the fluid being monitored based on the determined water content of the fluid.

At 730, the soot content of the fluid is calculated based on the electrical properties measured at 710. The soot content of the fluid can be calculated based on electrical properties due to the high oxygen content of soot particles.

Figure 7B:
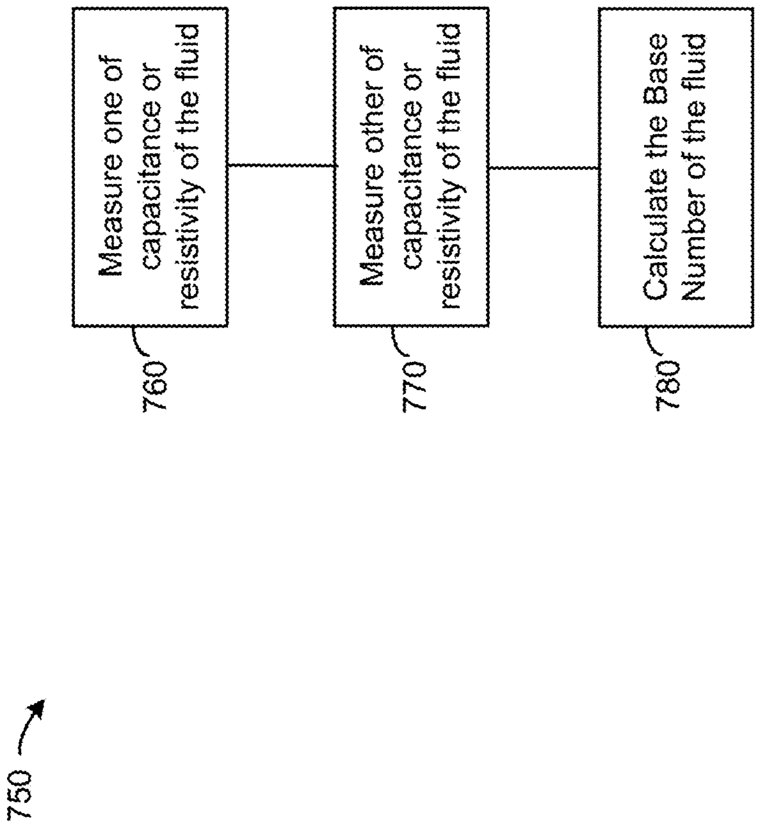
FIG. 7B is a flowchart of an example use of the probe of the fluid monitoring system of FIG. 2 in accordance with an embodiment.

Reference is next made to FIG. 7B, shown therein is a flowchart 750 of another example use of a probe, such as probe 610*c* or 610*d*, that includes an electrical properties sensor. As shown in FIG. 7B, at 760 and 770, electrical properties of the fluid are measured. For example, in one embodiment, at 760, one of the capacitance or resistivity of the fluid is determined. At 770, the other one of the capacitance or resistivity of the fluid is determined.

At 780, the Base number of the fluid is determined based on the capacitance and the resistivity of the fluid as determined at 760,770. In some embodiments, the electrical properties measurement obtained at 760,770 are calibrated using temperature data from a temperature sensor since electrical properties can be temperature dependent. For example, the temperature sensor can be located on the same probe as the electrical properties sensor, or on a different probe.

Figure 8:
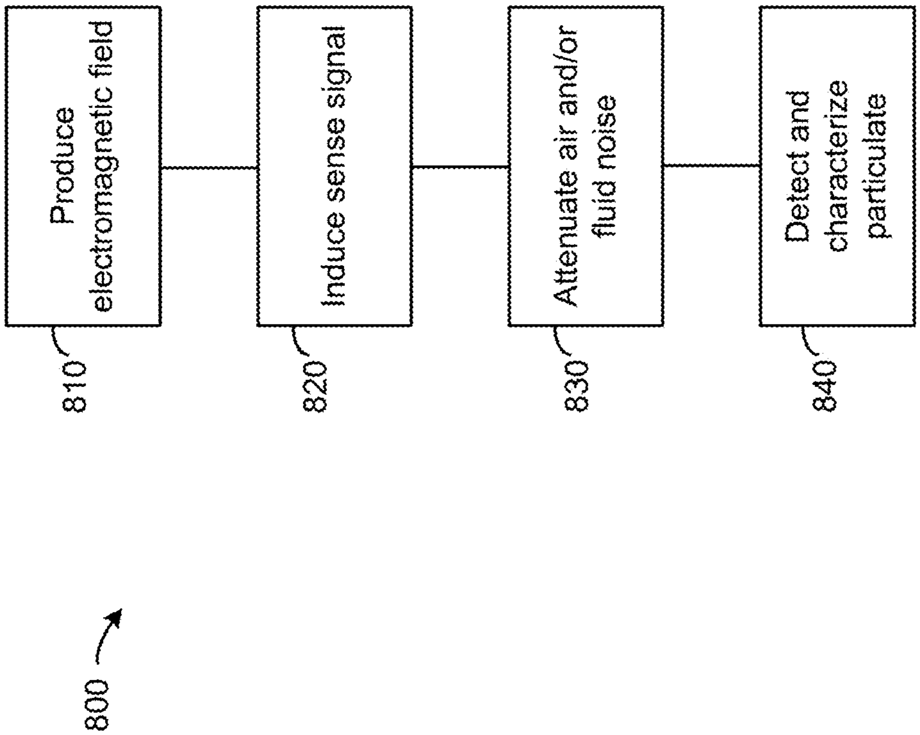
FIG. 8 is a flowchart of another example use of the probe of the fluid monitoring system of FIG. 2 in accordance with an embodiment.

Referring to FIG. 8, shown therein is a flowchart 800 of an example use of a probe, such as probe 610*d*, that includes an inductive sensor. As shown in FIG. 8, at 810, an electromagnetic field is produced by the inductive sensor. At 820, a sense signal is induced by the inductive sensor. At 830, the data obtained at 820 is processed to attenuate noise from air and/or the fluid. In some embodiments, step 830 is omitted. At 840, particulates are detected and characterized based on the data from step 820 and/or step 830.

In some embodiments, the inductive sensor includes a printed coil induction sensor, which is described in further detail with reference to FIGS. 10-25.

Figure 9A:
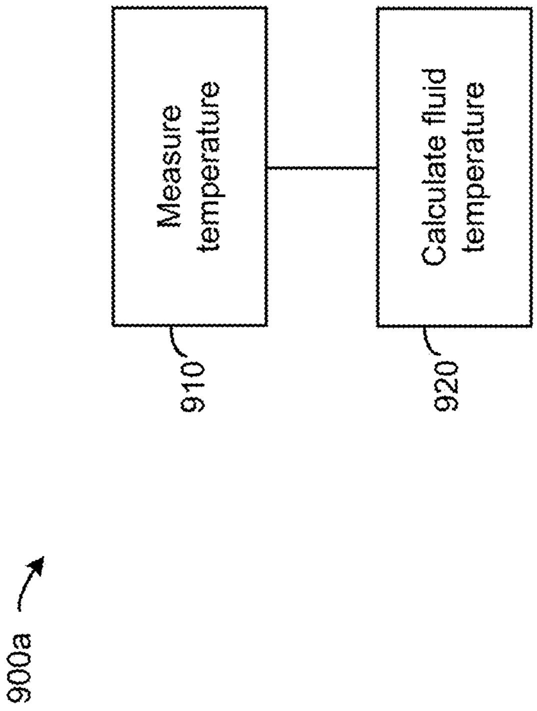
FIG. 9A is a flowchart of another example use of the probe of the fluid monitoring system of FIG. 2 in accordance with an embodiment.

Referring to FIG. 9A, shown therein is a flowchart 900*a* of an example use of a probe, such as probes 610*b-d*, that includes a temperature sensor. As shown in FIG. 9A, at 910, a temperature measurement is obtained. The temperature measurement can be obtained using any suitable temperature sensor. For example, the temperature sensor can include a resistance temperature detector. At 920, the temperature of the fluid is calculated based on the temperature measurement from 910.

As discussed herein, electrical properties measurements obtained by a electrical properties sensor described herein can be calibrated using temperature data since electrical properties measurement can be temperature dependent. Referring to FIG. 9B, shown therein is an example plot 900*b* of dielectric constant as a function of temperature for an example machinery lubricant oil. The dielectric constant is shown on the y-axis 930. The temperature is shown on the x-axis 940. The data 950 shows a decreasing proportional relationship between the dielectric constant 930 and temperature 940.

The relative dielectric constant of a particular fluid, $\varepsilon_r$, can be calculated based on the ratio of the capacitance of the fluid measured by an electrical properties sensor (C) to the measured capacitance of vacuum ($C_0$), as shown in equation (1). Experimentally, a measurement in air can be used if a measurement in vacuum is not possible.

$$\varepsilon_r = \frac{\varepsilon}{\varepsilon_0} = \frac{C}{C_0} \tag{1}$$

A fitted linear response of the sensor relative dielectric constant as a function of temperature, T (° C.), can be performed for the electrical properties sensor. For example, data 950 can be represented by equation (2).

$$\varepsilon_r = -0.00145(T) + 2.36 \tag{2}$$

Accordingly, the dielectric constant should be adjusted based on the measured temperature. In some embodiments, the adjustment is minor.

Figure 9C:
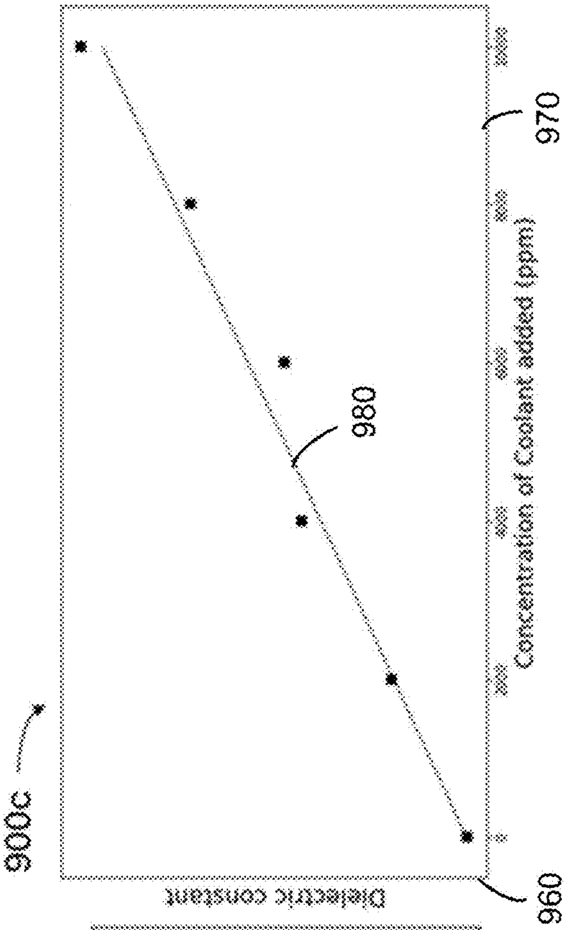
FIG. 9C is an example plot of measured dielectric constant as a function of coolant concentration in accordance with an embodiment.
Figure 9B:
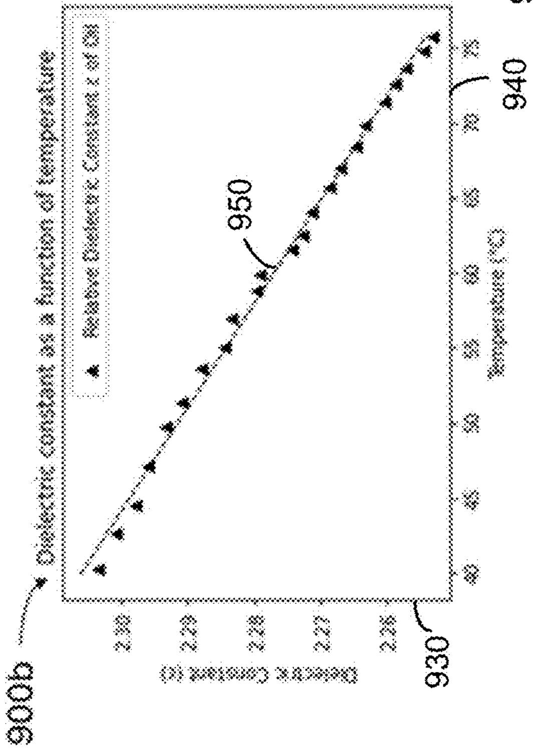
FIG. 9B is an example plot of measured dielectric constant as a function of temperature in accordance with an embodiment.

Referring to FIG. 9C, shown therein is an example plot 900*c* of dielectric constant as a function of coolant concentration in an example machinery lubricant oil. The coolant is predominantly a mixture of water and ethylene glycol in roughly 1:1 ratio. The dielectric constant is shown on the y-axis 960. The coolant concentration (ppm) is shown on the x-axis 970. The data 980 shows a proportional relationship between the dielectric constant 960 and coolant concentration 970.

As shown, coolant contamination (or water contamination), at a fixed temperature, will lead to increases in the dielectric constant.

As discussed herein, optical sensor measurements obtained by an optical sensing system described herein can be calibrated using temperature data. Further detail is provided with reference to FIGS. 38-40.

Reference is next made to FIG. 10, which illustrates a fluid monitoring system according to an example embodiment. The illustrated fluid monitoring system includes an optical sensing system 1000 interfacing with fluid 1010 within machine 1008. Optical sensing system 1000 comprises a computing device 1002, one or more light sources 1004, one or more light detectors 1006, sensing or probe element 1012, and cables 1014 and 1016. In various embodiments, the optical sensing system 1000 is configured to conduct online detection and measurements of the fluid 1010. In other embodiments, the optical sensing system 1000 is configured to conduct off-line detection and measurements.

Computing device 1002 may include a system control unit (SCU) containing electronics that perform data storage, data analysis, data/signal acquisition, communications, and/or other system control functions. The SCU interfaces with light sources 1004 and the detectors 1006. In one or more embodiments the SCU is adjacent to the light sources 1004 and the detector 1006 is separated from probe element 1012.

In one or more embodiments, the SCU includes a data acquisition device containing data acquisition and processing software connected to a housing including the one or more light sources 1004 (e.g., LEDs), one or more detectors 1006 (e.g., a spectrometer), and electronics to control the operation of the light sources 1004. The detector 1006 can be powered and controlled via a connection to the computing device 1002, such as a USB cable from the device.

Machine 1008 may be any asset that includes a fluid system. For example, machine 1008 can be any asset that requires the use of lubricant oil for its operation, such as an engine or a gearbox.

One or more light sources 1004 is required for an optical measurement to take place. The light source 1004 can be LEDs (light emitting diodes), which can be semiconductor-based emission sources. The LEDs may be UV (Ultraviolet) wavelength LEDs. Visible wavelength LEDs may also be used in addition to the UV wavelength LEDs. In other embodiments, light sources are non-LED based. Light sources can comprise gas phase or solid-state lasers, high and low pressure hollow-cathode lamps, arc lamps with and without monochromators.

One or more detector system 1006 transduces light into electrical signals. The detector system 1006 can be a spectrometer or a spectrophotometer, which provide spectral resolution such that incoming light intensity is spread across spectrometer channels. Spectrometers can comprise one or more CCD (Charge Coupled Device) or CMOS (Complementary metal-oxide-semiconductor) silicon devices. Spectrometers can also comprise Czerny-Turner based monochromator systems in conjunction with a photomultiplier tube (PMT), photodiode detector or CCD or CMOS silicon detector. In other embodiments, the use of one or more absorptive or Fabry-Perrot filters can also be employed in conjunction with a PMT, photodiode detector or CCD or CMOS silicon detector.

In one or more embodiments, detector 1006 is a CMOS spectrometer that contains between 1-65536 channels and has relative spectral sensitivity of at least 5% between approximately 200 nm to approximately 1000 nm. In one or more embodiments, detector 1006 is a CCD spectrometer that contains between 1-65536 channels and has relative spectral sensitivity of at least 5% between approximately 200 nm to approximately 1000 nm. Fiber optic cables 1014 and 1016 are glass fibers that transmits photons from one end to another through the principle of total internal reflection. The fibers typically comprise one or more of a core, cladding, and coating.

In some embodiments, the fiber optic cores have a diameter of approximately 10-2000 μm, or more preferably, approximately 100-800 μm. The coating may be polyimide or another coating that confers low and high temperature rating. Fiber optic cables can be terminated with industry standard connectors, such as SMA (subminiature assembly).

In some embodiments, fiber optic cables 1014 and 1016 comprise high OH fiber, which refers to optical fiber with a high hydroxyl ion (OH) concentration. The use of high OH fiber can be advantageous for UV transmission.

In some embodiments, fiber optic cables 1014 and 1016 comprise solarization resistant fibers, which are fibers that have been exposed to deep ultraviolet radiation. These fibers are treated to withstand the effects of high energy UV photons and maintain high transmittance over UV wavelength regions.

In some embodiments, the probe element 1012 is in physical contact, or near physical contact with the fluid. The diameter of the probe element may be between approximately 1-1000 mm. In various embodiments, the probe element comprises an optically transparent window that permits the transmission of the excitation light into the fluid. The optically transparent window can be made of sapphire or another optically clear material such as quartz or borosilicate glass.

Optically transparent windows have wavelength specific transmissions that that are sufficiently high. Light transmission through a window can be measured as a wavelength specific transmission coefficient between 0-100%, where 0 corresponds to no light transmission and 100% to all light being transmitted compared with a reference measurement where no window is present. In some embodiments, the window has a simple average transmission in the ultraviolet and visible wavelength spectral regions, from 250 nm to 850 nm greater than 10%, preferably greater than 50%.

The optically transparent window separates the volume inside the probe element, where the probe tips are located, and the fluid.

In some embodiments, the light emitted by the sample passes through the same optical window as the one through which the excitation light was delivered. In other words, a reflectance geometry for the probe element is employed.

As described herein, in some embodiments, the angle of the optically transparent window with respect to the longitudinal axis of the probe is approximately 45°. Alternatively, the optically transparent window has an angle other than 45°, or more generally is between approximately 0° to approximately 90°.

The optical sensing system 1000 may be based on optical methods such as optical absorbance (near infrared or infrared), Raman spectroscopy, hyperspectral imaging, surface plasmon resonance, or other non-linear optical techniques.

Reference is briefly made to FIGS. 37A and 37B to illustrate the functionality of apparatus 1000 of FIG. 10. FIG. 37A illustrates a flowchart 3700*a* for an example method for monitoring one or more properties of a fluid using a probe as described herein. At 3710, an excitation light is transmitted to the fluid. At 3720, an emission light is received from the fluid. At 3730, a processor is operated to obtain one or more fluorescence spectra based on the received emission light. At 3740, the processor is operated to determine a fluid condition indicator based on the one or more fluorescence spectra.

Referring to FIG. 37B, shown therein is a flowchart 3700*b* for an example method for monitoring one or more properties of a fluid using a probe as described herein. At 3750, an excitation light is transmitted to the fluid. At 3620, an emission light is received from the fluid. At 3770, a processor is operated to obtain one or more fluorescence spectra based on the received emission light. At 3780, the processor is operated to determine a remaining useful life of the fluid based on the one or more fluorescence spectra.

In one embodiment, the optical sensing apparatus 1000 is a fluorescent sensor which can detect contaminants and additives using the fluorescence phenomenon. Fluorescence measurements are based on the principle of absorbance of photons and re-emission of photons of lower energy, or higher wavelength. First, current is sent at the correct voltage to the LEDs 1004 so they generate UV photons. The LED light is delivered to the fluid sample in the probe element 1012 through fiber optic cables 1014 whose ends are enclosed within the probe body. The amount of energy delivered by the UV LEDs can be controlled using pulse width modulation. The fluid sample in contact with the probe element 1012 absorbs the LED light and remits photons of lower energy. The lower energy photons pass through the returning fiber optic cable 1016 and are received by the detector 1006, where the light signal is transduced to an electrical signal.

An advantage of using fluorescence spectroscopy in oil condition and concentration monitoring is that in general only certain additives fluoresce while the base oil does not. Therefore, the technique can be considered "background-free" to some extent, and a high signal to noise ratio can be achieved. Further, the fluorescence measurement is not impacted by vibrational frequencies. This is because the optical measurement frequencies are approximately 750-430 THz (400 nm-700 nm), and so they do not couple significantly to any vibrations between 1-3000 Hz, such that it would interfere with the overall measurement.

Using fluorescence to measure fuel contamination or antioxidant depletion can be advantageous because molecular species have unique fluorescence spectra. In various embodiments, the information obtained from taking a fluorescence measurement includes the line shape, line width and peak central wavelength. It is generally possible to distinguish between mixtures of fluorescence species using these features and data analysis algorithms. Common machinery fluids (e.g. fuel and lubricants) are comprised of mixtures of fluorescent molecules. Furthermore, using fluorescence to measure fuel antioxidant stability or antioxidant depletion can be advantageous to prevent coking of the fuel and subsequent damage to other components of the engine. Such antioxidant additives exhibit strong fluorescence responses, allowing early detection of antioxidant degradation and enabling proactive maintenance before harmful deposits or coking occur.

In some embodiments, the one or more light sources 1004 and the one or more detectors 1006 are carefully selected based on knowledge of target contaminants and additives in the fluid 1010. Depending on the particular chemical species in the fluids associated with a particular industry or application, the component configurations may vary. This is done to ensure that the correct excitation LEDs are present within the configuration to excite the target species fluorescence response, and an appropriate spectrometer with sufficient spectral range and resolution is present to detect the fluorescence response.

Excitation using narrow light sources can be advantageous in isolating the fluorescence responses of molecules in the fluid 1010, and simplifying elements of the data analysis. If multiple light sources are used at the same time, then it may induce spectral distortions or other self-absorption effects.

In various embodiments, light sources are typically operated separately and sequentially, rather than simultaneously because it is preferable that the fluorescence response of each compound in the lubricant mixture be excited independently. This allows for subsequent determination of the additives and fuel contaminants. The specific light source that is employed largely depends on the specific molecular target, and possible absorptive interferences from other molecules in the fluid 1010. In one or more embodiments, light sources 1004 are selected carefully using chemical knowledge of the system.

For exemplary purposes only, referring to FIG. 11, graph 1102 shows an example of fluorescence spectra 1104 and 1106 of a sample of store-bought tonic water obtained using two different LED light sources. The target additive in tonic water that provides the fluorescence response is the molecule quinine, or a salt thereof.

In one embodiment, the fluorescence spectrum of quinine is measured with a fluorescence optical sensing apparatus 1000, where the light source 1004 is an LED with a central wavelength of 365 nm or 405 nm, or another suitable wavelength. The detector 1006 is a CMOS spectrometer with a spectral range that covers the fluorescence spectral range of quinine in tonic water from 400-600 nm, and a spectral resolution from 400 nm-600 nm of 10 nm. The measured fluorescence spectrum of quinine is substantially the same using either a 365 nm or 405 nm light source in this embodiment because there are no spectral interferences present within the tonic water mixture at either of these excitation wavelengths.

In one or more embodiments, the fluid is a lubricating oil and the target molecule to which fluorescence optical sensing apparatus 1000 is configured to is antioxidant(s) N-Phenylnaphthalen-1-amine (CAS #90-30-2), or a derivative thereof, the antioxidant diphenylamine, or a derivative thereof (CAS #122-39-4), or the antioxidant 2,6-Di-tert-butyl-p-cresol, otherwise known as Butylated hydroxytoluene (CAS #: 128-37-0) or a derivative thereof, or other antioxidant with known chemical structure. In other embodiments, the exact chemical structure of the target molecule is unknown, and the optical sensing apparatus 1000 is configured empirically based on experimental investigations.

In one or more embodiments, the fluid can contain one or more target molecules.

In one or more embodiments, the fluid can be a fuel-oil mixture, whereby the fuel is a contaminant in the lubricating oil. The target molecule is a molecular species present in the fuel. In one or more embodiments, the exact chemical structure of the target molecule present in the fuel is unknown, and the optical sensing apparatus 1000 is configured with light sources 1004 empirically based on experimental investigations.

Figure 12:
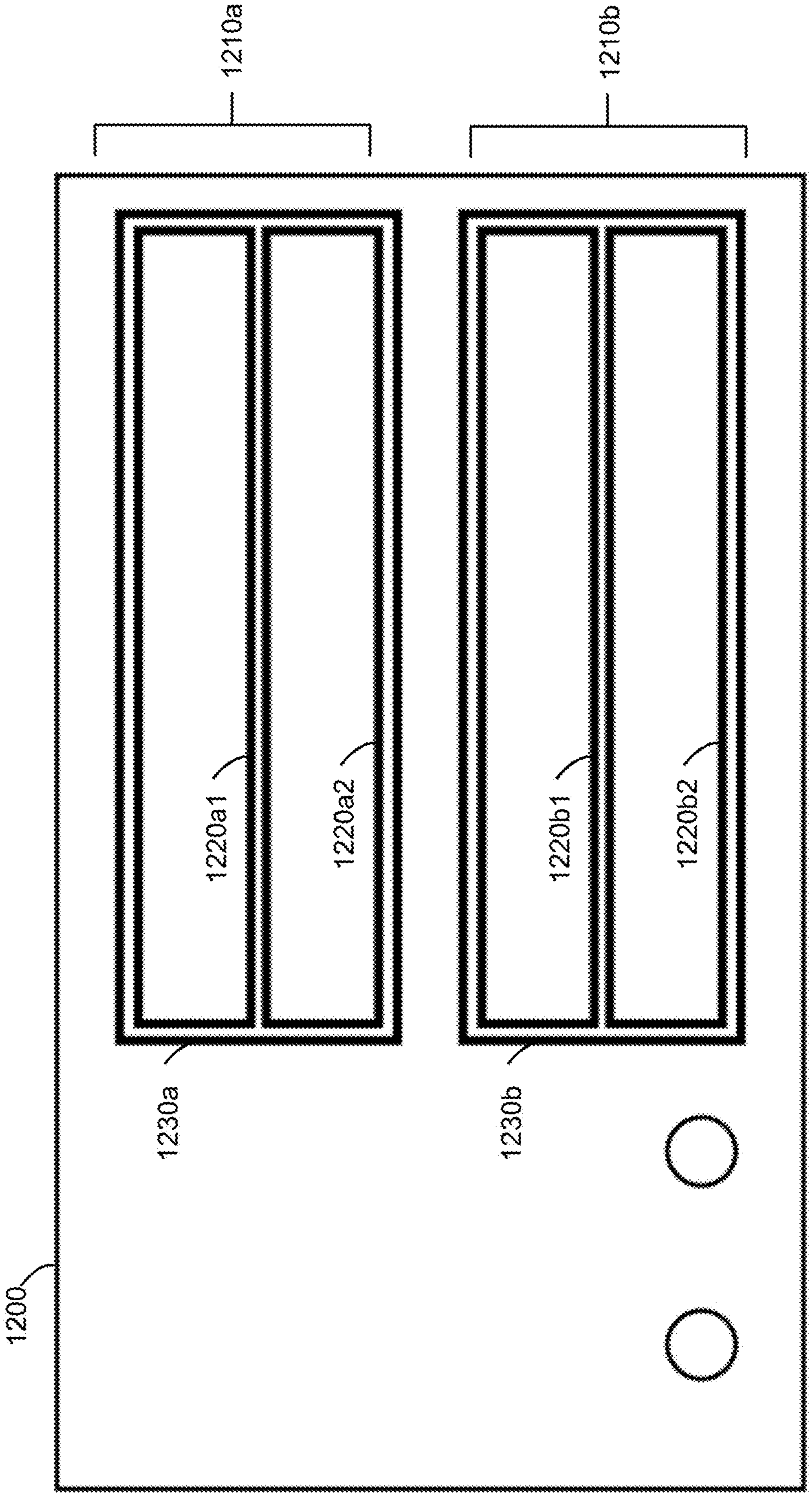
FIG. 12 is an illustration of an example PCS in accordance with an embodiment.

FIG. 12 shows a flowchart 1200 for developing a prognostic model in order to determine the remaining useful life (RUL) of lubricant oil using fluorescence measurements in accordance with one or more embodiments described herein. In the absence of any lubricant contamination, the remaining useful lifetime is limited by thermal oxidation, and by extension the remaining concentration of antioxidant in the lubricant system. In this case, the fluorescence measurement can be used as a standalone technique for the determination of the oil RUL.

Antioxidants are additives designed to prolong the life of a lubricant by increasing the oxidative resistance of the base oil. During their use in lubrication systems, antioxidants will deplete to a certain critical level, at which point the lubricant will start to degrade at an accelerated rate. Therefore, monitoring the concentration of antioxidants can be effective method to determine the remaining useful life (RUL) of the lubricant.

The basic idea behind the fluorescence measurement is that the antioxidant (typically a fluorescent compound) concentration is proportional to the measured fluorescent intensity. There is typically one antioxidant per formulation, but some formulations have multiple antioxidants. The antioxidants can either be primary (that reacts with ·OH and RO· radicals) or secondary (react with hydroperoxides). In either case, the method requires that the targeted antioxidant fluoresce under UV or visible wavelengths excitation. One or more of the antioxidant and its reaction byproducts may be monitored.

At 1210 of method 1200, fluorescence spectra from the fluorescence sensing apparatus are obtained. The fluorescence sensing apparatus may be apparatus 1000 of FIG. 10. An example can be seen in FIG. 13, where spectral traces 1308, 1309, 1310, and 1311 corresponding to different lubricant aging times are shown in graph 1302. Traces 1308 to 1311 are labelled chronologically (i.e., 1308 is an earlier time and 1311 is a later time).

The x-axis 1304 over which the integral is performed does not need to be in units of wavelength (e.g., nm). It can also be in units of energy, for example wavenumbers (cm-1) or electron volts (eV). Converting the x-axis from wavelength, which is the typical default for a measurement obtained on a spectrophotometer, to an energy axis does not substantially alter the method. The y-axis 1306 represents the fluorescence intensity, which is an indication of how much light is emitted by the sample. The fluorescence intensity depends on the concentration of one or more fluorescent compounds within the sample.

At 1220 of method 1200, one or more integrals of a fluorescence spectrum is computed. The process can be repeated for multiple fluorescence spectra that are obtained by one or more excitation sources (e.g. UV LED). The concentration of a particular antioxidant species or antioxidant oxidation product is proportional (a) to the integral of its fluorescence spectrum:

$$\text{Antioxidant } conc\ \alpha \int_{\lambda_1}^{\lambda_2} I(\lambda)d\lambda \tag{3}$$

Therefore, to monitor the concentration of an antioxidant compound or an antioxidant oxidation product, an integral of its respective fluorescence spectrum can be computed over the course of the lubricant degradation. In the example shown in graph 1302 in FIG. 13, the integral is bounded by the limits of integration over a certain wavelength range.

A computing device, such as device 1002 of FIG. 10, may be used to compute the integral. This can be done in different ways. In some embodiments, the method used to compute the integral is an unweighted sum of the intensities within the integration wavelength limits. This can be done using a modern programming language or application, such as Python®, MATLAB®, Excel®.

Integration is carried out in the same manner for each recorded spectral trace.

At 1230 of method 1200, the Fluid Condition Indicator (CI) values are plotted as a function of time. An example can be seen in graph 1312 of FIG. 13. The Fluid CI 1314 in FIG. 13 refers to the normalized integrals calculated in 1220. The normalized integral for each of the spectral traces 1308 to 1311 is plotted as a data point 1316 in graph 1312 for each point in time to form trendline 1318. The x-axis 1320 represents the time since the last oil change.

At 1240 of method 1200, a critical Fluid CI value 1322 is set. For example, the RUL can be determined when the intensity of a given antioxidant spectral intensity reaches a certain critical percentage of its initial intensity. For example, in graph 1312 of FIG. 13, a relative value of 25% is assumed for the critical Fluid Condition CI value 1322.

Figure 13:
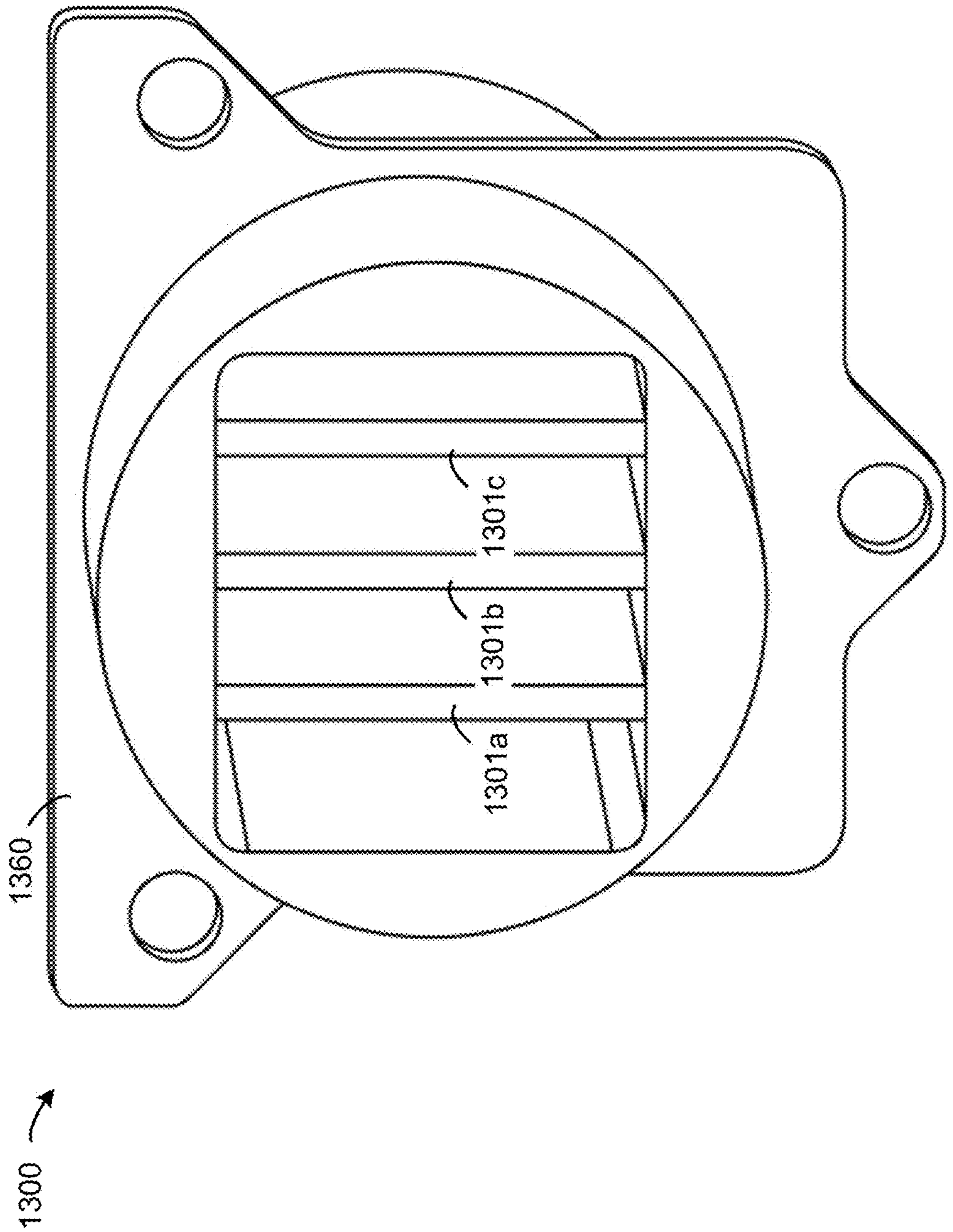
FIG. 13 is an illustration of an example PCS array structure in accordance with an embodiment.

At 1250 of method 1200, the trend in graph 1312 of FIG. 13 is extrapolated to the point where the critical Fluid CI value 1322 is reached. This is done in the absence of data that covers the entire desired range. Ideally, the training data used to fit the prognostic function covers the entire domain where the RUL is computed.

At 1250, the method 1200 may involve fitting an equation that can predict the loss of the primary antioxidant. For example, an exponential function may be used to extrapolate the degradation rate described by Equation 4:

$$\text{Antioxidant remaining} = Ae^{-\frac{t}{B}} + C \tag{4}$$

The fluorescence data plotted in graph 1312 of FIG. 13 can be used to obtain the parameters A, B, C in the fitted equation (4):

$$y = 0.847\exp\left(\frac{-t}{60.225}\right) + 0.153 \tag{5}$$

At 1260 of method 1200, the RUL is calculated. RUL can then be defined as:

$$RUL = \Delta t = t_2 - t_1 \tag{6}$$

where t1 is the current time. Conventionally, t0=0 is the time corresponding to immediately after a fresh oil change, and all time after that is the time since the fresh oil change.

To solve for t2, the prognostic function based on the fitted data can be rearranged. Using the exponential decay model, t2 can be solved for by rearranging the terms in equation (4):

$$t_2 = -\ln\left(\frac{y_2 - C}{A}\right)B \tag{7}$$

Substituting using the parameters from equation (5), t2 can be computed:

$$t_2 = -\ln\left(\frac{0.25 - 0.153}{0.847}\right)60.225 = 130.5 \tag{8}$$

Then using equation (6), and assuming, for example, that the current time t1 is 40 hours (i.e., 40 hours since the last fresh oil change), the RUL can be determined:

$$RUL = \Delta t = 130.5 - 40 = 90.5 \text{ hours} \tag{9}$$

In some embodiments, other numerical models can be used empirically as a prognostic model, such as an $n^{th}$ degree polynomial function. The monoexponential decay is just one possible simple prognostic model, albeit one that is well supported by chemical kinetics theory.

In some embodiments, a remaining useful lifetime can be set based on the projected amount of time for which is takes for the antioxidants to reach 25% or 50% of their initial concentration.

In some embodiments, the Fluid CI values at 1220 of method 1200 are computed through a ratio of two or more fluorescence integrals computed from one or more fluorescence spectra and then normalized.

In some embodiments, antioxidant depletion can be monitored using other well established chemometric or machine learning algorithms. For example, such algorithms can include a combination of one or more of: support vector machines and its variants, ridge regression and its variants, lasso regression and its variants, partial least squares and its variants, parallel factor analysis and its variants, multivariate curve resolution-asymmetric least squares and its variants, decision trees and its variants, singular value decomposition and its variants, principle component analysis and its variants, simple-to-use Interactive Self-modeling Mixture Analysis and its variants, orthogonal projection approach-asymmetric least Squares and other chemometric or machine learning algorithms.

The RUL can also be determined by other lubricant parameters than the fluorescence intensity decreasing to a particular amount if those lubricant parameters correlate with antioxidant depletion. The acceptable limits that govern the computation of RUL depends on the particulars of the machinery application and customer. FIG. 38 shows reference tables outlining recommended ranges for oxidation and lubricant contaminations that would limit the useful life of the lubricant.

FIG. 14 shows a flowchart 1400 for determining the RUL of lubricant oil based on other lubricant parameters such as the change in Acid Number (AN), Number (BN), oxidation number (ON), and/or viscosity, in accordance with one or more embodiments.

At 1410 of method 1400, the fluorescence dataset is obtained from the fluorescence sensing apparatus. The fluorescence sensing apparatus may be apparatus 1000 of FIG. 10.

At 1420 of method 1400, a secondary dataset based on measurements of a second lubricant parameter is obtained. The second lubricant parameter can be the Acid Number (AN), Base Number (BN), oxidation number (ON), viscosity, or another parameter that correlates with the oxidation of the base oil. A secondary dataset may be obtained using offline techniques. For example, in the case of oxidation number, this metric can be measured using established methods such as ASTM 7414, where the oxidation number is obtained using an FTIR instrument.

At 1430 of method 1400, the fluorescence dataset and the secondary dataset are correlated. The oil condition indicator (CI) may be obtained from the fluorescence data using methods described in method 1200. Graph 1500 of FIG. 15 shows that the oxidation number data plot 1502 is inversely related to condition indicator data plot 1504 in this example when plotted against time 1506. The left y-axis 1508 represents the Fluid Condition CI and the right y-axis 1510 represents the oxidation number. These two independently collected datasets may be used to generate a fitted relationship, or lookup table, between the two measured quantities. Graph 1512 of FIG. 15 shows the relationship 1514 between the Fluid Condition CI 1516 and the oxidation number 1518 through fitting an empirical function to a plot of these two measurements. Referring to FIG. 16, example plot 1600 shows the relationship 1602 between the Fluid Condition CI 1606 and the Acid Number 1604 through fitting an empirical function to a plot of these two measurements.

At 1440 of method 1400, a threshold value for the second lubricant parameter is set. This may be determined with reference to table 3800 shown in FIG. 38.

At 1450, the method 1400 includes finding a fluorescence condition indicator value where the threshold value for the second lubricant parameter has been exceeded. This can be done through the empirical relationship, or the lookup table obtained in 1430. In the case of oxidation number, the RUL can be determined from the CI value 1508 where the oxidation number 1510 has exceeded the threshold set in 1440. In the case of acid number, the RUL can be determined from the CI value 1606 where the Acid Number 1604 has exceeded the threshold set in 1440.

In one embodiment, the fluorescence sensing apparatus 1000 is employed to monitor fuel contamination. The fluorescence sensing apparatus 1000 can selectively target molecular components of fuel rather than its impact on the electrical properties or the viscosity of the lubricant fluid, allowing for higher sensitivity to fuel contamination compared to purely electrical methods.

Figure 17:
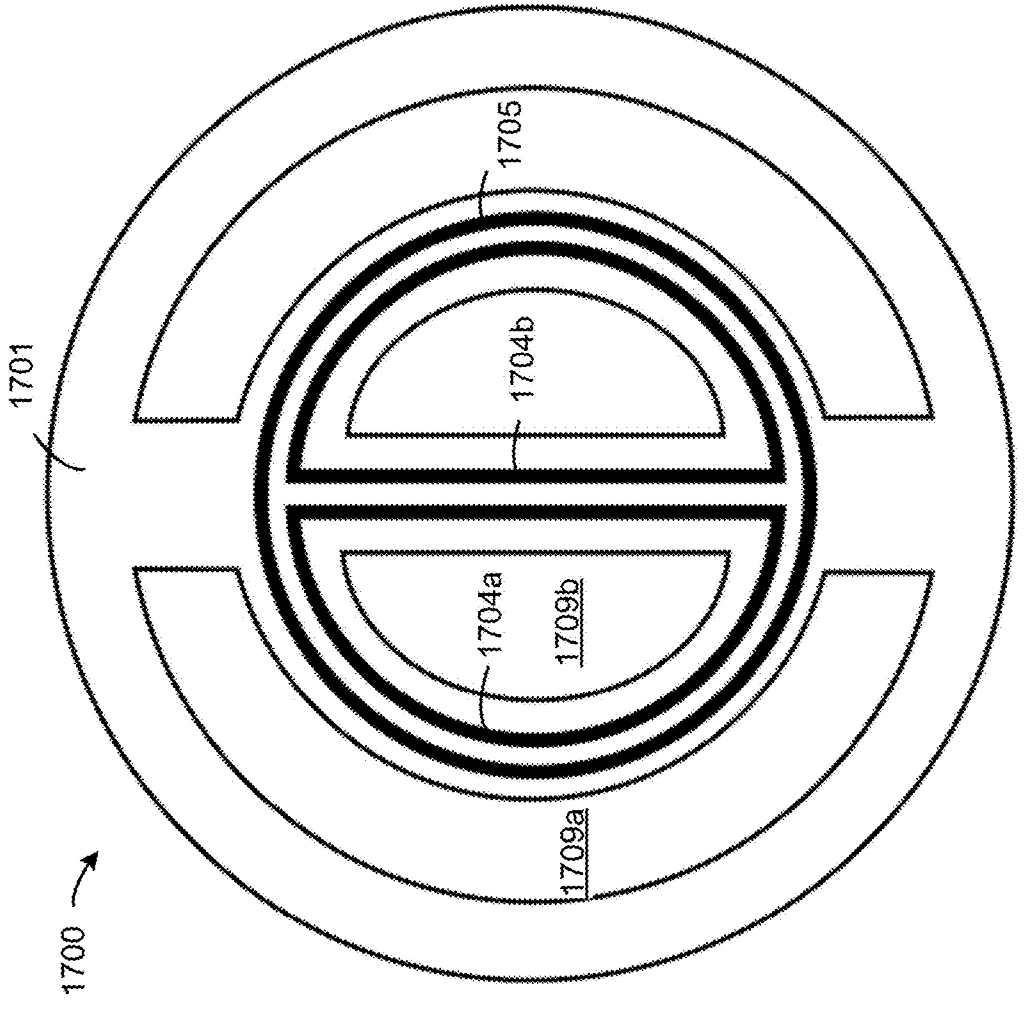
FIG. 17 is an illustration of an example double-D PCS in accordance with an embodiment.

FIG. 17 shows a flowchart 1700 for developing a calibration curve used to determine the concentration of fuel in the lubricant oil.

At 1710, the method 1700 includes obtaining a reference fluorescence spectrum of the lubricant oil without any fuel contamination. The cumulative fuel contamination may be low (i.e., less than 10 wt %) so the overall impact of fuel contamination on the fluorescence spectra may not be obvious when looking at the superimposed fluorescence spectra such as the one shown in graph 1800 of FIG. 18. The x-axis 1802 is the emission wavelength and the y-axis 1804 is the fluorescence intensity. At t=0, it is assumed that there is no fuel, and therefore this measurement can be used as a spectral background that can be subtracted from each subsequent spectrum.

At 1720, the method 1700 includes obtaining subsequent fluorescence spectra for increasing fuel concentrations. In other words, a fluorescence spectrum was obtained after each standard addition of fuel in the lubricant oil after sufficient time had passed to allow the fuel to properly mix with the viscous oil.

At 1730, the method 1700 includes subtracting the reference spectrum from the subsequent fluorescence spectrum after each fuel addition. Examples of the resulting isolated spectra can be seen in graph 1806 of FIG. 18, which correspond to different times. For example, spectrum 1808 corresponds to a fuel contamination of 0.6% and spectrum 1810 corresponds to a later point in time when the fuel contamination is 1.6%, at which point an alarm may be triggered.

At 1740, the integral of each isolated spectrum is calculated, similar to step 1220 in method 1200.

At 1750, the method 1700 includes correlating the calculated integrals 1814 and the concentration of fuel 1816 in the lubricant oil. A linear regression curve 1818 may be obtained, as shown in graph 1812 of FIG. 18.

In some embodiments, fuel contamination can be detected using other well established chemometric or machine learning algorithms. For example, such algorithms can include a combination of one or more of: support vector machines and its variants, ridge regression and its variants, lasso regression and its variants, partial least squares and its variants, parallel factor analysis and its variants, multivariate curve resolution-asymmetric least squares and its variants, decision trees and its variants, singular value decomposition and its variants, principle component analysis and its variants, simple-to-use Interactive Self-modeling Mixture Analysis and its variants, orthogonal projection approach-asymmetric least Squares and other chemometric or machine learning algorithms.

Relative increases in fuel can be assessed using one or more of the algorithms listed above. A variant of the partial least squares algorithm can be used, for example, in the context of relative detection of jet A1 fuel in Mobil Jet II oil samples, as shown by the regression curve 1906 in graph 1900 of FIG. 19. As shown, a data point 1908 of the integrated intensity 1910 is plotted against the fuel concentration 1912 for each recovered spectral component to obtain regression curve 1906.

In some embodiments, fluorescence data is processed for oil classification purposes. Oil classification is mainly done in the context of fresh oils, to ensure that an oil change has been correctly carried out. Oil classification can be carried out using one or more of data processing algorithms. For example, such algorithms can include a combination of one or more of: support vector machines and its variants, ridge regression and its variants, lasso regression and its variants, partial least squares and its variants, parallel factor analysis and its variants, multivariate curve resolution-asymmetric least squares and its variants, decision trees and its variants, singular value decomposition and its variants, principle component analysis and its variants, simple-to-use Interactive Self-modeling Mixture Analysis and its variants, orthogonal projection approach-asymmetric least squares and its variants, and other chemometric or machine learning algorithms.

Referring to FIG. 20, shown therein is an example graph 2000 for applying Principle Component Analysis (PCA) to a series of fluorescence spectra obtained on two aviation oils undergoing thermal oxidative aging. PCA can be applied to a series of fluorescence spectra measured throughout the thermal oxidative process. Different oils in various degradation states can be classified in this manner. The x-axis 2002 represents the first PCA component and the y-axis 2004 represents the second PCA component. Curves 2006 and 2008 represent two different types of engine oils used in the aviation industry. The ability of the invention to classify oil types in this manner depends on the number of samples and oil types in the reference library. Classification of an unknown sample will usually require that there is reference data available for comparison.

In some embodiments, temperature calibration can be used to correct the signal intensity of a given antioxidant. The fluorescence response of a fluorescent organic molecule is temperature dependent. The photoluminescence quantum yield (PLQY) of a fluorescent organic molecule can typically be described by equation (10):

$$PLQY = \frac{k\text{rad}}{k\text{rad} + \sum k non\text{rad}(T)} \tag{10}$$

Where Σknonrad(T) is a sum of all nonradiative processes. Generally, the higher the temperature, the lower the photoluminescence quantum yield, due to coupling with inter and intra molecular phonon modes.

For lubricants, the overall fluorescence intensity under the same data acquisition settings will decrease when the temperature increased. Example graph 3900 in FIG. 39 shows the impact of thermal quenching on the overall fluorescence intensity of diesel engine oil. Plot 3902 corresponds to a fluorescence spectrum of a fluid sample that is a 15 W-40 engine oil obtained at room temperature. Plot 3904 corresponds to the same fluid sample at a higher temperature of 120 degrees Celsius. As can be noted from the differences in intensities between the plots, the overall intensity drops as a function of temperature, but the overall spectra profile remains substantially the same. Temperature correction of the fluorescence intensity may be needed if the temperature is not kept constant throughout the machinery operation. The fluorescence response under different temperatures can be monitored with the fluorescence sensing apparatus 1000 and any temperature sensor as described herein.

For a marine diesel engine application, the temperatures are normally stable and fixed throughout its normal application. Temperature correction of fluorescence intensities is not generally required if the engine is maintained at this given operating temperature and the system has reached a thermal equilibrium. A demonstration of the invention installed in the lubrication system of a diesel generator is shown in example plot 4000 in FIG. 40, where the datapoints 4002 can be seen converging onto a trendline as the system reaches thermal equilibrium after the start of each day or operation, which is represented by the vertical lines 4006.

Reference will now be made to FIGS. 10A-24B and 30A-32B to describe embodiments of inductive sensors that can be included in the fluid monitoring systems described herein.

Many industries that involve the use of heavy machinery generally use "magnetic plugs" or "mag plugs" for debris monitoring within a fluid. Mag plugs include a magnet that is installed within a fluid such that it can magnetically capture ferrous debris within the fluid. The captured debris can be examined by a technician to identify properties that indicate that the debris is the result of component failure, such as gear box failure or bearing failure. The failure of such components can result in significant damage to expensive equipment, and pose a risk to human safety (e.g., applications involving aircraft turbine engines).

Mag plugs take up little space and weight when installed. However, mag plugs have several drawbacks. For example, smaller debris particles that may be captured by mag plugs generally are not actually indicative of component failure, but are produced in large quantities, which requires technicians to perform high volumes of assessment to determine whether the captured debris is a concern with respect to component health. Additionally, the fraction of particles captured by mag plugs with respect to the total number of particles that pass by the mag plug is relatively low (e.g., as low as 10%). This can result in increased time to detect component failure. Furthermore, mag plugs can only capture ferrous material. Although most gear box and bearing components are ferrous, there are certain components in bearings and seals, for example, which are metallic but non-ferrous, and accordingly would not be captured by a mag plug.

Online debris monitoring solutions exist as alternatives to mag plugs, and in addition to solving the above challenges, also provide particle-level information such as total particle counts, individual particle size and material. This additional particle-level information can be used to not only look at the cumulative counts and mass of debris, but also to look at rates at which different sizes of particles are being detected. These particle detection rates can be used to greatly increase the reliability of both diagnostic and prognostic predictions. Furthermore, since different failure modes generate different particle-size distributions, the particle-level sizing analysis of online wear debris analysis can be used to focus only on particle size ranges of interest to a given failure mode.

While online debris monitoring has many advantages over either simple mag plugs or electronic chip detectors, existing online debris monitoring solutions generally have other drawbacks. For example, many existing debris monitoring solutions do not scale efficiently to larger fluid pipe diameters. One solution to this problem is to bypass a smaller volume of flow out of the main pipe and into a smaller diameter pipe to then analyze the fluid in the smaller diameter pipe. This adds installation complexities and added costs. Additionally, existing online debris monitoring solutions are often heavy, which limits their use in certain applications, such as aerospace applications. Owing to this, only one system may be used in a common scavenge line, instead of having an individual system for each scavenge line for fault isolation as is the current practice with mag plugs. Mag plugs are the dominant debris monitoring implementation in many heavy machinery applications, and many manufacturers fit equipment with standard threaded ports for mag plugs. Online debris monitoring systems are often larger than mag plugs and may require replacement of entire sections of a pipe for installation. Also, environmental noise caused by, for example, vibration, non-uniform media (e.g., air bubbles, soot, or other contaminants present in the fluid being monitored), and thermal and/or pressure fluctuations, poses a challenge to designing an online debris monitoring system that can detect acceptable levels of small enough particles that are indicative of component damage (e.g., particles that are approximately 100 microns to 400 microns in size). Finally, some debris monitoring systems that rely on particle capture tend to capture particles that are smaller than the particles that are indicative of component damage.

Embodiments of the inductive sensors described herein include printed circuit board (PCB) based inductive sensors for fluid debris monitoring that are designed to operate in contact with (e.g., submerged or partially submerged) the fluid to be monitored. These embodiments of the inductive sensors may be referred to as printed-coil sensors (PCSs). Any of the inductive sensors described herein can include one or more of the PCS embodiments described herein.

Figure 10B:
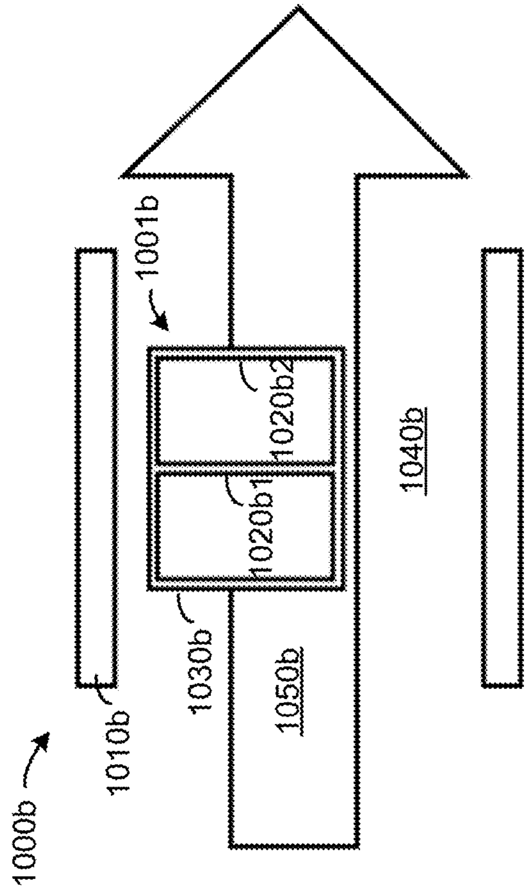
FIG. 10B is a cross-sectional illustration of an example printed-coil induction sensor (PCS) in accordance with an embodiment.

The PCSs described herein are designed to detect debris particles that are approximately 10-3000 microns in diameter. The data obtained by a PCS can be processed (e.g., phase analysis of the measured signal) to determine material properties of the detected debris particle. For example, a phase analysis can be performed to determine whether the detected debris particle is ferrous or non-ferrous. The PCSs described herein can vary in shape, size, and dimensions, and can include designs that are smaller than typical non-capture inductive sensors. For example, the PCS can be designed to fit within ports as small as ⅜ inch. The PCSs are non-capture sensors and accordingly, are not sensitive to a build-up of small particles. In some embodiments, PCSs are configured to be submerged into the flow, such as, for example, as illustrated in FIG. 10B. In some other embodiments, PCSs are configured to be installed orthogonal to the flow with any number of openings in the PCB for the flow to pass through.

The PCSs described herein also include features to address common noise problems experienced by inductive sensors. For example, the PCSs can include an embedded Faraday shield to limit interactions between the PCS and the environment. Such feature is particularly important for preventing noise generated by the environment around the coils. The PCSs can be configured to include ancillary sensors, such as thermal and/or vibration sensors, which can be used to reduce thermal drift and/or vibrational noise. Furthermore, a model, such as a machine-learning model, can be used to distinguish signals generated by debris in the fluid from a largely vibration-dominant noise floor.

In some embodiments, the PCSs as described herein can comprise any suitable PCB material. In some embodiments, the PCB material comprises Isola P96, Tachyon 100G, and/or FR4. However, these materials are provided as examples only, and other suitable PCB materials can be used.

Since the PCSs include a PCB that contacts a fluid, the wires connecting the PCB to the probe are hermetically sealed, i.e. enclosed or packaged so that the wires are completely airtight and impervious to external fluid. This can be accomplished using a PAVE hermetic feedthrough sealing combination with an epoxy, such as DP-125. However, these materials are provided as examples only, and other suitable epoxy materials can be used.

Figure 10A:
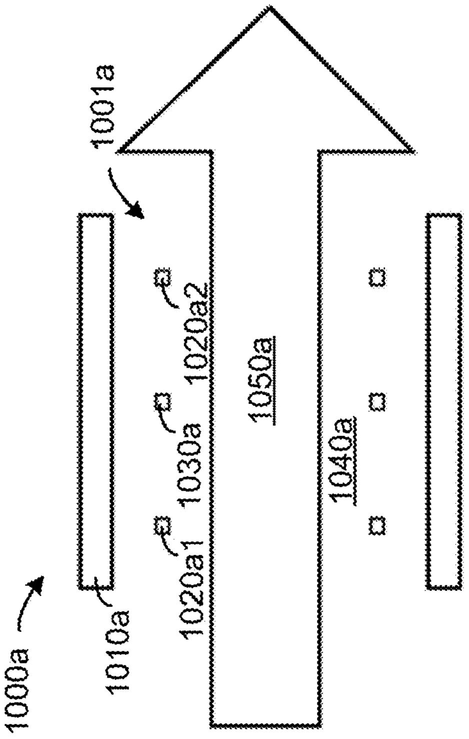
FIG. 10A is a cross-sectional illustration of an example flow-through debris monitoring sensor in accordance with an embodiment.

Referring now to FIG. 10A, shown therein is a cross-sectional illustration 1000*a* of an example flow-through debris monitoring sensor 1001*a*. As shown in the example in FIG. 21A, the debris monitoring sensor 1001*a* is installed in a pipe 1010*a* having a fluid 1040*a* flowing in direction 1050*a*. The illustrated debris monitoring sensor 1001*a* includes field coils 1020*a*1 and 1020*a*2, and sense coil 1030*a* which are wound around the pipe 1010*a*. As shown in FIG. 10A, the fluid 1040*a* flows through the debris monitoring sensor 1001*a*.

Referring now to FIG. 10B, shown therein is a cross-sectional illustration 1000*b* of an example printed-coil induction sensor (PCS) 1001*b*. As shown in the example in FIG. 10B, the PCS 1001*b* is installed in a pipe 1010*b* having a fluid 1040*b* flowing in direction 1050*b*. The illustrated PCS 1001*b* includes field coils 1020*b*1 and 1020*b*2, and sense coil 1030*b*. As shown in FIG. 10B, the PCS 1001*b* is inserted into the fluid 1040*b* and the fluid 1040*b* flows around the PCS 1001*b* (e.g., rather than through the sensor).

In some embodiments, the PCS 1001*b* may be implemented using one field coil and two sense coils. In some other embodiments, the PCS 1001*b* may be implemented using a different combination and configuration of the field and the sense coils.

Figure 20B:
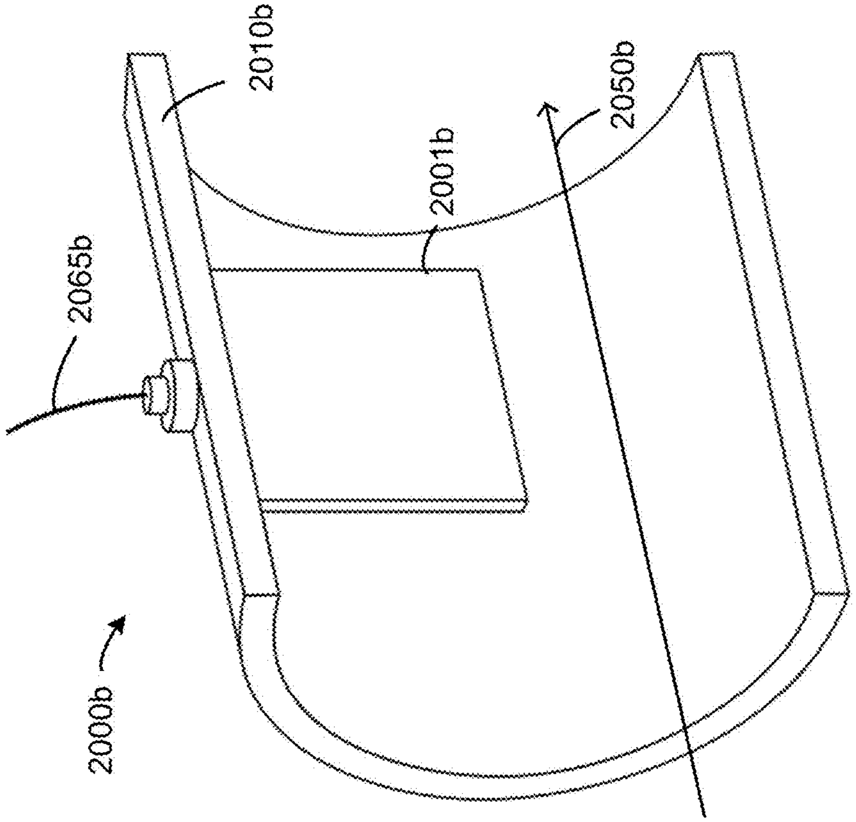
FIG. 20B is an illustration of another example PCS in accordance with an embodiment.
Figure 20A:
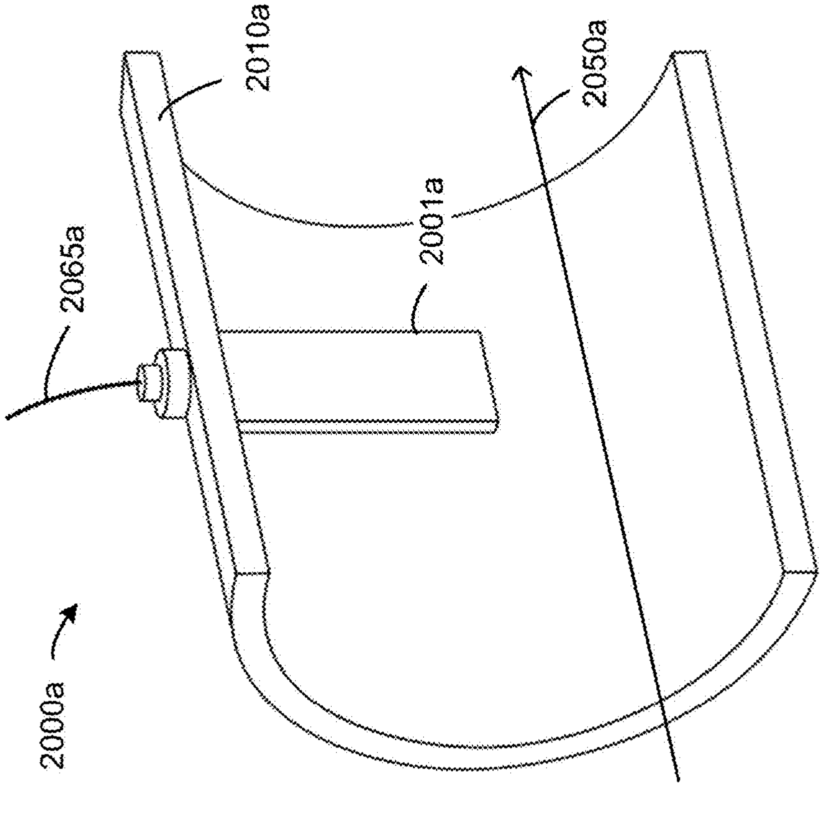
FIG. 20A is an illustration of an example PCS in accordance with an embodiment.

Referring briefly to FIG. 20A, shown therein is an illustration 2000*a* of an example PCS 2001*a* installed in a pipe 2010*a*. PCS 2001*a* is connected to a processor, such as processor 220, via cable 2065*a*. As shown, fluid within the pipe 2010*a* flows in direction 2050*a* around the PCS 2001*a*.

Referring briefly to FIG. 20B, shown therein is an illustration 2000*b* of an example PCS 2001*b* installed in a pipe 2010*b*. PCS 2001*b* is connected to a processor, such as processor 220, via cable 2065*b*. In the illustrated example, PCS 2001*b* is a larger-coiled format compared to PCS 2001*a*. As shown, fluid within the pipe 2010*b* flows in direction 2050*b* around the PCS 2001*b*.

Returning now to FIG. 10B, PCS 1001*b* is based on a three-magnetic-coil design. Two of the coils, 1020*b*1 and 1020*b*2 are field coils, which are electrically driven to produce a magnetic field. One coil, 1030*b* is a sense coil, which passively detects changes in the magnetic field produced by the field coils (i.e., via magnetic induction). Accordingly, as metallic particles within fluid 1040*b* travel in direction 1050*b* past the first field coil 1020*b*1, the metallic particles interact with the magnetic field produced by field coil 1020*b*1. This interaction is detected as a change in voltage across the sense coil 1030*b*. As the metallic particles continue to travel in direction 1050*b* past the second field coil 1020*b*2, the metallic particles interact with the magnetic field produced by field coil 1020*b*2. This interaction is detected in an opposite change in voltage across the sense coil 1030*b*.

Figure 22A:
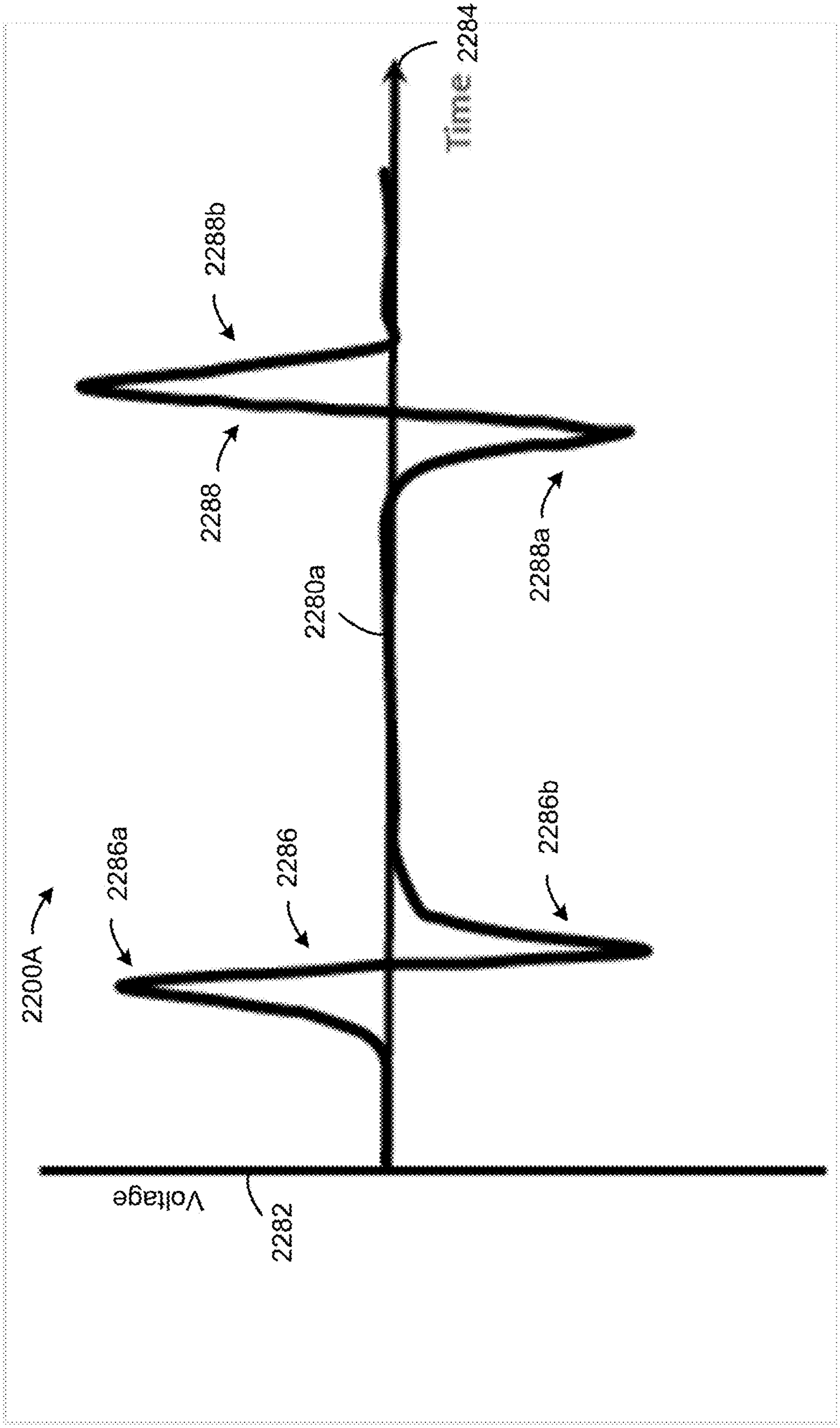
FIG. 22A is an example plot of PCS sensor output as a function of time in accordance with an embodiment.

Referring to FIG. 22A, shown therein is an example plot 2200A of a PCS sensor output as a function of time in accordance with an example embodiment. The example plot 2200A is based on a PCS comprises a first field coil, a sense coil and a second field coil in a field-sense-field (F-S-F) configuration. The y-axis 2282 represents the voltage measured by the sense coil of a PCS sensor. The x-axis 2284 represents time. The data trace 2280*a* can be referred to as a "particle trace" or "trace". As shown in FIG. 22A, the PCS generates distinct peaks 2286 and 2288 over time as particles pass the sensor. For example, peak 2286 represents a ferrous particle passing the PCS, while peak 2288 represents a non-ferrous particle passing the PCS. These distinct peaks 2286 and 2288 allow the fluid monitoring system to distinguish fluid particle signals from noise. For example, each of peaks 2286 and 2288 is "double-lobed" due to the two distinct spikes in the particle trace of each peak that are opposite in polarity. As shown, peak 2286 includes spike (or lobe) 2286*a* and opposite polarity spike (or lobe) 2286*b*. Similarly, peak 2288 includes spike (or lobe) 2288*a* and opposite polarity spike (or lobe) 2288*b*. The double-lobed nature of particle trace 2280*a* distinguishes the sensor signal from noise (e.g., vibration noise), which can appear as single-lobed. In general, the fluid monitoring system can better distinguish a PCS sensor signal from noise when a particle trace has more lobes because the signal band within the frequency domain is narrower for a double-lobed signal than a single-lobed signal, which allows more of the noise (e.g., vibration spectrum) to be filtered out. The PCS design to include two field coils allows the particle trace 2280*a* to have this distinct double-lobed shape.

In some embodiments, the PCS consists of two or more field coils and two or more sense coils in various configurations. For example, in one embodiment, the PCS consists of three field coils and two sense coils in a field-sense-field-sense-field (F-S-F-S-F) configuration. In another embodiment, the PCS consists of four field coils and three sense coils in a field-sense-field-sense-field-sense-field (F-S-F-S-F-S-F) configuration. In some other embodiments, other number of field and sense coils may be used, where the number of field coils is equal to the number of sense coils +1.

In some further embodiments, the PCS consists of one field coil and two sense coils. In some other embodiments, the PCS consists of a number of field coils that is equal to the number of sense coils −1.

Figure 22B:
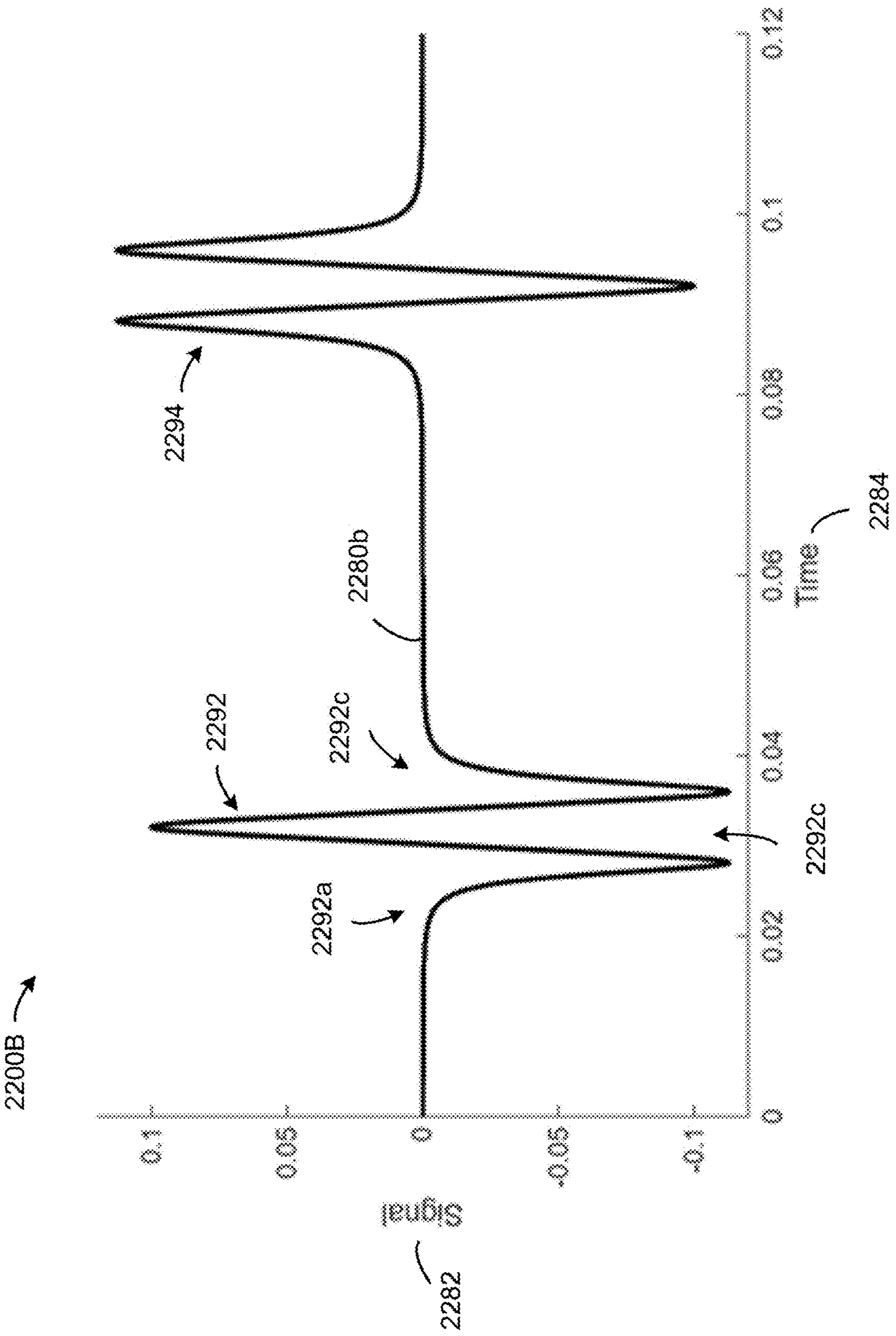
FIG. 22B is an example plot of PCS sensor output as a function of time in accordance with an embodiment.

FIG. 22B illustrates an example plot 2200B of a PCS sensor output as a function of time in accordance with an example embodiment, where the PCS is configured in a F-S-F-S-F configuration. The y-axis 2282 represents the voltage measured by the sense coils of the PCS sensor. The x-axis 2284 represents time. The data or particle trace is illustrated by graph 2280*b*. As shown, the PCS configured in the F-S-F-S-F configuration generates distinct peaks 2292 and 2294 over time as particles pass through the sensor. Each of the peaks 2292 and 2294 is triple-lobed due to three distinct spikes in the particle trace of each peak with opposing polarities. For example, as shown, peak 2292 includes spike 2292*a*, 2292*b* and 2292*c*. Similarly, peak 2294 includes three spikes. The multi-lobed nature of the peak provides the advantage of distinguishing it from noise signal (e.g., vibration noise).

Figure 22C:
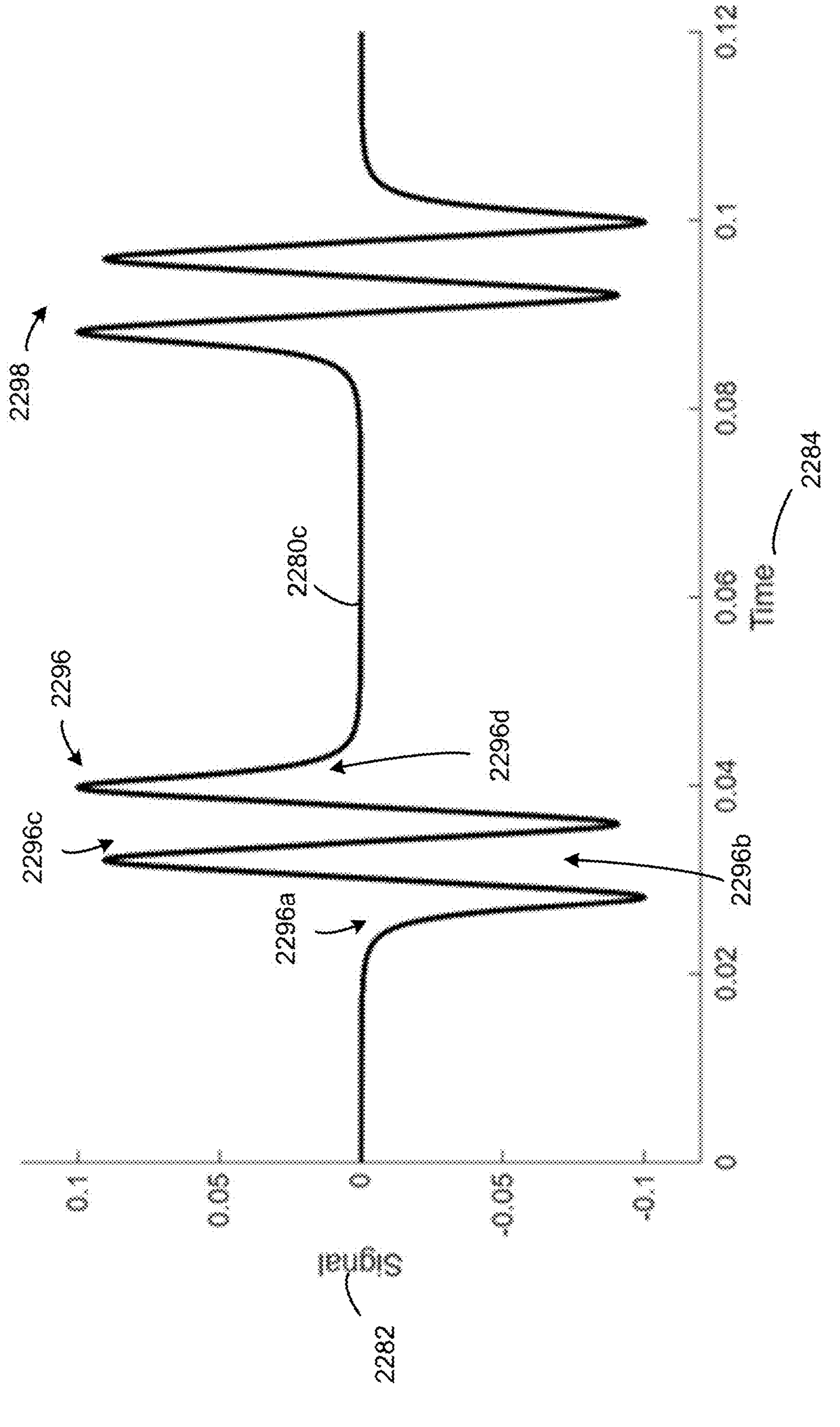
FIG. 22C is an example plot of PCS sensor output as a function of time in accordance with an embodiment.

FIG. 22C illustrates an example plot 2200C of a PCS sensor output as a function of time in accordance with another example embodiment, where the PCS is configured in a F-S-F-S-F-S-F configuration. The y-axis 2282 represents the voltage measured by the sense coils of the PCS sensor. The x-axis 2284 represents time. The data or particle trace is illustrated by graph 2280*c*. As shown, the PCS configured in the F-S-F-S-F configuration generates distinct peaks 2296 and 2298 over time as particles pass through the sensor. Each of the peaks 2296 and 2298 is quadrilobed due to four distinct spikes in the particle trace of each peak with opposing polarities. For example, as shown, peak 2296 includes spike 2296*a*, 2296*b*, 2296*c* and 2296*d*. Similarly, peak 2298 includes four spikes. The multi-lobed nature of the peak provides the advantage of distinguishing it from noise signal (e.g., vibration noise).

Figure 24A:
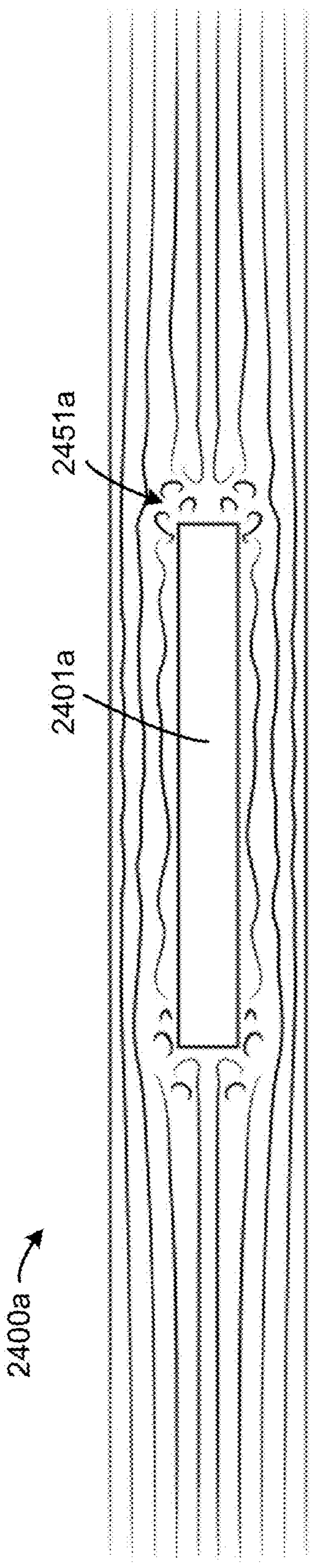
FIG. 24A is an illustration of an example PCS with an unmodified profile in accordance with an embodiment.
Figure 24B:
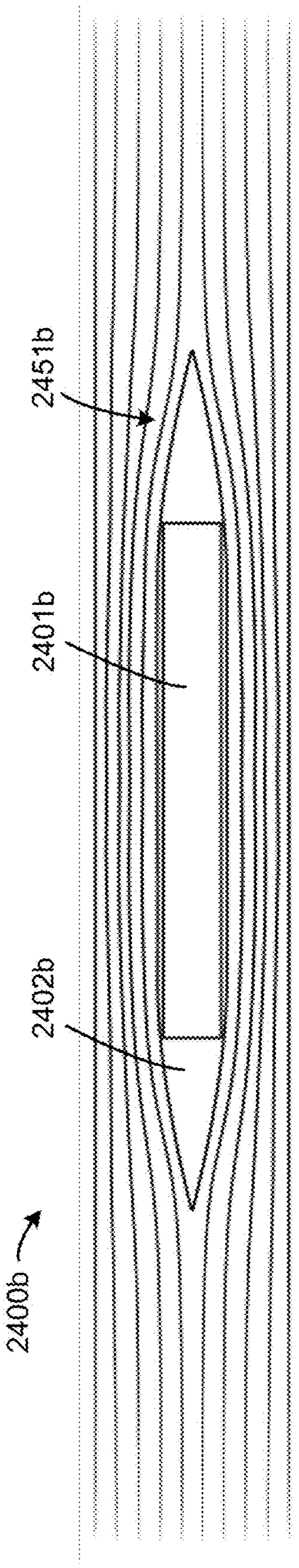
FIG. 24B is an illustration of an example PCS with a hydrodynamic profile in accordance with an embodiment.

Referring now to FIG. 24A, shown therein is an illustration 2400*a* of an example PCS 2401*a*. As shown, the profile of PCS 2401*a* can result in a turbulent flow of fluid 2451*a* around PCS 2401*a*. Referring to FIG. 24B, shown therein is an illustration 2400*b* of an example PCS 2401*b*. PCS 2401*b* can have a hydrodynamic profile 2402*b*, which increases the PCS's ability to detect fluid particles as well as reduces the pressure drop across the PCS. As shown, the hydrodynamic profile 2402*b* can result in a smoother flow of fluid 2451*b* around the PCS 2401*b*. The hydrodynamic profile 2402*b* can be achieved using an epoxy mold. For example, the PCS 2401*b* can include an outer layer comprised of epoxy to provide the hydrodynamic profile 2402*b*. The epoxy can include, for example, Loctite E-60. However, this material is provided as an example only, and other suitable epoxy materials can be used.

Figure 11A:
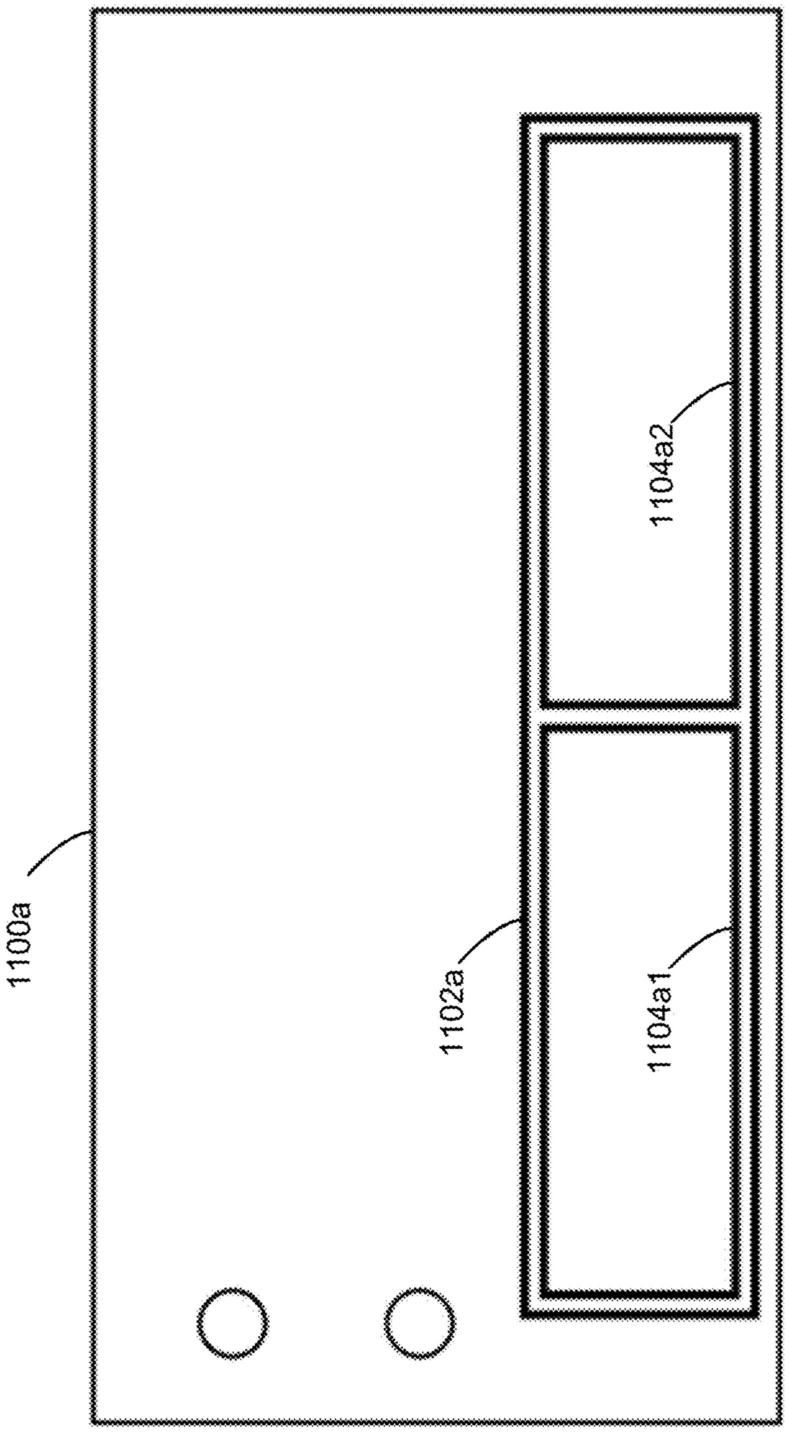
FIG. 11A is an illustration of an example of the PCS of FIG. 10B in accordance with an embodiment.

Referring to FIG. 11A, shown therein is an example PCS 1100*a*. As shown in FIG. 11A, PCS 1100*a* includes a field coil 1102*a* and sense coils 1104*a*1 and 1104*a*2. Each of the field coil 1102*a* and sense coils 1104*a*1 and 1104*a*2 can be printed on n layers of the PCS, where n is an application-specific parameter. For example, n can be selected based on simulations of a given application. The dimensions of PCS 1100*a* can vary depending on the application. For example, the dimensions of PCS 1100*a* can be selected based on the diameter of a pipe in which PCS 1100*a* is to be installed.

Figure 11B:
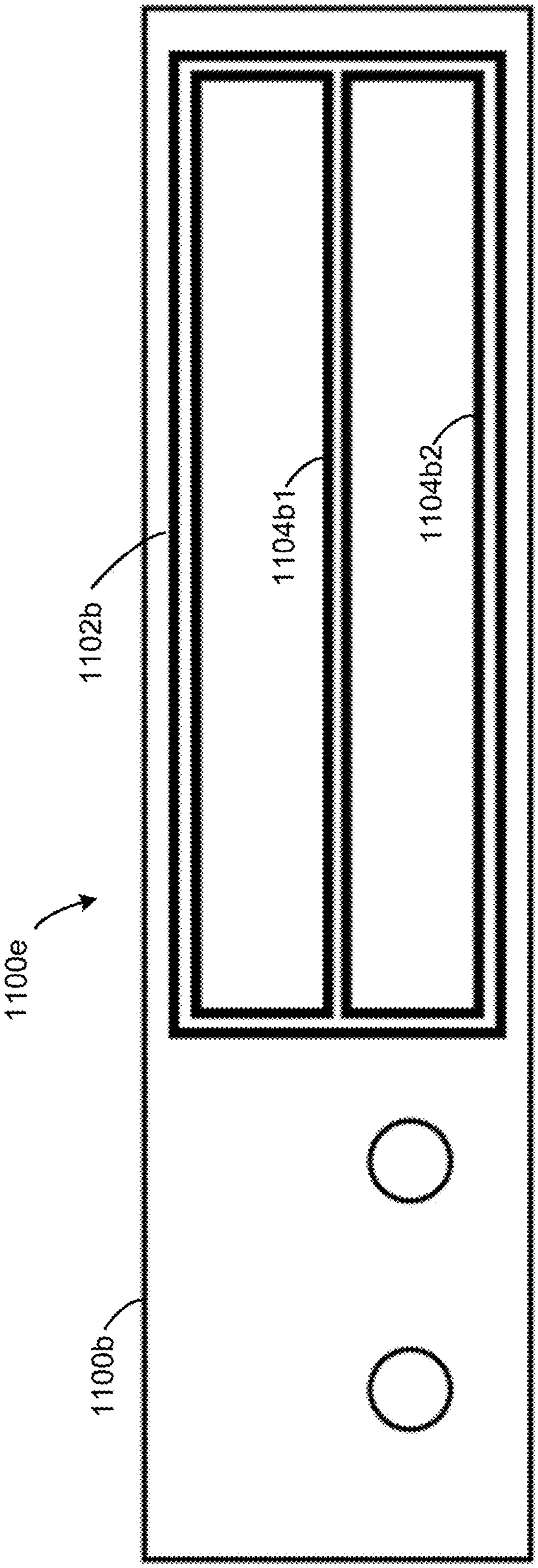
FIG. 11B is an illustration of another example of the PCS of FIG. 10B in accordance with an embodiment.

Referring to FIG. 11B, shown therein is an example PCS 1100*b*. PCS 1100*b* is similar to PCS 1100*a* but with an alternative coil configuration. As shown in FIG. 11B, portion 1100*e* includes field coil 1102*b* and sense coils 1104*b*1 and 1104*b*2. As shown, sense coils 1104*b*1 and 1104*b*2 are symmetric. Each of the field coil 1102*b* and the sense coils 1104*b*1 and 1104*b*2 can be printed on n layers of the PCS, where n is an application-specific parameter. For example, n can be selected based on simulations of a given application. In some embodiments, sense coils 1104*b*1 and 1104*b*2 include a different number of winds and occupy a different number of layers compared to the corresponding field coil 1102*b*. The dimensions of PCS 1100*b* can vary depending on the application. For example, the dimensions of PCS 1100*b* can be selected based on the diameter of a pipe in which PCS 1100*b* is to be installed.

Although FIGS. 11A and 11B illustrate embodiments having one field coil and two sense coils, other embodiments can include one sense coil and two field coils.

Referring to FIG. 12, shown therein is an example PCS 1200. As shown in the example in FIG. 12, PCS 1200 includes two inductive sensors 1210*a* and 1210*b* printed on a single PCB. PCS 1210*a* includes field coils 1220*a*1 and 1220*a*2. PCS 1210*b* includes field coils 1220*b*1 and 1220*b*2. PCS 1200 further includes corresponding sense coils 1230*a* and 1230*b*.

Referring to FIG. 13, shown therein is an example illustration 1300 of an array structure 1360. As shown in FIG. 13, array structure 1360 includes three PCS boards 1301*a*, 1301*b*, and 1301*c*. Array structure 1360 allows for simplified installation of multiple PCS boards. Although the example shown in FIG. 13 shows three PCS boards installed in array structure 1360, any other number of PCS boards can be installed. Although the example shown in FIG. 13 shows the PCS boards 1301*a-c* oriented in a vertical direction, other embodiments can include the PCS boards installed in other orientations, such as horizontal or angled.

Figure 14B:
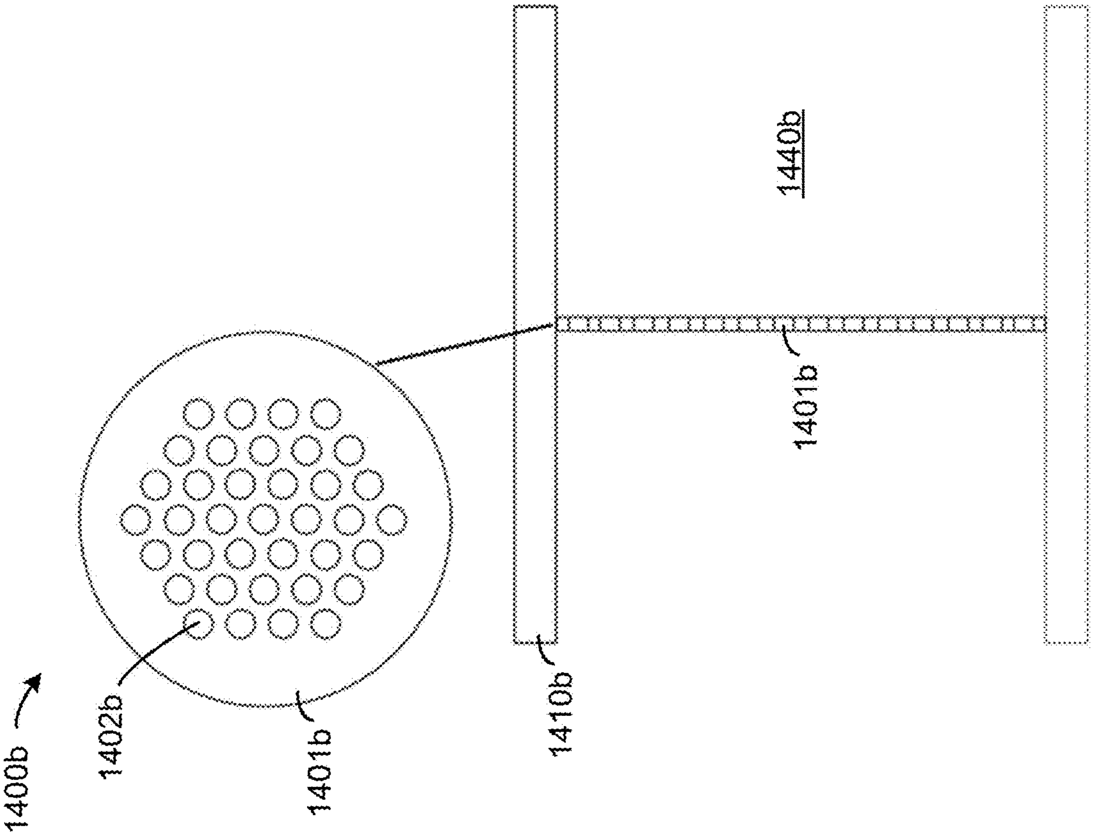
FIG. 14B is an illustration of another example mesh PCS in accordance with an embodiment.
Figure 14A:
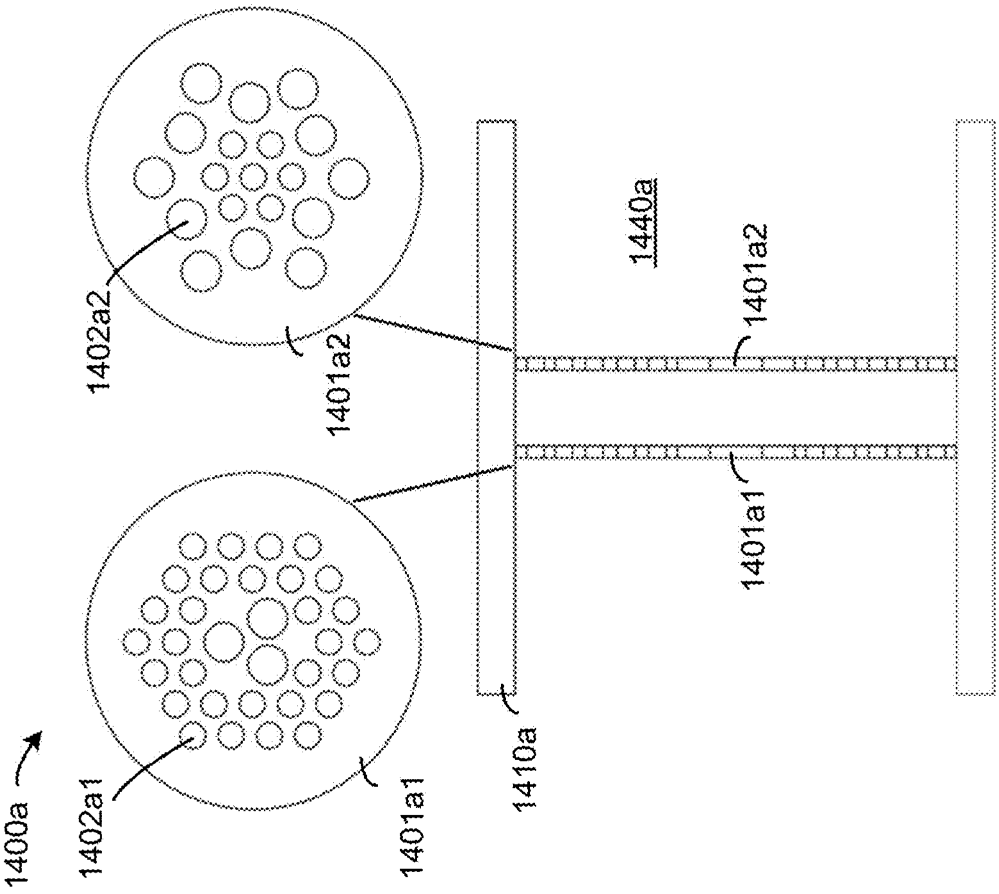
FIG. 14A is an illustration of an example mesh PCS in accordance with an embodiment.

Referring to FIG. 14A, shown therein is an illustration 1400*a* of example PCS boards 1401*a*1 and 1401*a*2. As shown in FIG. 14A, each of PCS boards 1401*a*1 and 1401*a*2 can have a mesh structure with one or more apertures 1402*a*1 and 1402*a*2, respectively, in the face of the PCS board. PCS boards 1401*a*1 and 1401*a*2 can be installed within a pipe 1410*a* such that fluid 1440*a* can flow through one of more of the apertures 1402*a*1 and 1402*a*2 on PCS boards 1401*a*1 and 1401*a*2. In the example shown in FIG. 14A, PCS boards 1401*a*1 and 1401*a*2 have different aperture patterns. In alternative embodiments, PCS boards 1401*a*1 and 1401*a*2 can have the same aperture pattern.

In some embodiments, each mesh sensor comprises a separate PCB for each of a first field coil trace, a second field coil trace and a sense coil trace. In some cases, the separate PCBs are stacked adjacent to one another and in some other cases, the separate PCBs are separated from each other using spacers or other mechanisms. The various PCBs can have a number of opening ranging from one (e.g., one large opening in the center) to any number of openings. In some other examples, the first field coil trace, the second field coil trace and the sense coil trace are all printed on the same PCB.

Referring to FIG. 14B, shown therein is an illustration 1400*b* of an example PCS board 1401*b*. As shown in FIG. 25B, PCS board 1401*b* can have a mesh structure with one or more apertures 1402*b*. PCS board 1401*b* can be installed within a pipe 1410*b* such that fluid 1440*b* flows through one or more of the apertures 1402*b* on PCS board 1401*b*. This sensing principle can be applied to either the entire pipe or to a smaller section of pipe as shown in FIGS. 14D-E. FIG. 14D shows an example mesh PCS 1401*d* that can be applied in a smaller section of pipe 1410*e*, as shown in FIG. 14E.

Figure 14C:
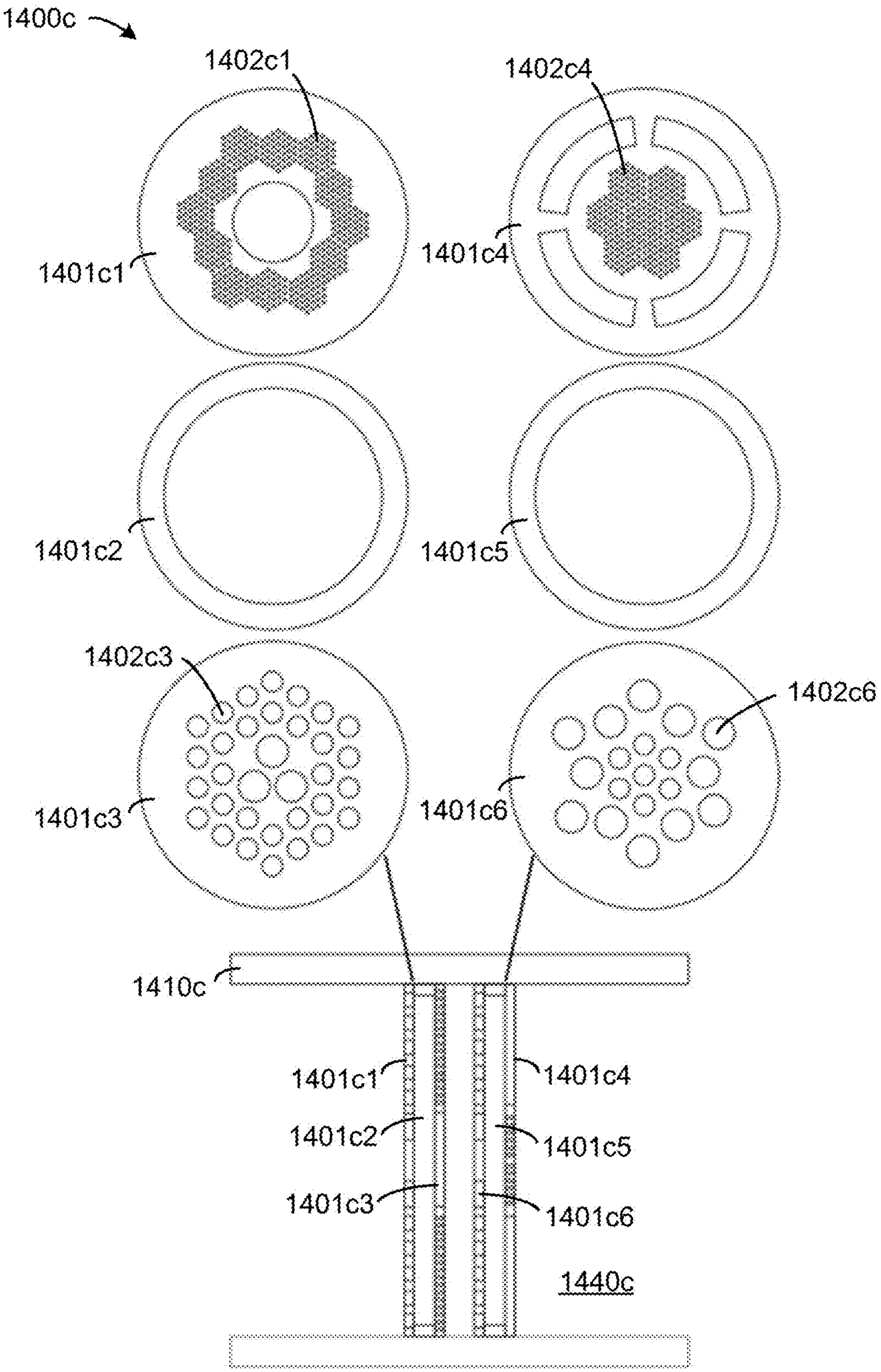
FIG. 14C is an illustration of another example mesh PCS in accordance with an embodiment.
Figure 14E:
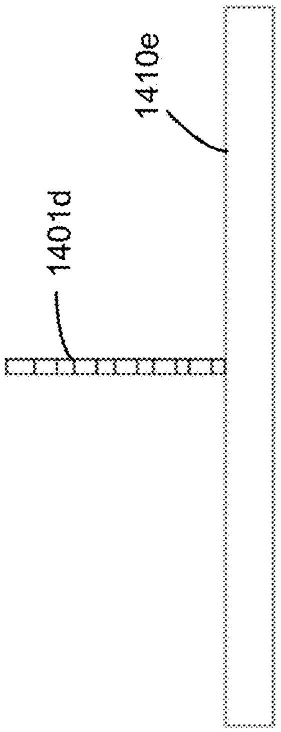
FIG. 14E is an illustration of an example mesh PCS in accordance with an embodiment.
Figure 14D:
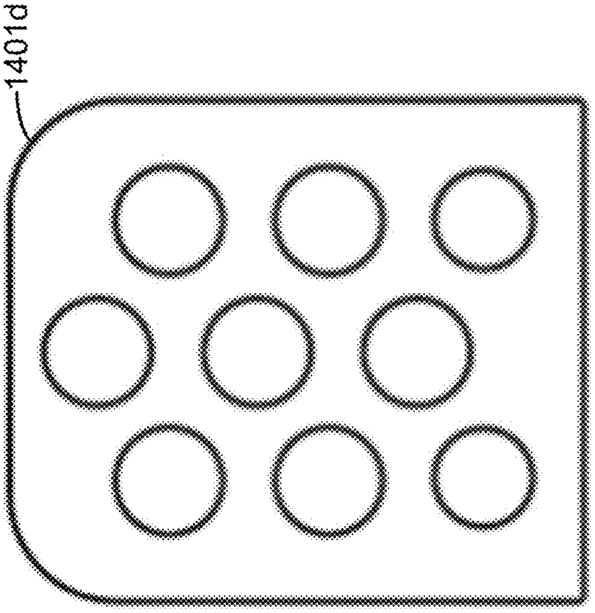
FIG. 14D is an illustration of an example mesh PCS in accordance with an embodiment.

Referring to FIG. 14C, shown therein is an illustration 1400*c* of example PCS boards 1401*c*1, 1401*c*3, 1401*c*4, and 1401*c*6. As shown in FIG. 14C, each of PCS boards 1401*c*1, 1401*c*3, 1401*c*4, and 1401*c*6 can have a unique mesh structure with one or more aperture patterns 1402*c*1, 1402*c*3, 1402*c*4, and 1402*c*6, respectively, in the face of the PCS board. There can further be sensor components 1401*c*2 and 1401*c*5 implemented in a ring pattern, with one single aperture to allow fluid flow. In the example illustrated, components 1401*c*2 and 1401*c*5 are ring-type spacers without any active electrical features. As illustrated, the PCS boards are implemented such that two sub-sensors, spaced apart from each other, are provided in the medium 1440*c*. The first sub-sensor includes the PCS board 1401*c*1, sensor component 1401*c*2 and PCS board 1401*c*3 coupled to each other, such that the sensor component 1401*c*2 installed between the PCB boards 1401*c*1 and 1401*c*3. Similarly, the second sub-sensor includes the PCS boards 1401*c*4 and 1401*c*6 with the sensor component 1401*c*5 installed in between. In some embodiments, each of PCS boards 1401*c*1, 1401*c*3, 1401*c*4, and 1401*c*6 is a standalone PCS including at least three layers, such as two field trace layers and one sense trace layer. PCS boards 1401*c*1-6 can be installed within a pipe 1410*c* such that fluid 1440*c* can flow through one of more of the apertures 1402*c*1, 1402*c*3, 1402*c*4, and 1402*c*6 on PCS boards 1401*c*1, 1401*c*3, 1401*c*4, and 1401*c*6. In the example shown in FIG. 14C, PCS boards 1401*c*1, 1401*c*3, 1401*c*4, and 1401*c*6 have different aperture patterns. In alternative embodiments, PCS boards 1401*c*1, 1401*c*3, 1401*c*4, and 1401*c*6 can have the same aperture pattern.

Figure 14F:
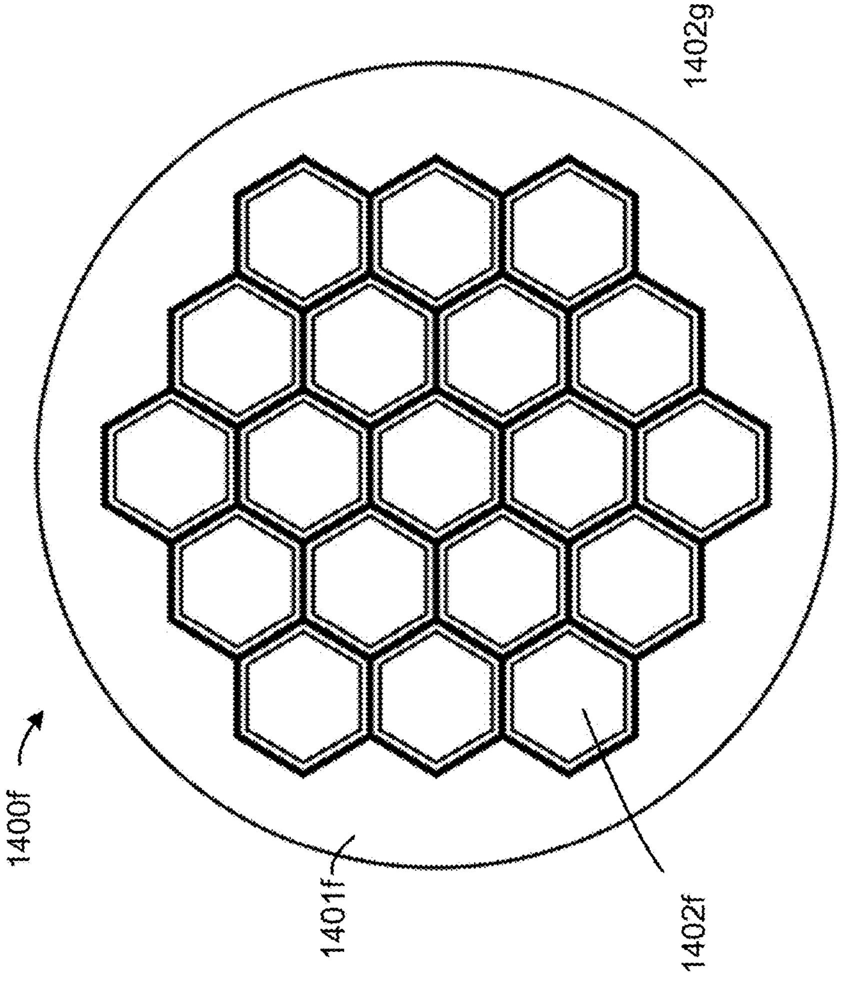
FIG. 14F is an illustration of an example mesh PCS in accordance with an embodiment.
Figure 14G:
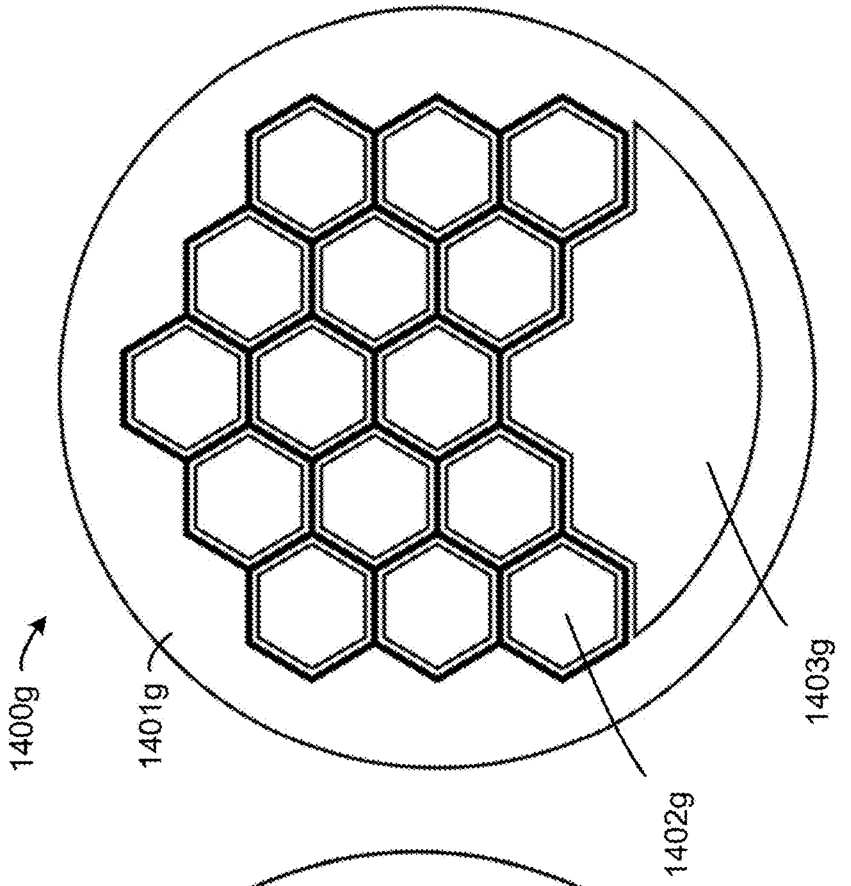
FIG. 14G is an illustration of another example mesh PCS in accordance with an embodiment.

Further challenges with the mesh structure may include a large pressure drop across the large surface area of the mesh, and a potential for the mesh apertures to become clogged. Reference will now be made to FIGS. 14F and 14G. Referring to FIG. 14F, shown therein is an illustration 1400*f* of an example mesh style PCS 1401*f* with one or more apertures 1402*f*. Referring to FIG. 14G, shown therein is an illustration 1400*g* of an example mesh style PCS 1401*g* with one or more apertures 1402*g* and a built-in bypass 1403*g*.

The bypass 1403*g* can both reduce the pressure drop across the surface of the mesh PCS 1401*g* and can provide a path for larger particles to pass through to prevent clogging. Furthermore, in scenarios in which one or more of the apertures 1402*g* do clog, the bypass 1403*g* maintains a lower pressure drop across the PCS 1401*g*.

The pressure drop can be further controlled based on the density of the apertures 1402*f-g*, the thickness of the PCS 1401*f-g*, and the overall diameter of the PCS 1401*f-g*. For example, the size of the apertures 1402*f-g* should be selected to be as large as possible. That is, the size of the apertures 1402*f-g* should be selected to detect particles no smaller than the smallest particle to be detected.

Figure 14H:
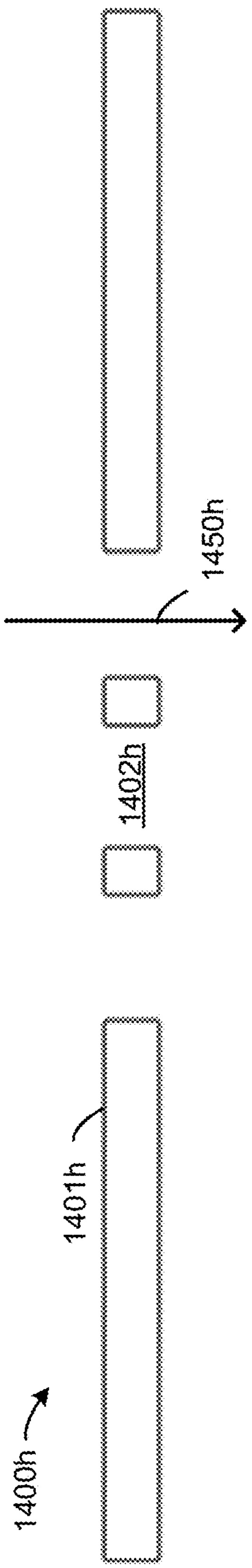
FIG. 14H is a cross-sectional illustration of an example mesh PCS in accordance with an embodiment.
Figure 14I:
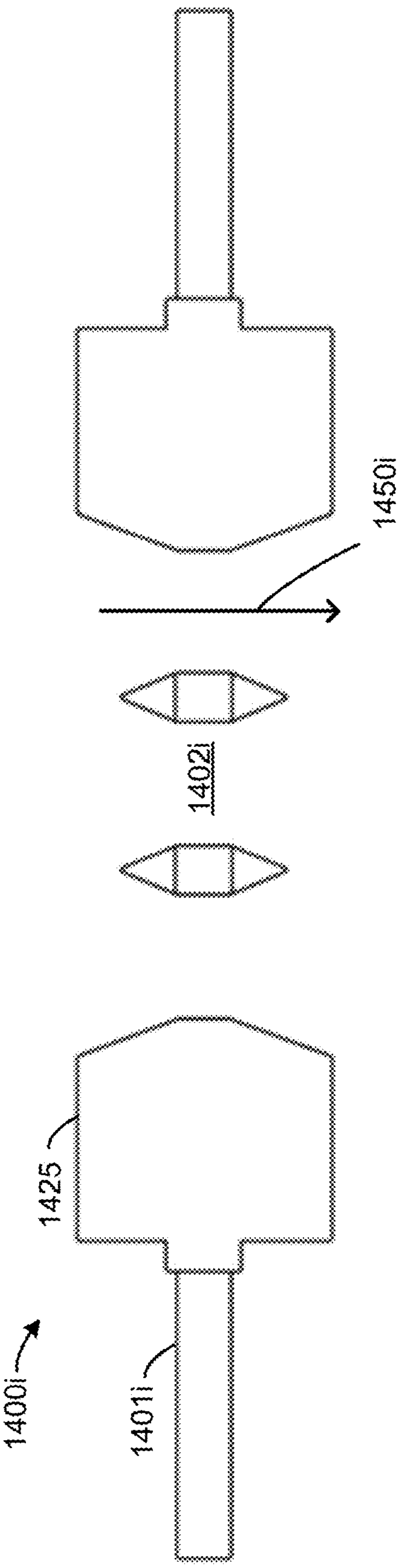
FIG. 14I is a cross-sectional illustration of another example mesh PCS in accordance with an embodiment.

The pressure drop challenge can be further addressed by a flow-conditioning feature. Reference will now be made to FIGS. 14H and 14I. Referring to FIG. 14H, shown therein is a cross-section view illustration 1400*h* of an example mesh PCS 1401*h* with one or more apertures 1402*h*. Fluid flows in direction 2550*h* through one or more of apertures 1402*h*. Referring to FIG. 14I, shown therein is a cross-section view illustration 1400*i* of an example mesh PCS 1401*i* with one or more apertures 1402*i*. Fluid flows in direction 1450*i* through one or more of apertures 1402*i*. As shown in FIG. 14I, mesh PCS 1401*i* has a flow-conditioner 1425. Flow-conditioner 1425 can funnel the flow of fluid in and out of one or more apertures 1402*i*. This funneling action can lower the pressure drop across the mesh PCS 1401*i*.

Figure 14J:
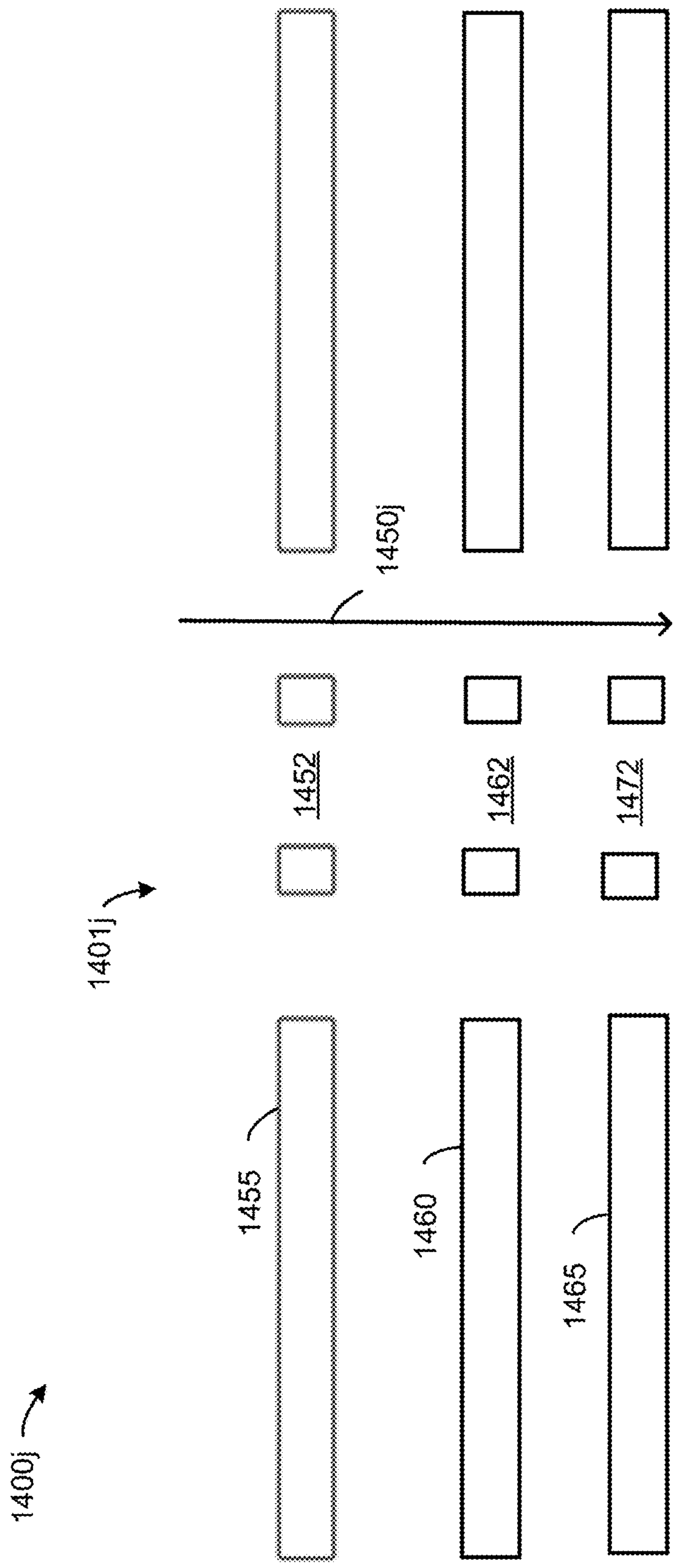
FIG. 14J is a cross-sectional illustration of another example mesh PCS in accordance with an embodiment.

Reference is next made to FIG. 14J, shown therein is a cross-section view illustration 1400*j* of an example mesh PCS 1401*j*. Mesh PCS 1401*j* includes three PCBs, including a first PCB 1455, a second PCB 1460 and a third PCB 1465. First field coil trace is printed on the first PCB 1455, sense coil trace is printed on the second PCB 1460 and the second field coil trace is printed on the third PCB 1465. Each PCB 1455, 1460 and 1465 has one or more apertures, such as apertures 1452 corresponding to first PCB 1455, apertures 1462 corresponding to second PCB 1460 and apertures 1472 corresponding to third PCB 1465. Fluid flows in direction 1450*j* through one or more of apertures 1452, 1462, 1472.

In various embodiments disclosed herein, each individual set of coils may be configured to be either parallel or in series. For example, in the parallel configuration, each individual coil triplet, such as, for example, the first field coil on the first PCB 1455, the sense coil on the second PCB 1460, and the second field coil on the third PCB 1465 is an independent sensing element and all the sensing elements are configured in parallel achieving individual detection of the particles. In the series configuration, all field coils on the first PCB 1455 are electrically connected to form a single distributed coil, all sense coils on the second PCB 1460 are electrically connected to form a single distributed coil, and all the field coils on the third PCB 1465 are similarly connected to form a single distributed coil.

A further challenge with the PCS structures disclosed herein, such as, for example, the mesh structure is that it must be tolerant to fluid exposure. For example, when the fluid being monitored includes lubricant oil, the mesh PCS must be tolerant to the lubricant oil. This can be achieved by using PCB materials that are chemically inert, such as polyamide. Polyamide also reduces thermal stresses on the PCB that could cause delamination as well as reducing stresses on the copper vias that connect the layers of the PCB.

Figure 30A:
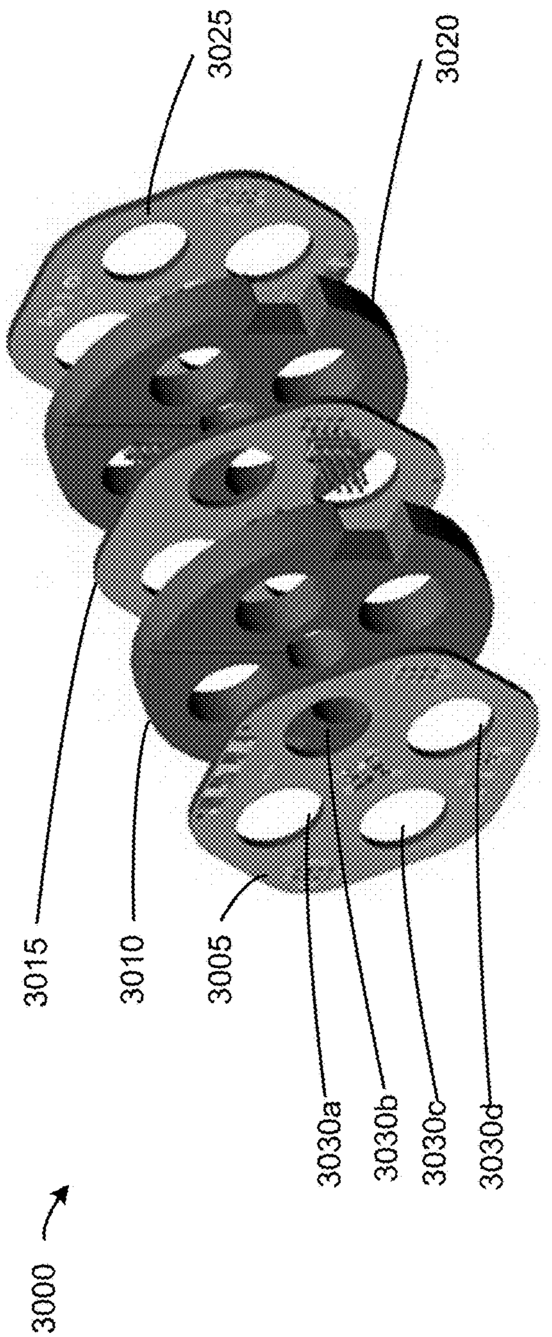
FIG. 30A is an illustration of an example mesh PCS in accordance with an embodiment.

Reference is next made to FIG. 30A, which illustrates an example embodiment of a PCS 3000. PCS 3000 includes a first PCB 3005, a first spacer 3010, a second PCB 3015, a second spacer 3020 and a third PCB 3025. In the illustrated embodiment, the first PCB 3005 is a first field PCB with four coils, the second PCB 3015 is a sense PCB with four coils, and the third PCB 3025 is a second field PCB with four coils.

As shown, the various PCBs and spacers of PCS 3000 include apertures that are aligned. For example, in the illustrated embodiment, the first PCB 3005 has four apertures, namely a first aperture 3030*a*, a second aperture 3030*b*, a third aperture 3030*c* and a fourth aperture 3030*d*. Similarly, the first spacer 3010, the second PCB 3015, the second spacer 3020 and the third PCB 3025, each have four apertures that are aligned with the apertures 3030*a*-3030*d* of the first PCB 3005. The apertures allow the fluid to pass through the PCS 3000.

Figure 30B:
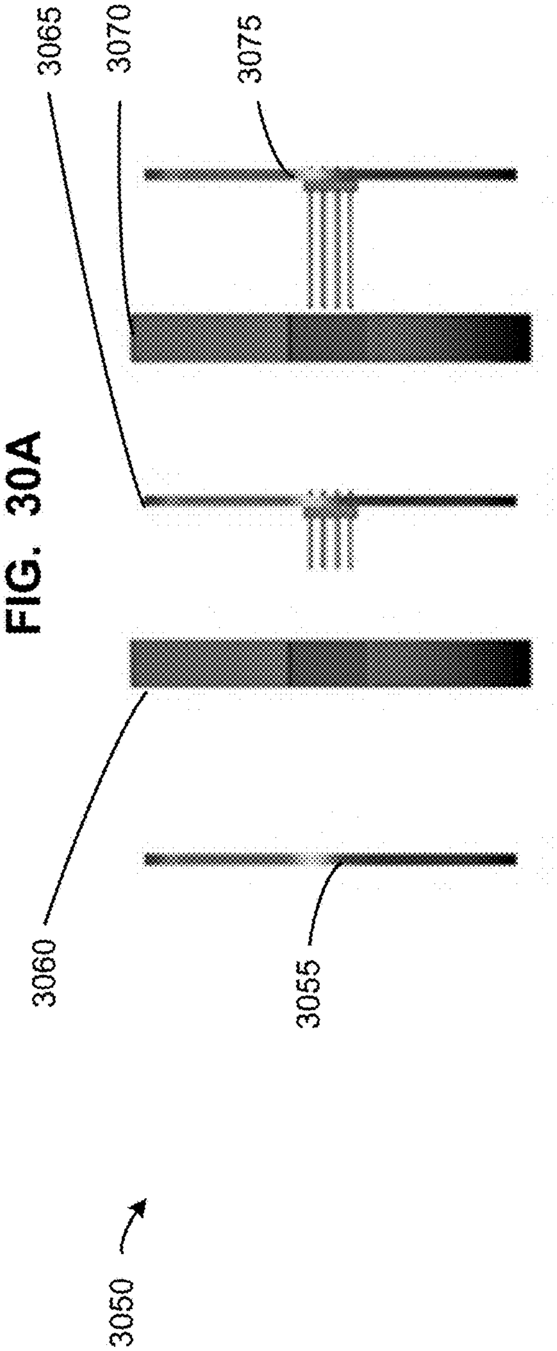
FIG. 30B is an illustration of an example mesh PCS in accordance with another embodiment.

Reference is next made to FIG. 30B, which represents a side view 3050 of PCS 3000 in accordance with an example embodiment. As illustrated, component 3055 is a side view of the first PCB 3005, component 3060 is a side view of the first spacer 3010, component 3065 is a side view of the second PCB 3015, component 3070 is a side view of the second spacer 3020 and component 3075 is a side view of the third PCB 3025.

Figure 30C:
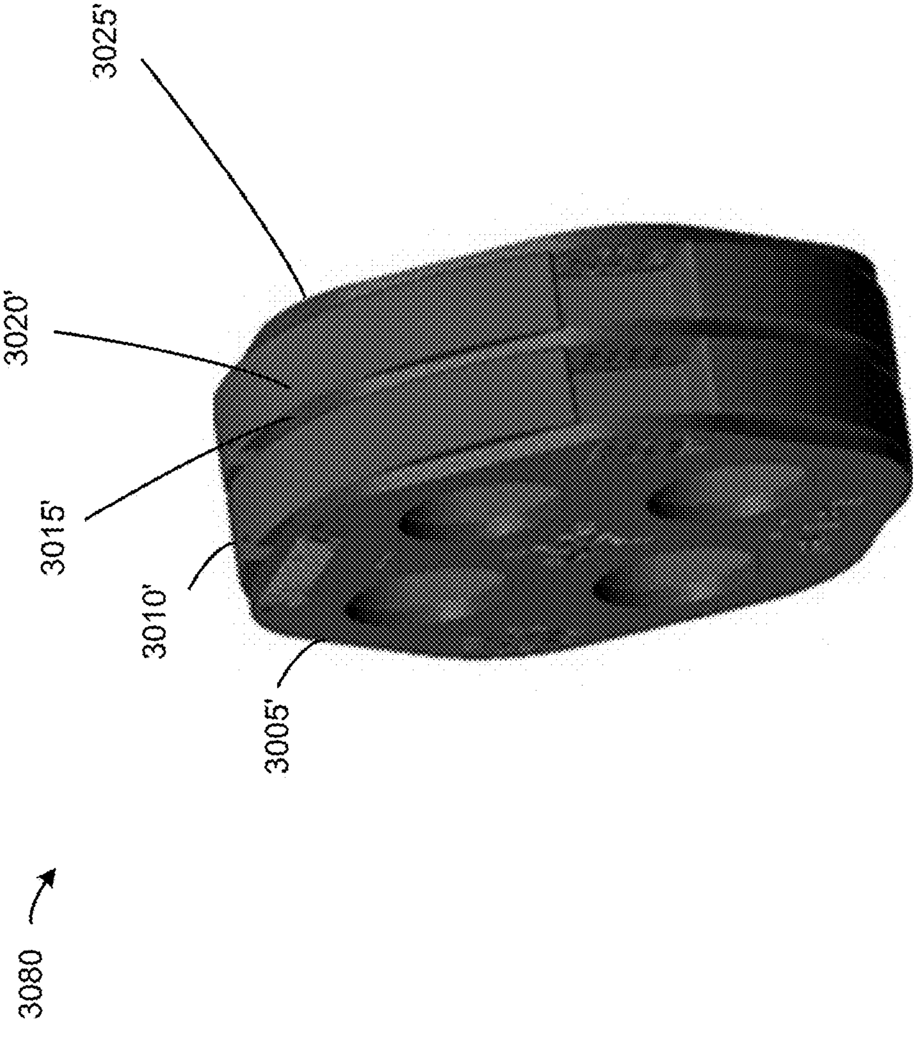
FIG. 30C is an illustration of an example mesh PCS in accordance with a further embodiment.

Reference is next made to FIG. 30C, which illustrates an assembled configuration 3080 of PCS 3000 in accordance with an example embodiment. In the illustrated embodiment, the assembled configuration 3080 results from the bonding of the first PCB 3005', first spacer 3010', second PCB 3015', second spacer 3020' and third PCB 3025'. In some embodiments, the PCBs and spacers are bonded together with an adhesive to form a unified laminated assembly.

Figure 31A:
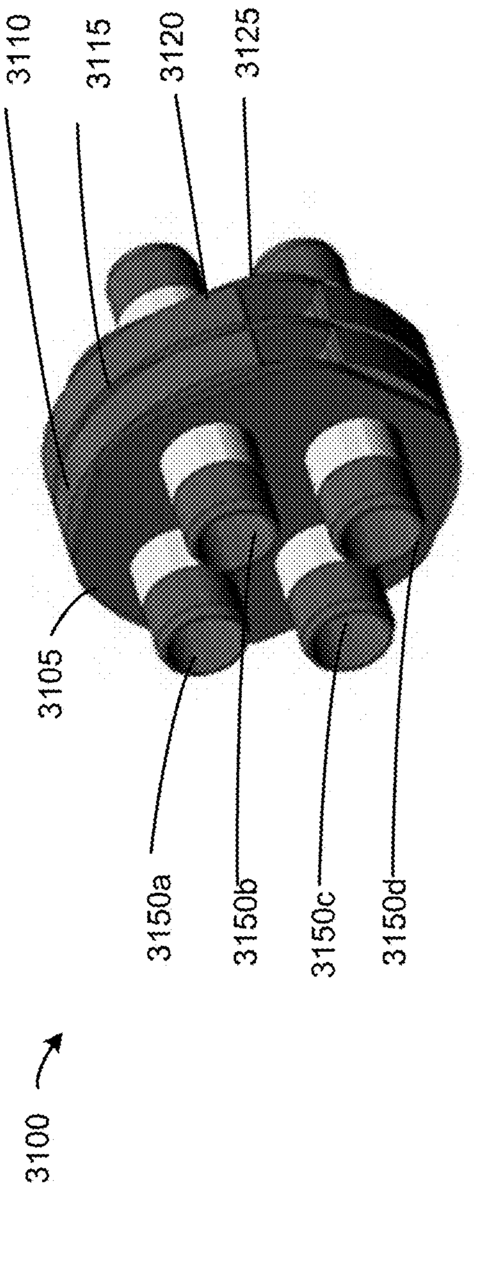
FIG. 31A is an illustration of an example mesh PCS in accordance with an embodiment.

Reference is next made to FIGS. 31A and B, which illustrate a PCS 3100 in accordance with an example embodiment. In the illustrated embodiment, the PCS 3100 is analogous to PCS 3000 of FIG. 30A, with the additional inclusion of oil containment tubes (OCTs).

FIG. 31A illustrates an assembled configuration of a PCS, which includes a first PCB 3105, a first spacer 3110, a second PCB 3115, a second spacer 3120 and a third PCB 3125. Similar to PCS 3000 of FIG. 30A, the first PCB 3105 is a first field PCB with four coils, the second PCB 3115 is a sense PCB with four coils, and the third PCB 3125 is a second field PCB with four coils.

PCS 3100 further includes four OCTs, namely a first OCT 3150*a*, a second OCT 3150*b*, a third OCT 3150*c* and a fourth OCT 3150*d*. OCTs 3150*a-d* are shown in an assembled configuration, where the OCTs are inserted in the apertures of the first PCB 3105, the first spacer 3110, the second PCB 3115, the second spacer 3120 and the third PCB 3125, where the apertures are all aligned with each other. The OCTs provide the advantage of sealing off the PCBs and spacers from the fluid by providing a clear pathway for the fluid to pass through the apertures without coming into contact with the PCBs and spacer materials. In such configurations, no coating is required to seal the gaps between the PCBs and spacers, which may wear off over time anyways and may need to be reapplied.

In various embodiments, the number of OCTs required is directly proportional to the number of coils on each PCB, such as the first PCB 3105, the second PCB 3115 and the third PCB 3125. For example, in the illustrated embodiment four OCTs are used as there are four coils on each PCB, such as the first PCB 3105, the second PCB 3115 and the third PCB 3125.

Figure 31B:
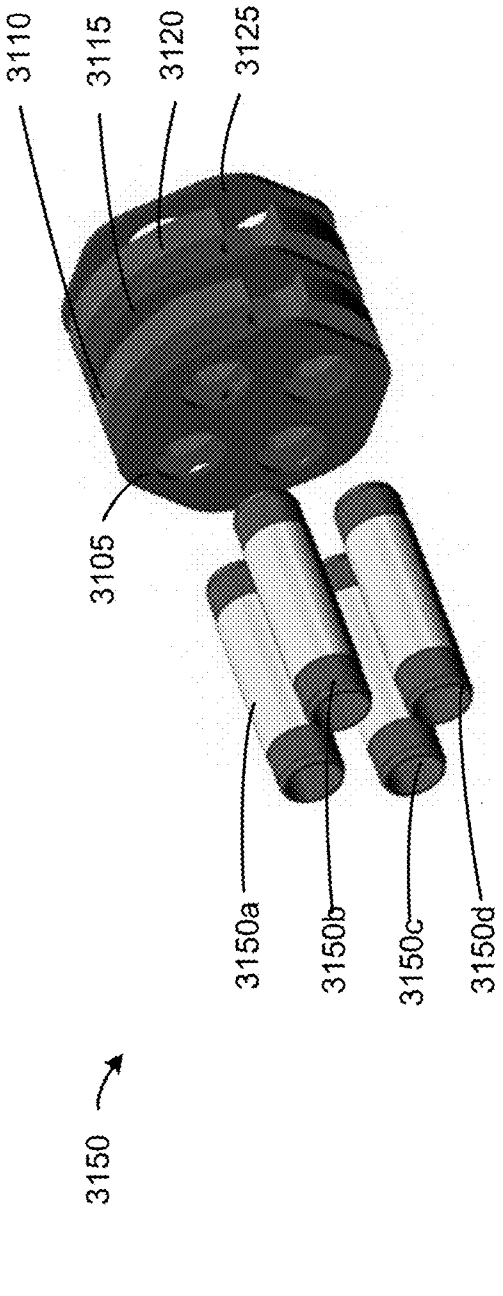
FIG. 31B is an illustration of an example mesh PCS in accordance with another embodiment.

Reference is next made to FIG. 31B, which illustrates an unassembled configuration 3150 of a PCS, such as PCS 3100. As shown, the four OCTs 3150*a*-3150*d* are in an unassembled state with the various PCBs and spacers of the PCS.

Figure 31C:
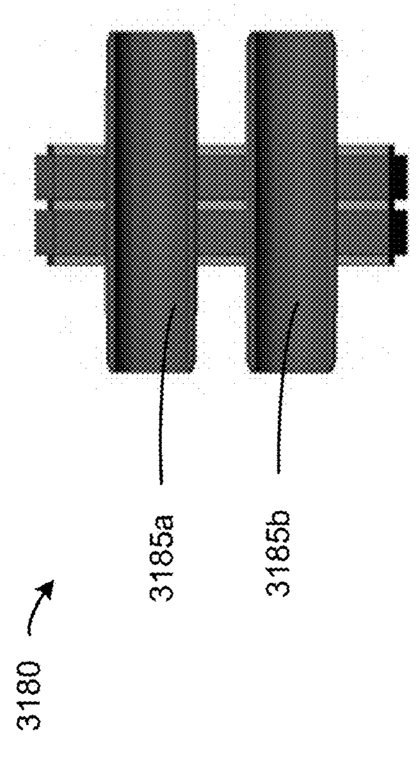
FIG. 31C is an illustration of an example mesh PCS in accordance with a further embodiment.

Reference is now made to FIG. 31C, which illustrates a cross-sectional view 3180 of the assembled PCS, such as PCS 3100. As shown in the cross-sectional view 3180, the OCTs, such as the first OCT 3185*a* and the second OCT 3185*b*, for a sealed fluid path.

Figure 32A:
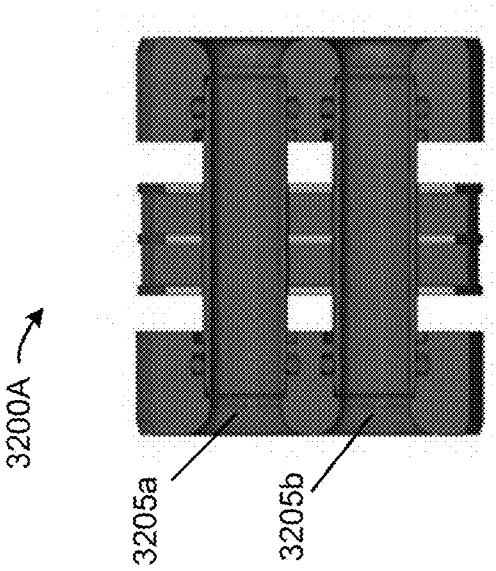
FIG. 32A is an illustration of an example mesh PCS in accordance with an embodiment.
Figure 32B:
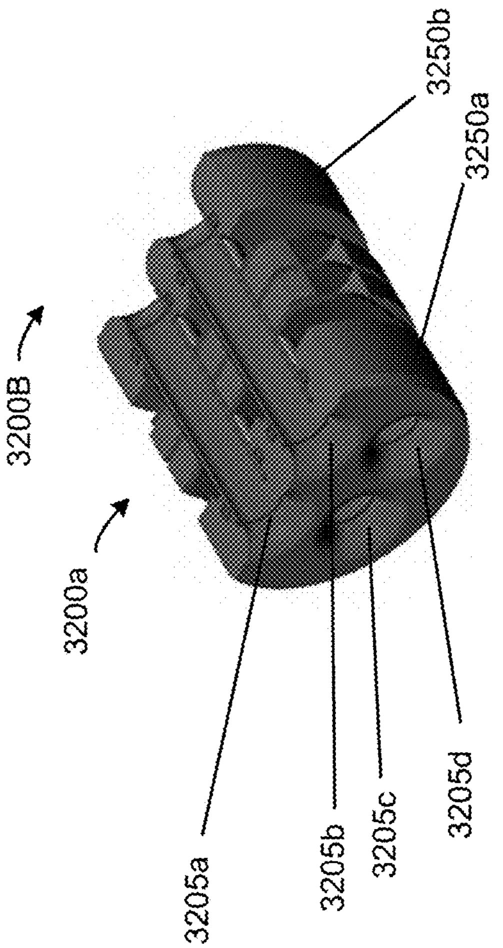
FIG. 32B is an illustration of an example mesh PCS in accordance with another embodiment.

Reference is next made to FIGS. 32A-32B, which illustrate cross-sectional views 3200A, 3200B of the assembled PCS, such as PCS 3100. In particular, FIG. 32A shows the top cross-sectional view 3200*a* of the PCS embodiment shown in FIG. 32B. FIGS. 32A and 32B illustrate a bell-mouth implementation of the apertures, such as a first bell-mouth aperture cross-section 3205*a*, and a second bell-mouth aperture cross-section 3205*b*. FIG. 32B also illustrates a third bell-mouth aperture 3205*c* and a fourth bell-mouth aperture 3205*d*.

As shown, in the bell-mouth implementation, the PCS, such as PCS 3100, is coupled to a guiding structure 3250*a*, 3250*b*, and the guiding structure has guiding apertures, each of which have a curved shape. For example, the guiding structure 3250*a* has curved-shaped apertures 3205*a*-3205*d*. The curved shape of the apertures guides the fluid into the sensing pathways of the mesh sensor PCS in a manner that minimizes the fluid resistance when the fluid is being compressed into the fluid channels, formed by the OCTs, of the PCS. The further minimizes the pressure drop and, accordingly, minimizes the negative impact on the monitored device or equipment.

Figure 15A:
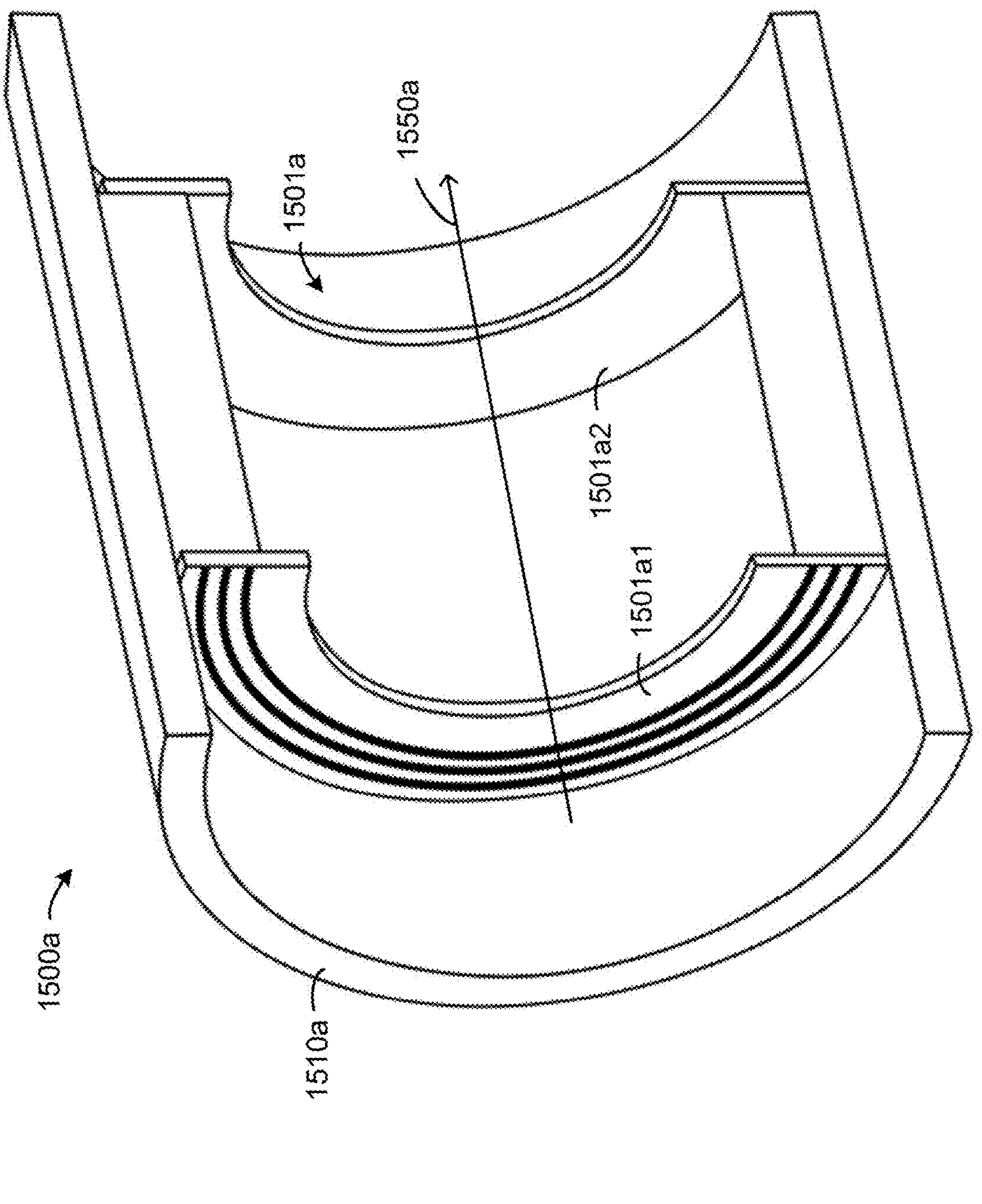
FIG. 15A is an illustration of an example split-printed circuit board (PCB) PCS in accordance with an embodiment.

Reference is next made to FIG. 15A, shown therein is an illustration 1500*a* of a split-PCB PCS 1501*a* installed in pipe 1510*a* with fluid flowing in direction 1550*a*. As shown, the split-PCB PCS 1501*a* includes two PCBs 1501*a*1 and 1501*a*2.

Each PCB 1501*a*1 and 1501*a*2 includes a field coil and a sense coil printed onto several layers of each respective PCB. In some embodiments, the field coil and the sense coil on each PCB 1501*a*1 and 1501*a*2 is wound together in a concentric manner. In the illustrated example, the split-PCB PCS 1501*a* is connected as a split-coil sensor because each PCB 1501*a*1 and 1501*a*2 includes a sense coil as well as a field coil.

In some embodiments, each of the field coils and the sense coil is printed on a separate PCB. In some embodiments, multiple split-PCBs, similar to PCB 1501*a*1, 1501*a*2, are installed in pipe 1510*a* with fluid flowing in direction 1550*a*.

In some embodiments, the signal from the sense coil on each of PCB, such as PCBs 1501*a*1 and 1501*a*2, can be measured independently, i.e. in parallel. In some other embodiments, the sense coils on each of PCB, such as PCBs 1501*a*1 and 1501*a*2, are connected in series together. In both embodiments, PCS 1501*a* can operate as an independent-coil sensor.

Figure 15B:
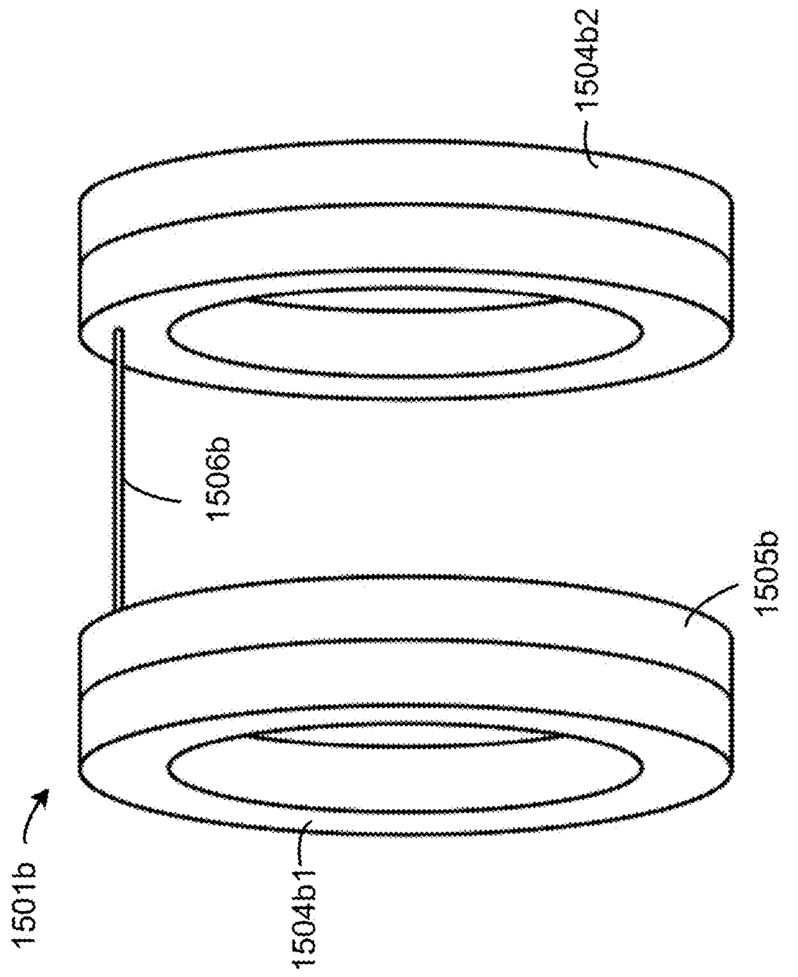
FIG. 15B is an illustration of an example split-PCB PCS in accordance with an embodiment.

Referring to FIG. 15B, shown therein is an illustration of an example split-PCB PCS 1501*b*. The split-PCB PCS 1501*b* includes two field coils 1504*b*1 and 1504*b*2 and a single sense coil 1505*b*. The splitting of the sense coil can be done by using 2 or more sense coils. As shown, the separated winds of sense coil 1505*b* are connected by wind 1506*b*.

Figure 15C:
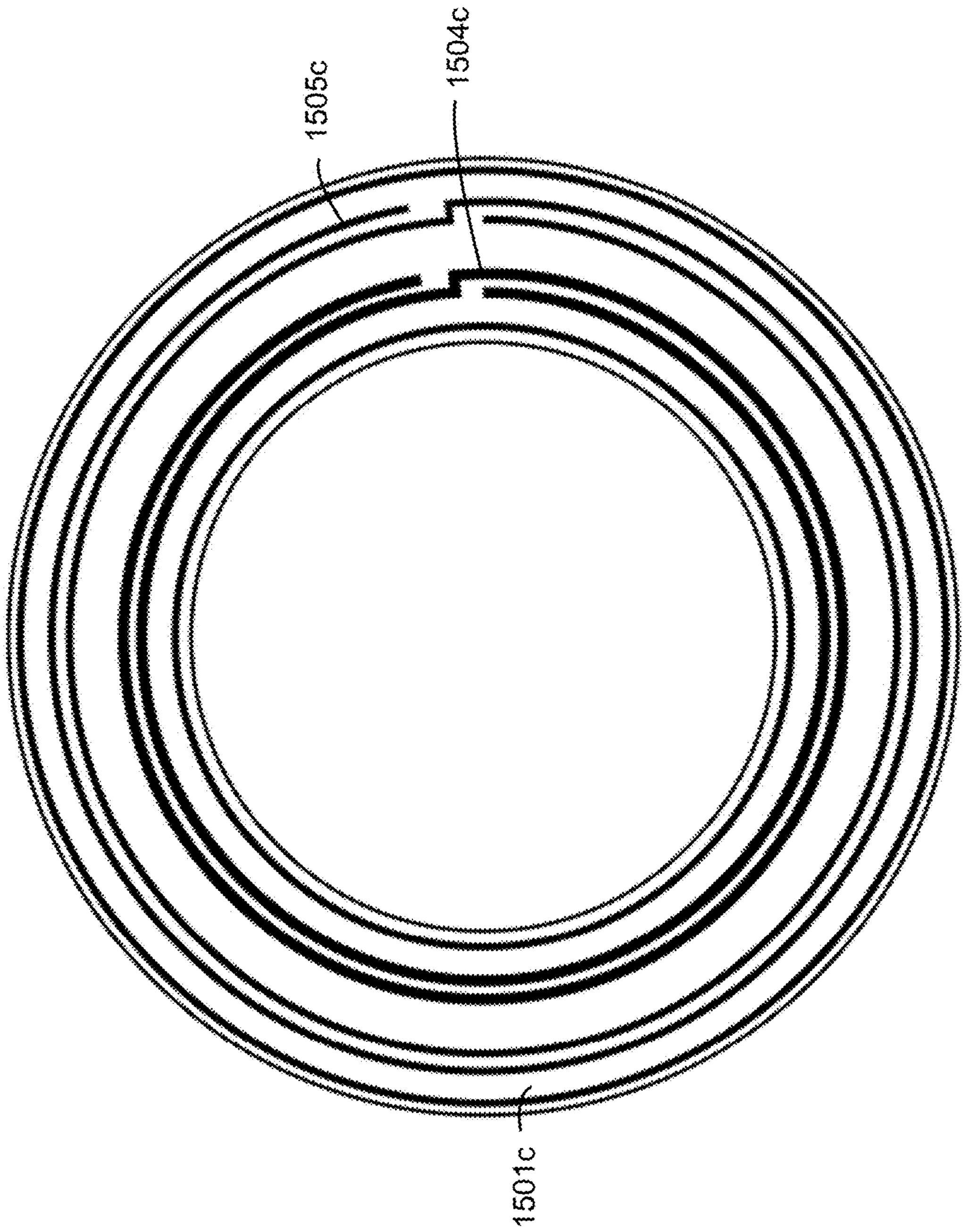
FIG. 15C is an example PCB of a split-PCB PCS in accordance with an embodiment.

Referring to FIG. 15C, shown therein is an example PCB 1501*c* of a split-PCB PCS. As shown, the PCB 1501*c* includes sense coil 1505*c* wound concentrically with field coil 1504*c*. In the illustrated embodiment, the width of sense coil trace 1505*c* is different from the width of field coil trace 1504*c*. That is, the field coil trace 1504*c* is wider than the sense coil trace 1505*c* because the field coil is more sensitive to resistance. As shown, the radial position of sense coil 1505*c* and field coil 1504*c* windings is held constant where possible for each given winding until point at which a given winding steps to the subsequent winding.

Figure 15E:
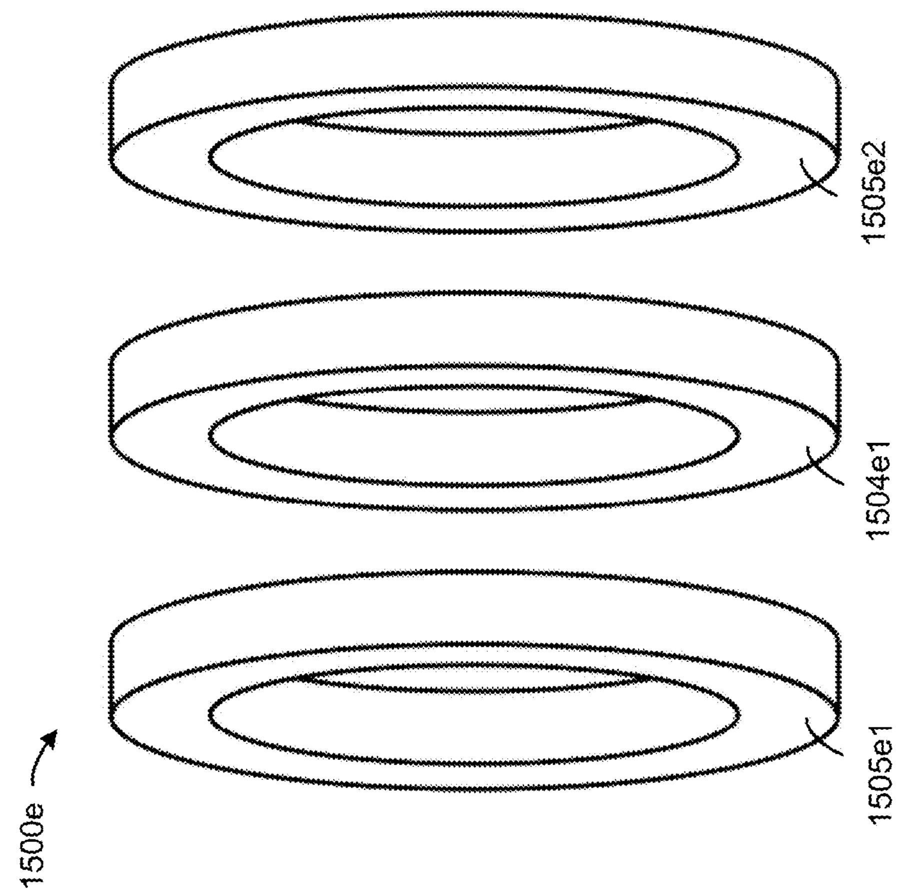
FIG. 15E is an illustration of another example coil arrangement in accordance with an embodiment.
Figure 15D:
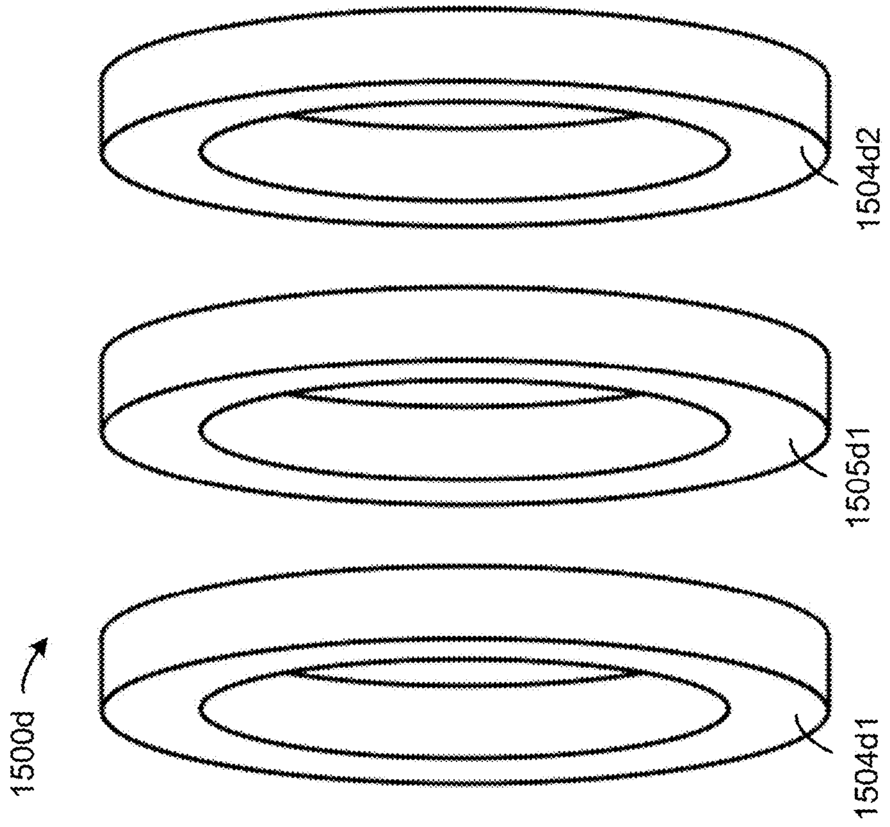
FIG. 15D is an illustration of an example coil arrangement in accordance with an embodiment.

Referring to FIG. 15D, shown therein is an illustration 1500*d* of an example three coil embodiment in a field coil-sense coil-field coil arrangement. In particular, the illustrated embodiment includes field coils 1504*d*1 and 1504*d*2 on either side of sense coil 1505*d*1.

Referring to FIG. 15E, shown therein is an illustration 1500*e* of an example three coil embodiment in a sense coil-field coil-sense coil arrangement. In particular, the illustrated embodiment includes sense coils 1505*e*1 and 1505*e*2 on either side of field coil 1504*e*1. The illustrated embodiment can be operated as an independent-coil sensor, in which the signals from each of sense coils 1505*e*1 and 1505*e*2 are measured independently. Any two-or-more sense-coil sensor configuration can be wired and monitored independently such that the two or more individual sense signals can either be recombined into a standard single channel output, or can be used for common-mode rejection of vibration noise.

Figure 16A:
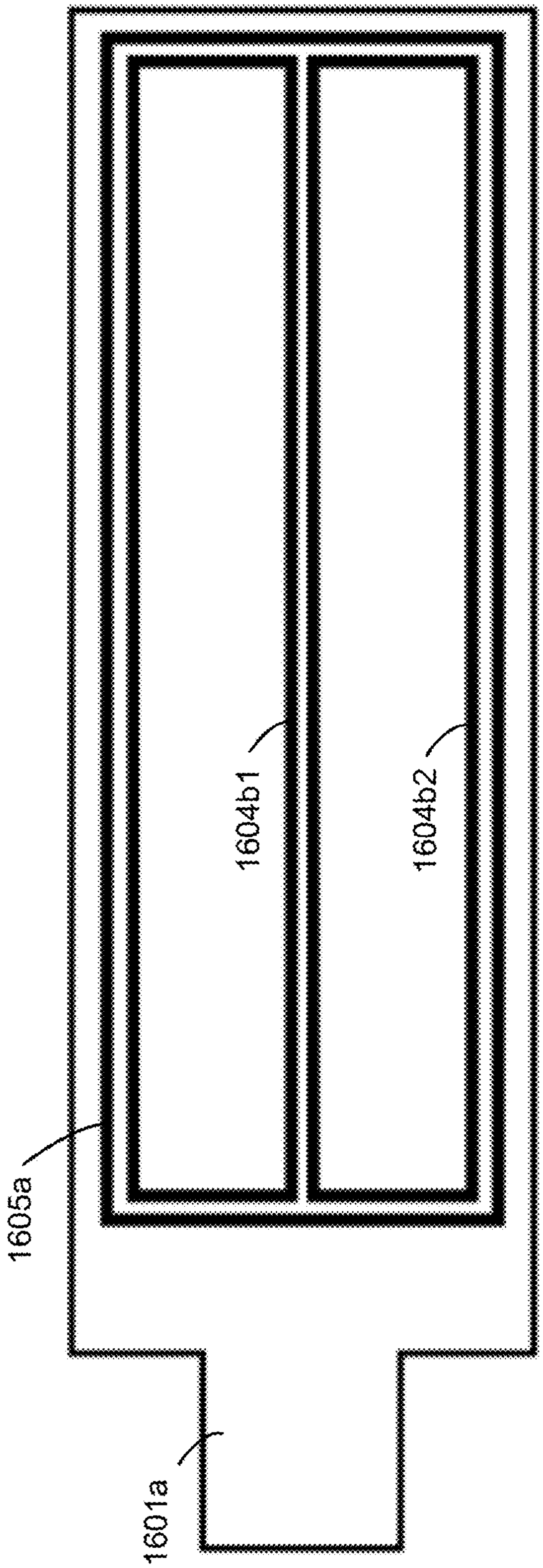
FIG. 16A is an example PCS in accordance with an embodiment.

Referring to FIG. 16A, shown therein is an example PCS 1601*a*. As shown in the example in FIG. 16A, PCS 1601*a* includes sense coil 1605*a* and field coils 1604*b*1 and 1604*b*2. PCS 1601*a* may be similar to PCS 1600*b*, however, PCS 1601*a* is printed on a flexible PCB rather than a traditional, rigid PCB. For example, the flexible PCB can include a flexible polyamide membrane.

Figure 16B:
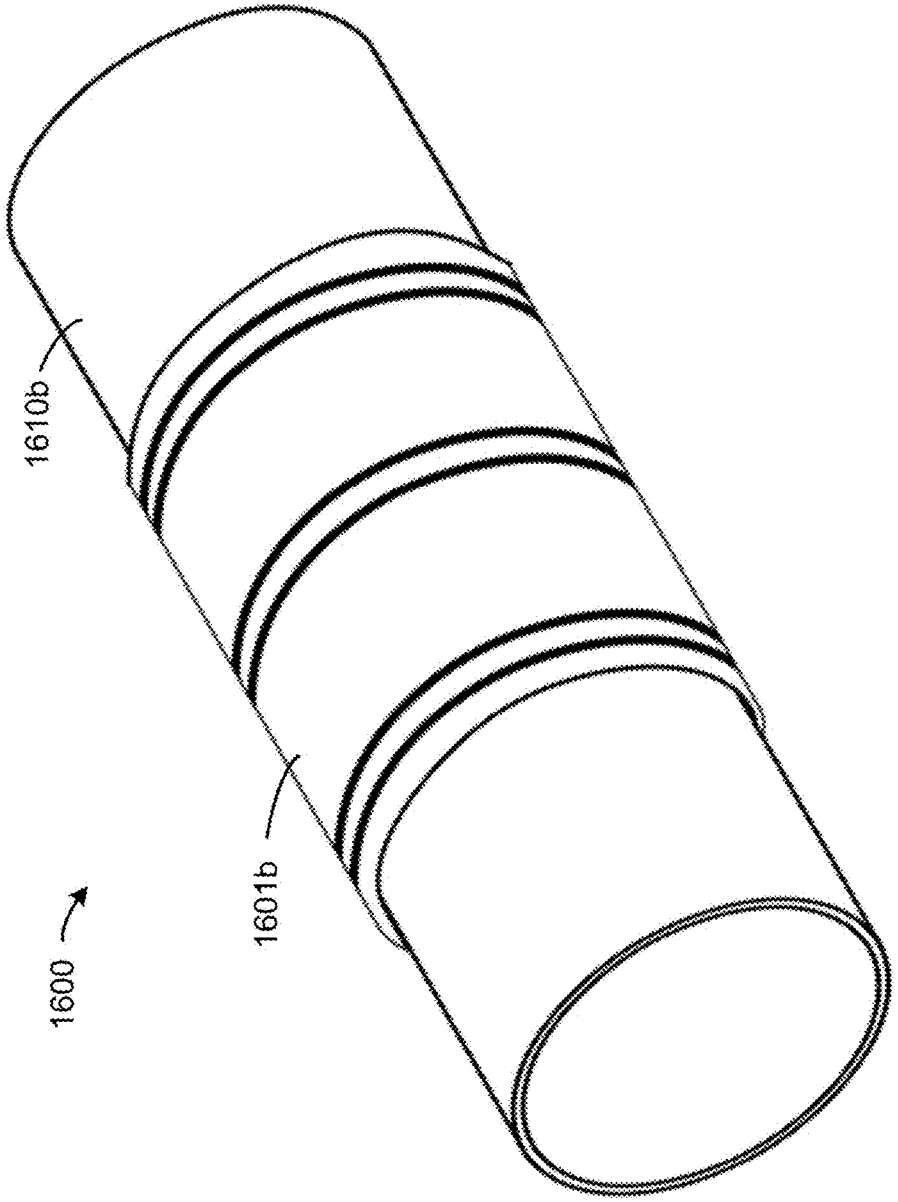
FIG. 16B is an illustration of the example PCS of FIG. 16A in accordance with an embodiment.

Referring to FIG. 16B, shown therein is an illustration 1600 of an example PCS 1601*b* wrapped around a pipe 1610*b*. PCS 1601*b* comprises a flexible PCB, such as a PCS 1601*a*. The positioning of PCS 1601*b* can cause PCS 1601*b* to have sensor properties that are more similar to a flow-through sensor, such as flow-through debris monitoring sensor 1601*a*, than a PCS, such as PCS 1601*b*.

Referring to FIG. 17, shown therein is an illustration 1700 of an example double-D PCS 1701. As shown, double-D PCS 1701 includes field coils 1704*a* and 1704*b* and sense coil 1705. When the double-D PCS 1701 is submerged in the fluid to be monitored, the fluid can flow through apertures 1709*a* and/or 1709*b*. In some embodiments, the form factor of double-D PCS 1701 is smaller than that of a flow-through debris monitoring sensor, such as sensor 1701*a*.

In some embodiments, the two "D" shaped coils can include sense coils, while the single outer coil can include a field coil.

Figure 18:
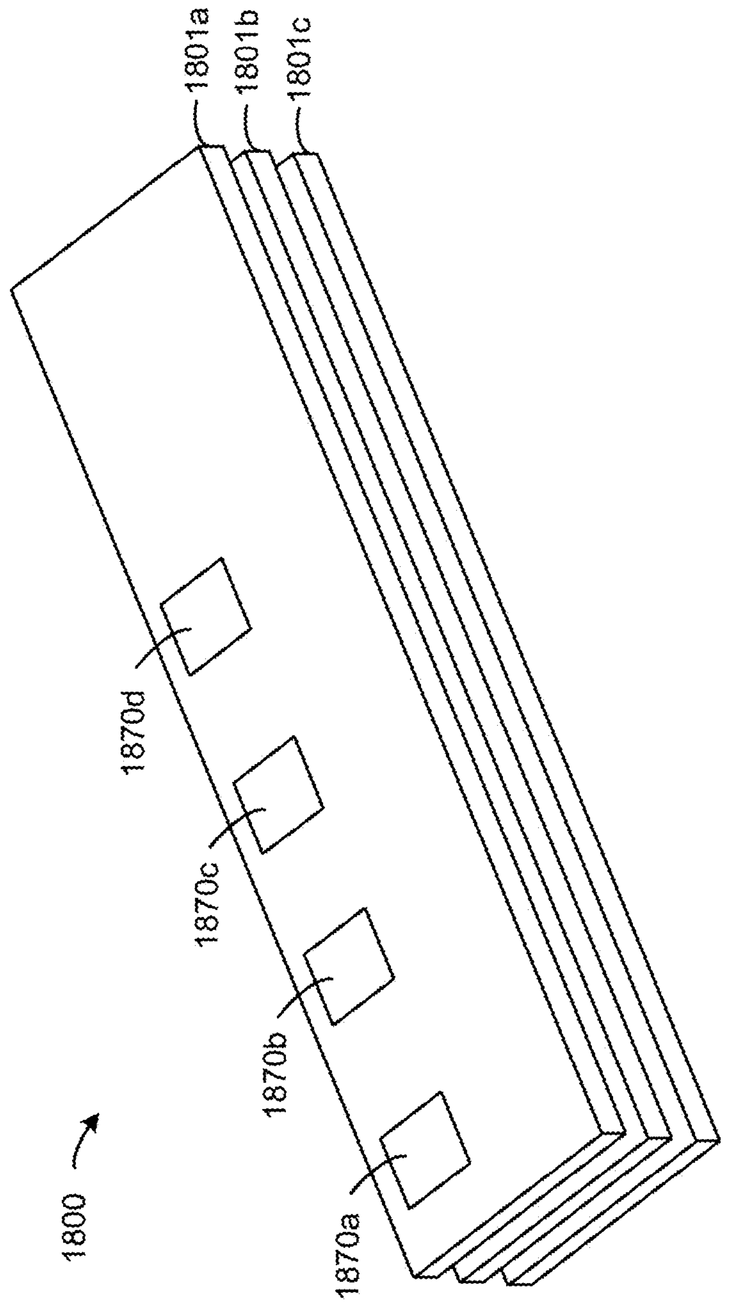
FIG. 18 is a semi-exploded view of an example PCS in accordance with an embodiment.

Referring to FIG. 18, shown therein is a semi-exploded view of an example PCS 1800. As shown in FIG. 18, PCS 1800 comprises at least 3 layers, 1801*a*, 1801*b*, and 1801*c*. PCS 1800 can further comprise one or more auxiliary sensors 1870*a-d*. In the example shown in FIG. 18, PCS 1800 includes four auxiliary sensors 1870*a-d* mounted on the top layer 1801*a*. In other embodiments, PCS 1800 can include one or more auxiliary sensors mounted on another layer, such as bottom layer 1801*c*. The one or more auxiliary sensors 1870*a-d* can include any third-party and/or off-the-shelf sensor. For example, the auxiliary sensor(s) can include a temperature sensor, a pressure sensor, an acceleration sensor, a force sensor, and/or an electrical properties sensor. The positioning, location, number, and/or sizing of auxiliary sensors 1870*a-d* in FIG. 18 are provided as an example only, and other alternatives are possible. As discussed herein, the PCS embodiments described herein that are configured for physical contact with the fluid being monitored are hermetically sealed. Accordingly, the wiring between any third-party and/or off-the-shelf sensor that is mounted to a PCS, such as PCS 1800, and the PCS will also be hermetically sealed. This addresses a challenge that often occurs with other inductive sensor solutions (i.e., ensuring the wiring between the third-party sensor and the inductive sensor is hermetically sealed).

Figure 19:
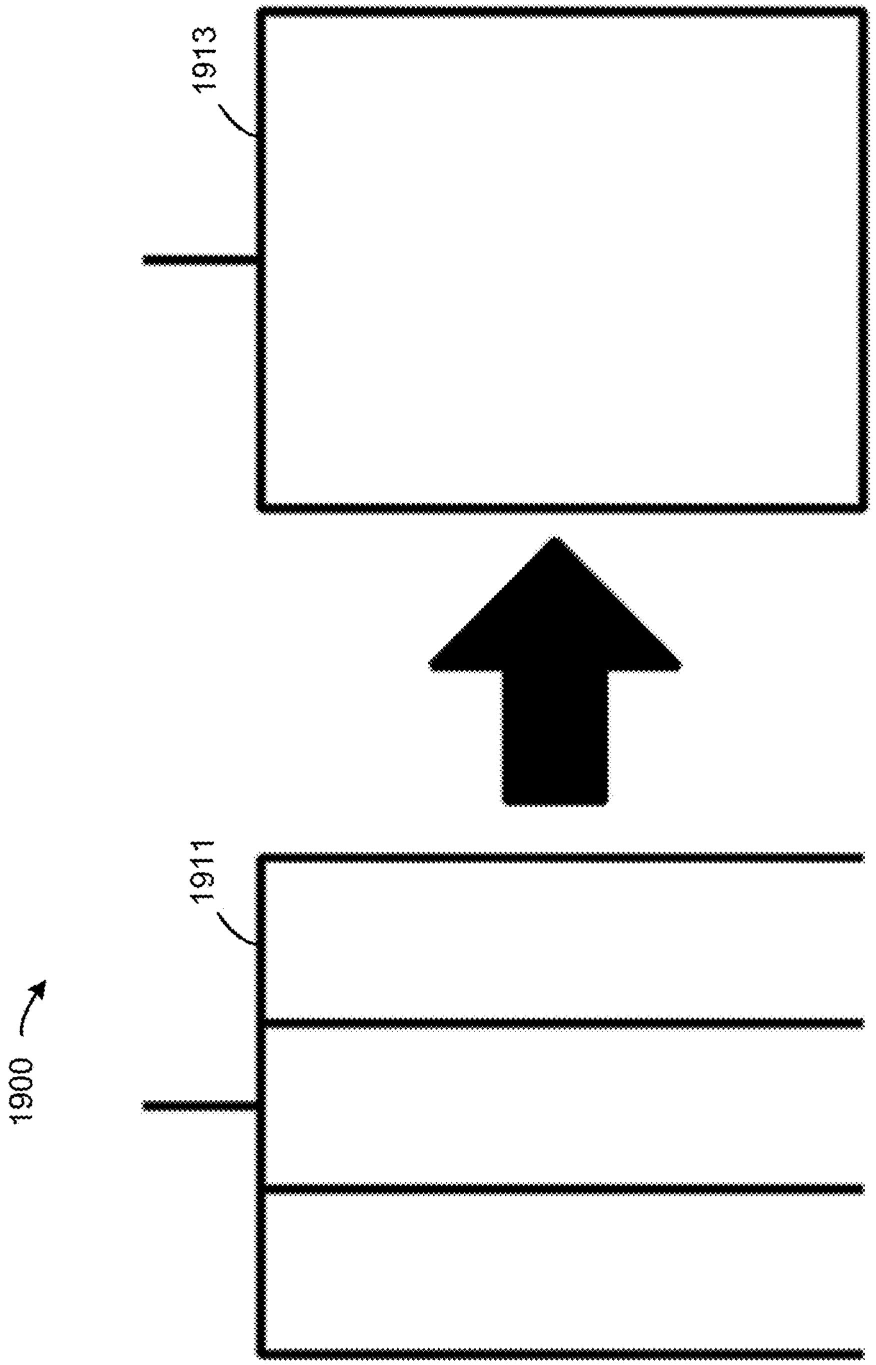
FIG. 19 is an example illustration of example Faraday shield traces in accordance with an embodiment.

In some embodiments, Faraday shield traces are printed on the PCSs to provide electric magnetic shielding. Referring to FIG. 19, shown therein is an illustration 1900 of example Faraday shield traces. In the illustrated example, the Faraday shield traces are printed on the top and bottom layers of the PCS. For example, trace 1911 represents a coarse Faraday shield trace on the top layer and 1913 represents a continuous Faraday shield plane on the top layer. Analogous traces can be printed on the bottom layer of the PCS. The Faraday shield works by attenuating a large portion of the environmental noise. Electromagnetic interference can be sufficiently attenuated by using a trace spacing on the same order as the wavelength of interference which is to be eliminated, although Faraday shields using smaller trace-spacings all the way down to a planar Faraday shield are also effective. In some embodiments, the Faraday shield traces are printed on a flexible PCB, which can be wrapped cylindrically inside each core of a mesh sensor.

Figure 21A:
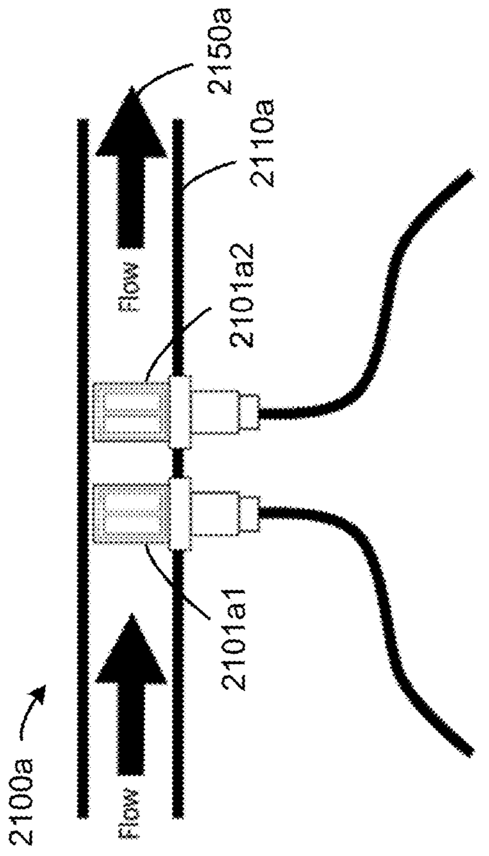
FIG. 21A is an illustration of example PCSs in accordance with an embodiment.
Figure 21B:
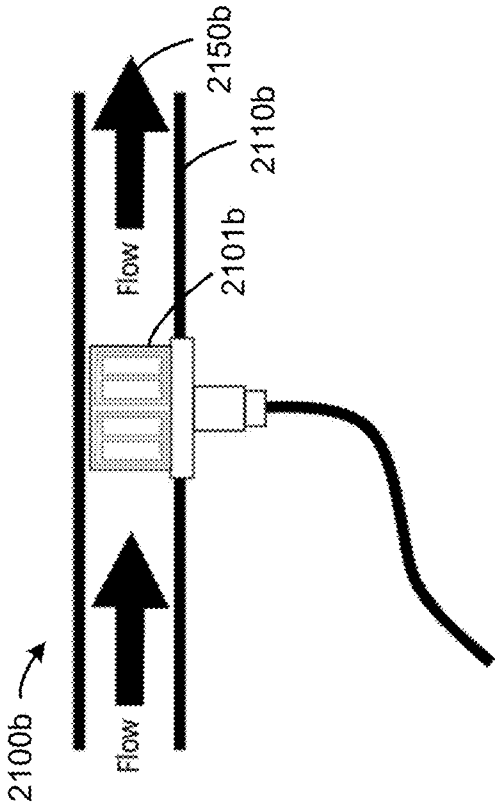
FIG. 21B is an illustration of another example PCS in accordance with an embodiment.

Reference will now be made to FIGS. 21A and 21B. Referring to FIG. 21A, shown therein is an illustration 2100*a* of two PCSs 2101*a*1 and 2101*a*2 installed in pipe 2110*a* having fluid flowing in direction 2150*a*. Referring to FIG. 21B, shown therein is an illustration 2100*b* of a single PCB 2101*b* that has two PCSs installed in pipe 2110*b* having fluid flowing in direction 2150*b*.

As described herein, the more lobes that a particle trace has, the easier the particle trace is to distinguish from noise. Accordingly, in some embodiments, such as the embodiments illustrated in 2100*a-b*, more than one PCS can be installed in a sequential manner. Each additional PCS will add two additional lobes for each particle trace. Although each of 2100*a-b* shows only two sequential PCSs, it should be understood that any number of sequential PCSs could be used. For example, in some embodiments, three sequential PCSs are installed.

Figure 23:
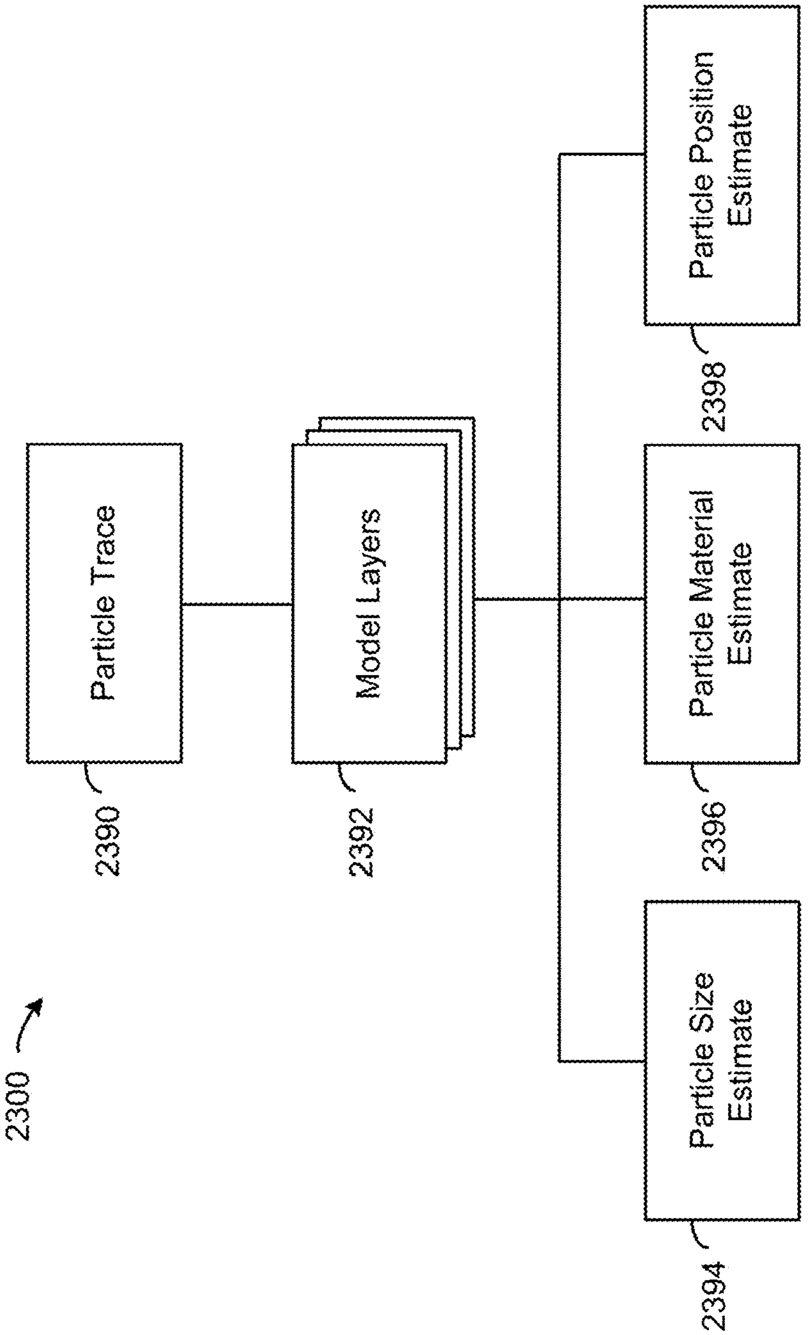
FIG. 23 is a block diagram of an example analysis of a PCS signal in accordance with an embodiment.

Referring to FIG. 23, shown therein is a block diagram 2300 of an example analysis of a PCS signal. As shown, a particle trace 2390 measured by a PCS is input to a model 2392 having one or more layers. The model 2392 can determine a particle size estimate 2394, a particle material estimate 2396, and/or a particle position estimate 2398.

In flow-through debris monitoring sensors, such as 1001*a*, the magnetic field generated by the field coils is approximately constant, radially and angularly, within a pipe in which the sensor is installed. Accordingly, as metal particles travel axially through the flow-through debris monitoring sensor, the position of each particle in the radial and angular directions do not affect the resulting particle trace. This means that the size of the particle that generated a particular particle trace can be calculated based on the amplitude of the particle trace because the amplitude of the particle trace is impacted only by the particle material and the particle size (i.e., the amplitude is not dependent on particle position relative to the sensor). The particle's material can be determined based on the phase of the particle trace relative to the drive signal.

In contrast, the magnetic field generated by the PCS embodiments as described herein is not constant within the fluid. Accordingly, the amplitude of a particle trace generated by a PCS is dependent on the position of the fluid particle relative to the PCS. Accordingly, amplitude, on its own, cannot be used to calculate the size of the particle that generated the particle trace. Instead, the amplitude as well as the shape of the particle trace is considered to estimate the particle size. A model 2392 is used to achieve this.

The model 2392 can be a machine learning model. In some embodiments, the model is a neural network. In some embodiments the model 2392 is an artificial neural network (ANN). The ANN can include multiple layers. In some embodiments, the ANN can include a 1D convolution layer and a fully connected layer. The 1D convolution layer can be used to align the particle traces.

The model 2392 can be trained to parse the amplitude and shape of particle trace 2390 in a manner as to determine the particle size estimate 2394 and the particle position estimate 2398 from the parsed amplitude and shape of the particle trace 2390. The model 2392 can further be trained to determine the particle material estimate 2396 based on a phase analysis of the particle trace 2390.

Figure 25:
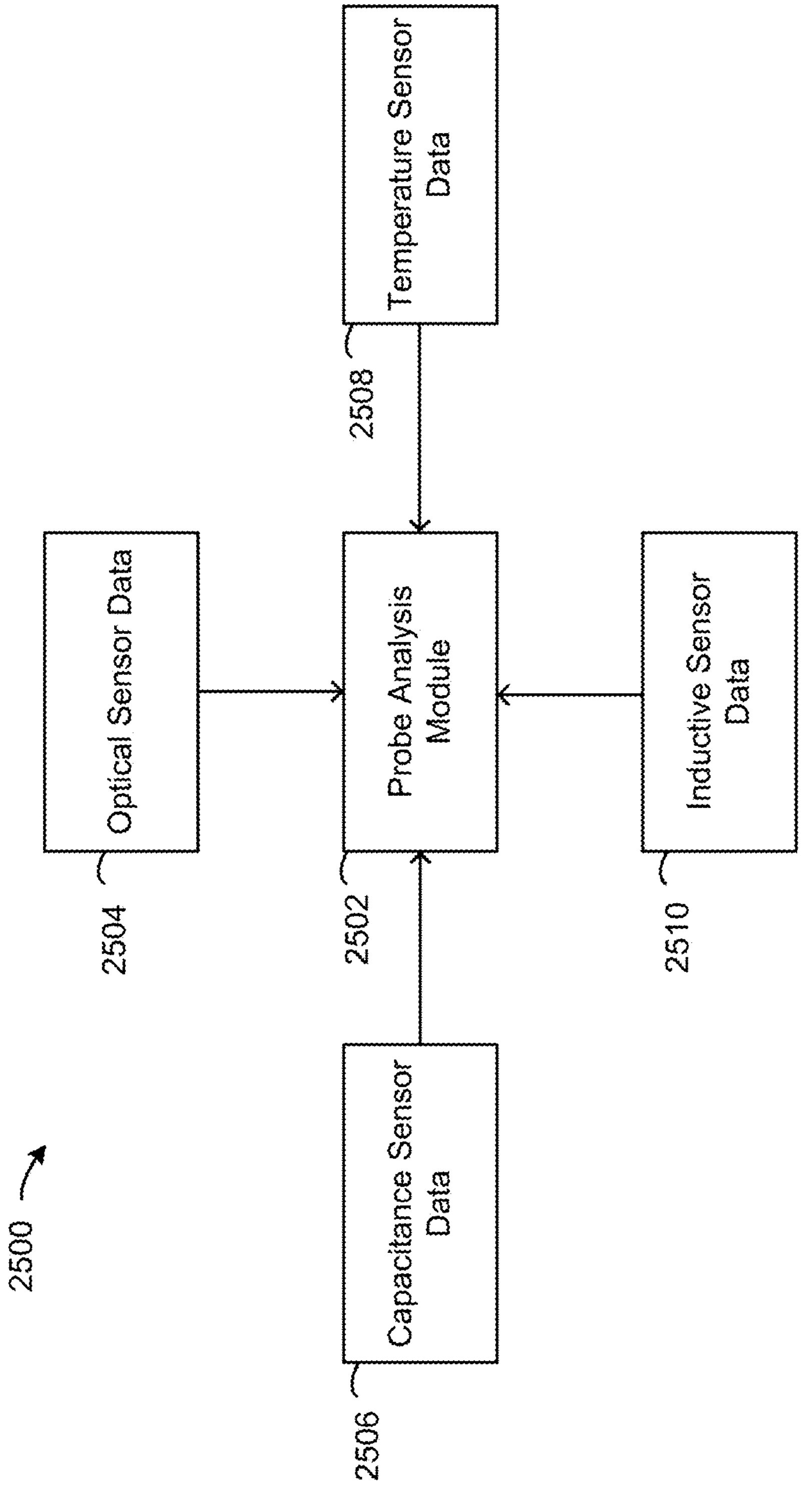
FIG. 25 is a block diagram of an example data flow within the fluid monitoring system of FIG. 2 in accordance with an embodiment.

Referring to FIG. 25, shown therein is a block diagram 2500 of an example data flow within a fluid monitoring system as described herein. As shown, probe analysis module 2502 can receive inputs including optical sensor data 2504, temperature sensor data 2508, inductive sensor data 2510, and electrical properties sensor data 2506. For example, the sensor data 2504, 2506, 2508, and 2510 can be analyzed independently or in combination. In some embodiments, the sensor data, whether raw or processed, can be used in combination for diagnostic and/or prognostic purposes using, for example, machine learning models or other data processing algorithms.

The use of additional sensors generates data capable of inferences to both detection as well as causes of failure which are not possible with either individual sensor in isolation. For example, the combination of fluorescence spectroscopy and inductive sensing can infer an oil-degradation-related component failure since degraded oil has a higher viscosity, which can induce wear on the lubricated components. Monitoring for wear debris in isolation would suggest replacing the damaged component, monitoring for oil degradation would suggest replacing the oil, but monitoring for both would suggest that oil degradation is causing component failure and to replace (or perform other maintenance actions on) both oil and the damaged component. Similarly, measuring the water content of the oil using an electrical properties sensor as well as wear debris using an inductive sensor could make the inference that a component is being damaged by corrosion.

The use of additional sensors can also detect a more complete set of failure modes. For example, the combination of fluorescence spectroscopy and electrical properties sensing can monitor for both fuel and water contamination of oil, whereas fluorescence spectroscopy would only detect fuel contamination and electrical properties sensing would only detect water contamination.

In some embodiments, the sensor inputs are combined for increased reliability of detection, pinpointing the failure mode and/or damaged component and improved accuracy of predictions of remaining useful life. For example, in the case of some types of fuel and coolant contamination, the electrical properties sensor may indicate contamination in the oil but it may be challenging to identify the type of contamination or source of contamination. The electrical properties sensor then functions as an indicator and corroborative input, while the fluorescence sensor correctly identifies the type of contamination. The quantification of the level of contamination by the fluorescence sensor can then be checked against the measurement from the electrical properties sensor and correlations or other algorithms can be employed to improve the accuracy of the diagnostic output from the overall system. This would enable the end user to identify the source of contamination such as faulty injectors and take the correct maintenance action promptly.

In some embodiments, a diagnostic model utilizes historic engine, operational and performance data to evaluate the probability that a certain component within the system is damaged. The diagnostic model may be a machine learning model such as a decision tree model. The inputs of the diagnostic model can include operational data such as speed, load, torque, and runtime, and Condition Indicator data such as pressure, temperature, wear debris, vibration, oil condition data.

In some embodiments, the diagnostic model is capable of leveraging data from multiple sensors such as the Fluid Condition sensors optical sensing system (e.g., Optical sensing System or electrical properties sensor), debris monitoring sensor (e.g., ODM sensor), and other Engine Control Unit sensors (e.g., temperature sensor or pressure sensor) to identify and distinguish between performance faults and functional faults. In the case of performance faults, component damage is detectable by online sensors or other offline methods but the overall system remains functional. Spall formation on a bearing or other component is an example of a performance fault that can be tracked in terms of the number of debris particles released into the oil as the spall propagates. Once this fault has been detected, there is a finite amount of time before a functional fault will occur, and a scheduled maintenance action will be required. The more severe functional fault typically results in engine shutdown, as either a component is simply no longer able to function, or that continued operation risks immediate catastrophic engine failure. Disk rupture in gas turbines or bearing cage failures in gearboxes are examples of functional faults.

Figure 26:
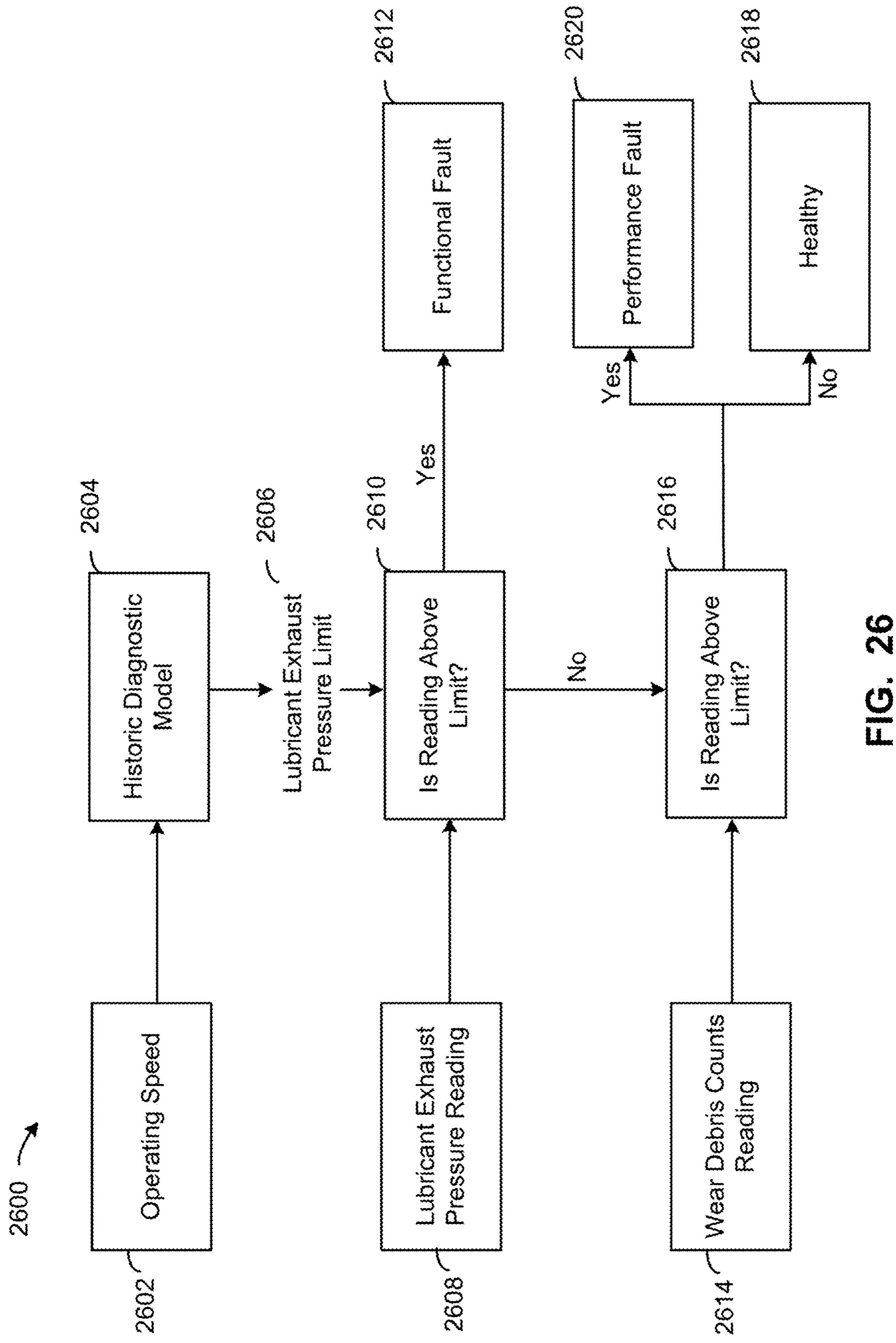
FIG. 26 is a block diagram of an example diagnostic model in accordance with an embodiment.

For example, the operating speed, the wear debris counts, vibration and the lubricant exhaust pressure can be used as inputs to the diagnostic model, which then classifies the condition of the engine as one of three outputs states. An example logic tree 2600 for an example diagnostic model can be seen in FIG. 26. The operating speed 2602 of the engine, obtained from an ECU sensor, is used as an input to a historic model 2604, which outputs a lubricant exhaust pressure limit 2606. A pressure sensor provides the lubricant exhaust pressure reading 2608. At 2610, the lubricant exhaust pressure limit 2606 and the lubricant exhaust pressure reading 2608 are compared. If the lubricant exhaust pressure reading 2608 is above the lubricant exhaust pressure limit 2606, the engine is determined to have a functional fault at block 2612. At the same time, the wear debris count reading 2614 obtained from the ODM sensor is compared to a wear debris counts rate limit (not shown in FIG. 26) at block 2616. The engine is diagnosed healthy at block 2618 if both ODM and pressure sensors are below their respective limits. Correspondingly, if the debris counts rate detection limit is exceeded, then there is a fault on the engine and the lubricant exhaust pressure 2608 is used to determine whether it consists of a functional or performance failure. Once the engine has a detectable performance fault at block 2620, prognostic models can be implemented to track the RUL.

Figure 27:
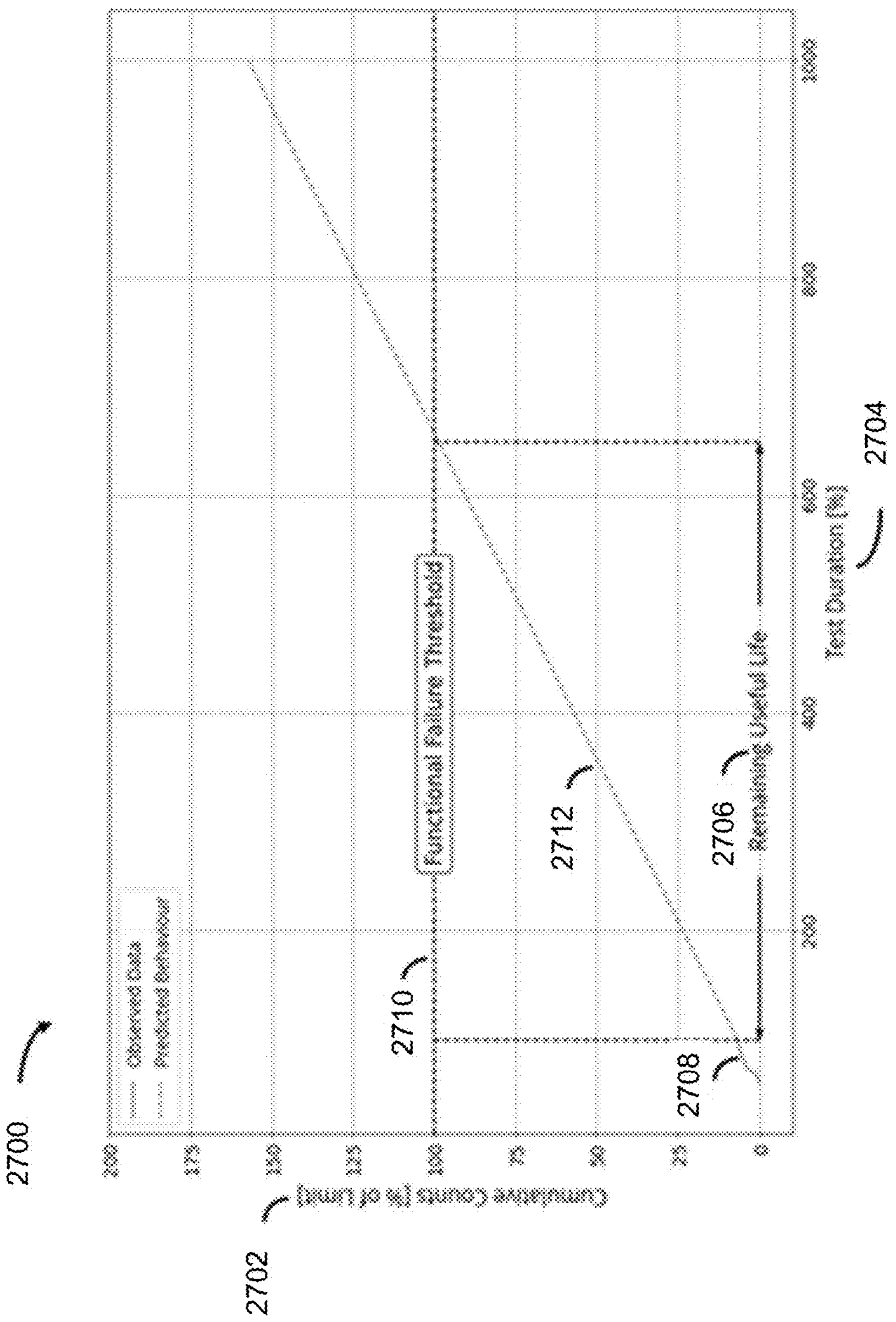
FIG. 27 is an example plot of debris count as a function of test duration in accordance with an embodiment.

In some embodiments, the prognostic models can output an optimal time to perform the maintenance, by predicting the functional RUL based on the measured rate progression of the given performance fault and a threshold with a margin of safety before critical functional failure. An example, plot 2700 to be used for obtaining the RUL 2706 from debris count using historic counts behaviour is seen in FIG. 27. The y-axis 2702 represents the cumulative debris count obtained from the ODM sensor and the x-axis 2704 represents time. The RUL 2706 is determined by taking the current count degradation rate 2708 and extrapolating that rate out to the failure threshold 2710, forming a predicted behaviour trendline 2712.

ODM sensor data can be combined with engine vibration, data obtained through accelerometers, temperature data, engine operational data such as loading and rotational speeds, offline and at-line collected data types such as filter and oil sample analyses, and engine specific information, such as time since maintenance, total operational hours, previous builds, etc. This combination allows for improvements in ODM based diagnostic condition indicators using supervised machine learning algorithms such as decision trees and regression models, and other forms of traditional data analytics.

Online ODM sensor data is a continuous measurement system that goes through several analytical models before it can provide an accurate and reliable diagnosis as to the current damage state of rolling element bearings, gears, journal bearings, seals, and various other forms of oil wetted rotating machinery components. Several of these models are critical and will be stated herein, with the example of rolling element bearings (REB).

Figure 28:
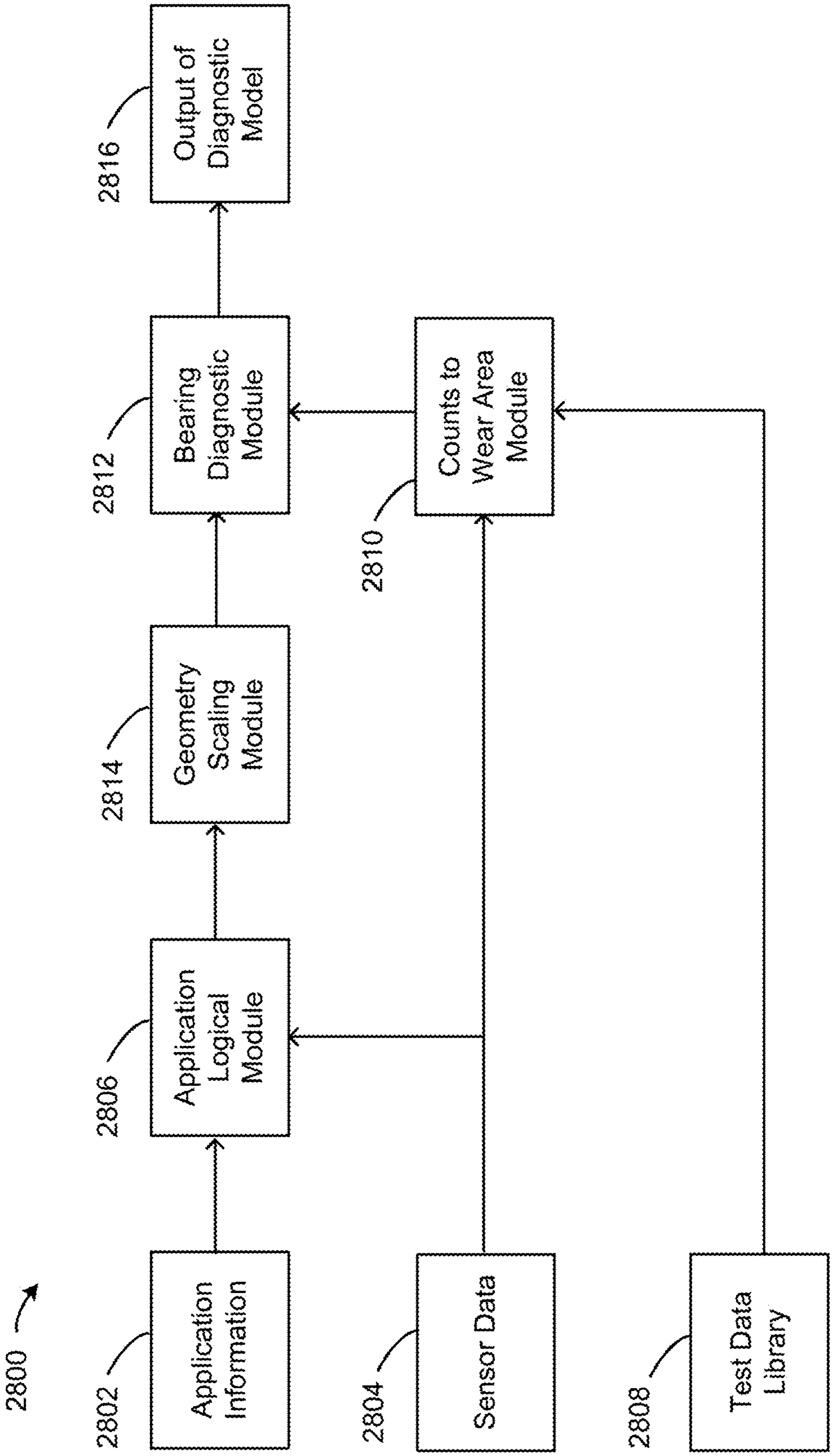
FIG. 28 is a block diagram of an example diagnostic model in accordance with an embodiment.

Referring to FIG. 28, shown therein is a flow diagram 2800 of a diagnostics model in accordance with an embodiment. The inputs of the ODM based diagnostic model include critical application specific knowledge 2802 about the target component and engine. For REB in particular, this includes the raceway geometries, number of rolling elements and their geometries, all relevant material information, as well as information about the lubrication environment including flowrates, and wear debris particle transport efficiencies.

Another input to the diagnostic model is the sensor data 2804 such as ODM sensor counts, as well as the sizing criteria. This continuously monitored data provides direct correlation to damaged components.

The diagnostic model involves application specific logical tailoring via the application logical module 2806 and the geometry scaling module 2814. This includes logic driven component isolation, any lubrication environment scaling factors and models for applications that have low transport efficiencies or unique sensor installation logistics. The output of the geometry scaling module 2814 is a scaled counts property that confirms the existence of a fault and identifies the fault component. The application logical module 2806 and the geometry scaling module 2814 include a series of logical conditions which apply a particle size specific scaling factor to the sensor data 2804 (e.g., counts input) based on user pre-set application settings. The component isolation setting is based on sensor installation location, (i.e. which component is it downstream of) or simple data features of the counts such as their size distribution, total counts amount, and overall change in total counts over a specific application dependent time interval. Once the scaled counts version passes a certain application specific pre-set threshold, a fault is diagnosed, and the model engages the next module(s). Depending on the application, a warning state will also be issue to the operator of the application once this threshold is passed.

The test data library 2808 includes a series of ground inspections from field applications and laboratory testing that form the fundamental physics driven linear correlation between wear debris count and damaged component area/volume/mass. The linear correlation slope is continuously updated for improved accuracy and reliability.

The linear correlation is also physics informed so that it can be adjusted based on component types and wear modes, which can affect the particle size distribution. The particle size distribution is key for application of the linear correlation.

The counts-to-wear area model 2810 applies the linear relationship obtained from the test data library 2808 to the modified counts input. The resultant product is output as a damaged area value. In some embodiments, the output includes a volume or mass. This is a probability distribution to the damage on a particular component in the application engine. This distribution is then translated into an understandable component specific damage quantity within the bearing diagnostic module 2812. For REB, this may include a raceway spall level in terms of angle of spall, percentage of raceway that is spalled, and/or number of rolling elements in spall at an instant. These require the geometric information of the component provided within the system input.

The output of the diagnostic module 2816 is a distribution of the component specific damage. Depending on the application requirements, a single value can be reported rather than a distribution for operator use. Examples include 99% reliability (where the probability of damage level greater than the reported value is 1%) or the expected value from the distribution. Furthermore, in some embodiments, the value is compared against a threshold driven by the degradation physics of the component and its geometry. If the reported damage level is larger than this threshold, an alarm can be issued to the operator or maintenance program oversight.

Figure 29:
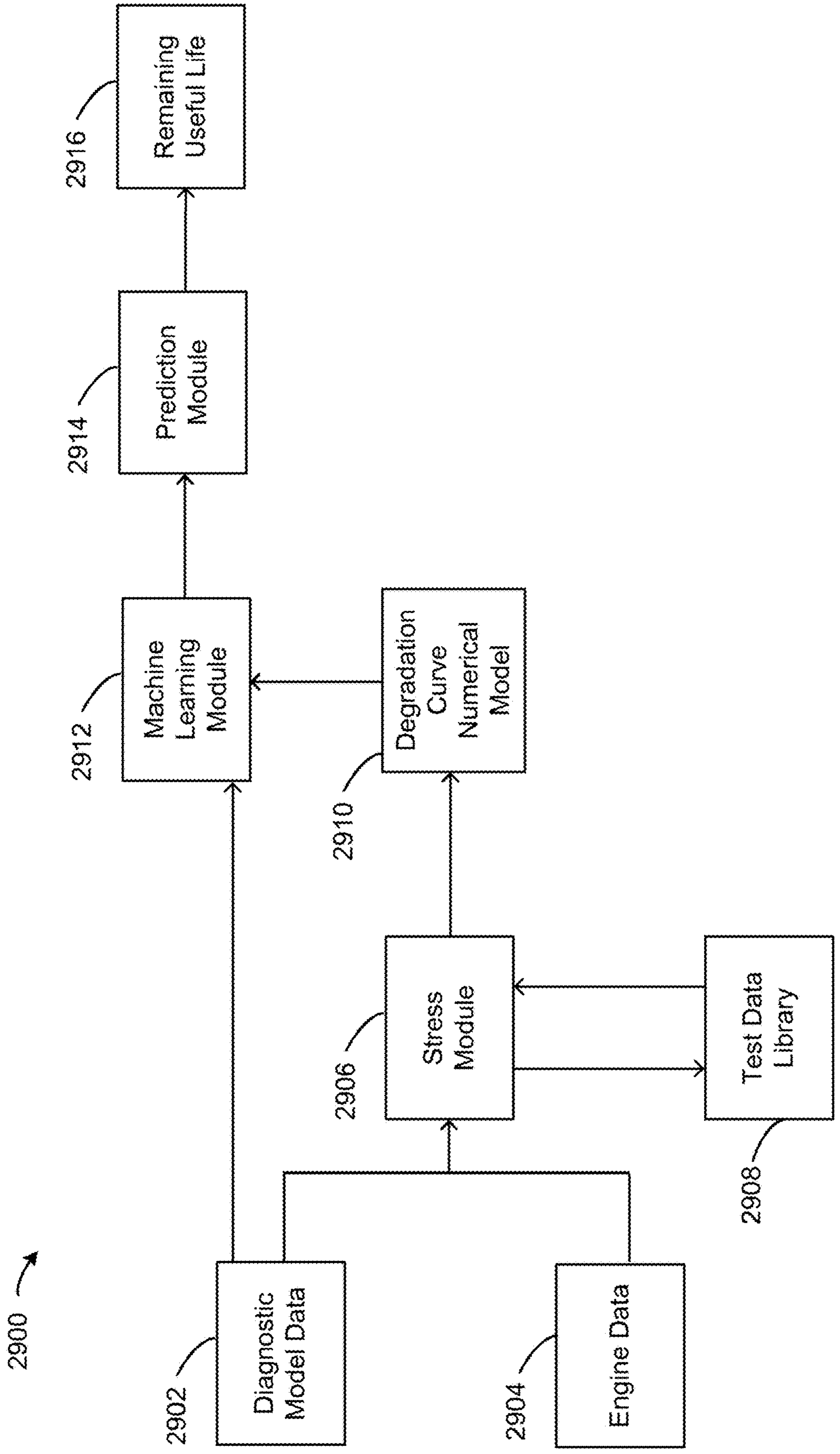
FIG. 29 is a block diagram of an example prognostic model in accordance with an embodiment.

Referring to FIG. 29, shown therein is a flow diagram 2900 of a prognostic model in accordance with an embodiment. The goal of the prognostic model is to take in the history of the diagnostic model outputs, such as output 2916, over a period of time once a fault is detected and predict the time until the probability of catastrophic failure is significant (e.g., maintenance should be performed). The timescale of this notice can be in the range of hours to days to months, for example, depending on the application. The model can receive diagnostic model data 2902 such as diagnostic model distribution history since last engine build, sensor installation, or when a fault was first diagnosed. The model can further receive engine data 2904, including the engine load, rotational speed, and build history, for example. Furthermore, component specific geometry data is used by the model in a similar manner as in the diagnostic model as described with reference to FIG. 28.

The prognostic model uses a test data library 2908 that includes experimentally derived degradation curves obtained through laboratory REB failures, or experimental field trials. Numerical physics driven models are then fitted to these curves, with consideration for both loads and rotational speeds. These are mainly for REB spall, however, the library 2908 accepts testing continuously to add capability for different failure modes, different operational regimes, different materials, and different oil wetted components.

The engine load and speed data provided are critical to deciphering which degradation curve the bearing will follow. Built into this curve are degradation curve changepoints based on the damage level, load changes, and/or physical degradation phenomena. Therefore, there exists a recursive relationship between the degradation curve library 2908, diagnostic model history 2902, and the individual REB numerically modelled degradation curve.

The load and speed data are not sufficient for degradation curves, as REB can be under various different conditions dependent on application, industry, and engine size. For this reason, the stress module 2906 translates the loading information into scalable features.

The degradation curve numerical model 2910 includes exponential and linear growth models. It includes deterministic coefficient and variables set-up based on the degradation physics, geometries, and application settings. There are also stochastic experimentally derived physics informed coefficients and variables that cause for a distribution as to the expected shape of the REB degradation curve. Experimental testing has revealed that bearings even under identical conditions can have vastly different degradation curves. For this reason, the machine learning module 2912 can be used to improve accuracy and best match the degradation curve via the diagnostic model data 2902. In other words, the internal stochastic coefficients of the degradation curve numerical models 2910 are shifted to improve accuracy and reliability in matching the evolution in the diagnostic model distribution over the time the faulted component is in operation. These methodologies may employ Monte Carlo methodologies and supervised machine learning approaches within the machine learning module 2912.

At an application specific point in the faulted component operation, a prediction as to the remaining useful life 2916 is made by projecting the numerical model into the future, with some idea as to the future mission profile of the target asset. This prediction module 2914 has the projected curve and reports the time, revolutions, flight cycles or equivalent operator friendly criteria until a threshold for failure. Application driven factors such as reliability or accuracy can also be implemented. The threshold is physics informed and relates to the onset of catastrophic failure risk, such as seizure or cage fracture, and is application dependent.

Numerous specific details are set forth herein in order to provide a thorough understanding of the exemplary embodiments described herein. However, it will be understood by those of ordinary skill in the art that these embodiments may be practiced without these specific details. In other instances, well-known methods, procedures and components have not been described in detail so as not to obscure the description of the embodiments. Furthermore, this description is not to be considered as limiting the scope of these embodiments in any way, but rather as merely describing the implementation of these various embodiments.

CLAUSES

Clause 1: A system for monitoring one or more properties of a fluid in a mechanical device, the system comprising: a printed circuit board (PCB)-based inductive sensor for detecting one or more metallic particles in the fluid, the PCB-based inductive sensor comprising: at least one printed circuit board (PCB) comprising: one or more layers comprising each of a first field coil trace and a second field coil trace; and one or more layers comprising a sense coil trace, wherein the first field coil trace and the second field coil trace generate a magnetic field when electrically driven and the sense coil trace detects a change in the magnetic field produced by the one or more metallic particles in the fluid.

Clause 2: The system of any of the preceding clauses, wherein the at least one PCB comprises one PCB, and the one PCB comprises the first field coil trace, the second field coil trace and the sense coil trace, each printed on one or more layers of the PCB.

Clause 3: The system of any of the preceding clauses, wherein the first field coil trace, the second field coil trace and the sense coil trace are wound concentrically on the one PCB.

Clause 4: The system of any of the preceding clauses, wherein each of the first field coil trace and the second field coil trace is wider than the sense coil trace.

Clause 5: The system of any of the preceding clauses, wherein the at least one PCB comprises a first PCB, a second PCB and a third PCB, the first PCB comprising the first field coil trace printed on one or more layers of the first PCB, the second PCB comprising the sense coil trace printed on one or more layers of the second PCB and the third PCB comprising the second field coil trace printed on one or more layers of the third PCB.

Clause 6: The system of any of the preceding clauses, wherein the PCB-based inductive sensor comprises a mesh structure, and wherein the first PCB, the second PCB and the third PCB comprise one or more apertures allowing the fluid to pass through.

Clause 7: The system of any of the preceding clauses, wherein the PCB-based inductive sensor further comprises at least one spacer component coupled to one or more of the first PCB, the second PCB and the third PCB, and wherein each spacer component is implemented in a substantially ring-shaped configuration with an aperture to allow the fluid to pass through.

Clause 8: The system of any of the preceding clauses, wherein the PCB-based inductive sensor comprises a bypass channel formed in the at least one PCB to allow larger of the one or more metallic particles to pass through.

Clause 9: The system of any of the preceding clauses, wherein the PCB-based inductive sensor further comprises a flow conditioner adjacent to the at least one PCB to guide the fluid to pass through the one or more apertures.

Clause 10: The system of any of the preceding clauses, further comprising an oil containment tube (OCT) for insertion into the corresponding one or more apertures to provide a sealed pathway for the fluid to pass through.

Clause 11: The system of any of the preceding clauses, wherein each oil containment tube has a curved opening.

Clause 12: The system of any of the preceding clauses, wherein the sensor comprises a plurality of coil triplets, each coil triplet comprising the first field coil trace of a corresponding first PCB, the sense coil trace of a corresponding second PCB and the second field coil trace of a corresponding third PCB, and wherein the plurality of coil triplets are coupled in a parallel configuration such that each coil triplet functions as an independent sensing element.

Clause 13: The system of any of the preceding clauses, wherein the sensor comprises a plurality of first PCBs, a plurality of second PCBs and a plurality of third PCBs, and wherein the first field coil traces of the plurality of first PCBs are connected in series, the sense coil traces of the plurality of second PCBs are connected in series and the second field coil traces of the plurality of third PCBs are connected in series.

Clause 14: The system of any of the preceding clauses, wherein the at least one PCB is configured in a split-PCB configuration comprising two PCBs, wherein a first PCB comprises one or more layers of the sense coil trace and one or more layers of one of the first field coil trace and the second field coil trace, and wherein a second PCB comprises one or more layers of the sense coil trace and one or more layers of the other of the first field coil trace and the second field coil trace.

Clause 15: The system of any of the preceding clauses, wherein an output signal from each sense coil trace of the corresponding PCB is connected in parallel.

Clause 16: The system of any of the preceding clauses, wherein an output signal from each sense coil trace of the corresponding PCB is connected in series.

Clause 17: The system of any of the preceding clauses, wherein the at least one PCB is configured in a double-D configuration comprising one PCB, wherein the first field coil trace is printed on one or more layers of the one PCB in a D-configuration, the second field coil trace is printed on one or more layers of the one PCB in a reversed-D configuration, and wherein the sense coil is printed on one or more layers of the one PCB in a substantially ring-shaped configuration.

Clause 18: The system of any of the preceding clauses, wherein the first field coil trace and the second field coil trace are configured to generate magnetic fields of opposite polarity, and wherein when the one or more metallic particles interact with the sense coil trace, a double-lobed voltage signal is generated.

Clause 19: The system of any of the preceding clauses, wherein the PCB-based inductive sensor comprises a bypass channel formed in the at least one PCB to allow larger of the one or more metallic particles to pass through.

Clause 20: The system of any of the preceding clauses, wherein the PCB-based inductive sensor further comprises a flow conditioner adjacent to the at least one PCB to guide the fluid to pass through the one or more apertures.

Clause 21: The system of any of the preceding clauses, wherein the at least one PCB is fabricated from a chemically inert material configured to tolerate exposure to the fluid.

Clause 22: The system of any of the preceding clauses, wherein the at least one PCB comprises a flexible substrate configured to be wrapped around a pipe carrying the fluid in the mechanical device.

Clause 23: The system of any of the preceding clauses, wherein the PCB-based inductive sensor comprises a hydrodynamic profile to reduce pressure drop in the fluid flowing through the PCB-based inductive sensor.

Clause 24: The system of any of the preceding clauses, wherein the PCB-based inductive sensor comprises one or more Faraday shield traces printed on one or more layers of the at least one PCB to attenuate electromagnetic interference.

Clause 25: The system of any of the preceding clauses, wherein the PCB-based inductive sensor further comprises one or more auxiliary sensors selected from a group consisting of: temperature sensors, pressure sensors, acceleration sensors, force sensors, or electrical property sensors, the auxiliary sensors being hermetically sealed to the at least one PCB.

Clause 26: The system of any of the preceding clauses, further comprising a processor coupled to the PCB-based inductive sensor, wherein the processor is configured to: receive an output signal from the PCB-based inductive sensor; and analyze the output signal using a machine learning model to estimate one or more of a size, position and material type of the one or more metallic particles in the fluid.

Clause 27: The system of any of the preceding clauses, wherein the comprises a lubricant oil.

Clause 28: The system of any of the preceding clauses, wherein the fluid comprises a fuel.

Clause 29: The system of any of the preceding clauses, wherein the fluid comprises a hydraulic oil.

Clause 30: The system of any of the preceding clauses, wherein the fluid comprises a transmission oil.

Clause 31: The system of any of the preceding clauses, wherein the fluid comprises a coolant.

Clause 32: The system of any of the preceding clauses, further comprising an optical sensor comprising an excitation light aperture and an emission light aperture, wherein the excitation light aperture transmits an excitation light to the fluid and the emission light aperture receives an emission light from the fluid.

Clause 33: The system of any of the preceding clauses, wherein the optical sensor comprises a fluorescence sensor.

Clause 34: The system of any of the preceding clauses, further comprising one or more of a temperature sensor, an inductive sensor, an electrical properties sensor, and a viscosity sensor.

Clause 35: The system of any of the preceding clauses, further comprising a probe, wherein the printed circuit board (PCB)-based inductive sensor is housed in the probe.

Clause 36: The system of any of the preceding clauses, wherein at least a portion of the probe is insertable into the fluid.

Clause 37: The system of any of the preceding clauses, wherein the probe is dimensionally complementary to at least a portion of an in-situ vessel of the fluid.

Clause 38: A system for monitoring one or more properties of a fluid in a mechanical device, the system comprising: a printed circuit board (PCB)-based inductive sensor for detecting one or more metallic particles in the fluid, the PCB-based inductive sensor comprising: at least one printed circuit board (PCB) comprising: one or more layers comprising a field coil trace; and one or more layers comprising each of a first sense coil trace and a second sense coil trace, wherein the field coil trace is configured to generate a magnetic field when electrically driven and each of the first sense coil trace and the second sense coil trace are configured to detect a change in the magnetic field produced by the one or more metallic particles in the fluid.

Clause 39: A system for monitoring one or more properties of a fluid in a mechanical device, the system comprising: a printed circuit board (PCB)-based inductive sensor for detecting one or more metallic particles in the fluid, the PCB-based inductive sensor comprising: one or more printed circuit board (PCBs) comprising one or more layers forming at least one field coil trace and at least one sense coil trace, wherein the at least one field coil trace is configured to generate a magnetic field when electrically driven and the at least one sense coil is configured to detect a change in the magnetic field produced by the one or more metallic particles in the fluid.

Clause 40: A method of monitoring one or more properties of a fluid in a mechanical device, the method comprising: providing a printed circuit board (PCB)-based inductive sensor for detecting one or more metallic particles in the fluid, the PCB-based inductive sensor comprising: at least one printed circuit board (PCB) comprising: one or more layers comprising each of a first field coil trace and a second field coil trace; and one or more layers comprising a sense coil trace, wherein the first field coil trace and the second field coil trace generate a magnetic field when electrically driven and the sense coil trace detects a change in the magnetic field produced by the one or more metallic particles in the fluid.

Clause 41: The method of any of the preceding clauses, wherein the at least one PCB comprises one PCB, and the one PCB comprises the first field coil trace, the second field coil trace and the sense coil trace, each printed on one or more layers of the PCB.

Clause 42: The method of any of the preceding clauses, wherein the first field coil trace, the second field coil trace and the sense coil trace are wound concentrically on the one PCB.

Clause 43: The method of any of the preceding clauses, wherein each of the first field coil trace and the second field coil trace is wider than the sense coil trace.

Clause 44: The method of any of the preceding clauses, wherein the at least one PCB comprises a first PCB, a second PCB and a third PCB, the first PCB comprising the first field coil trace printed on one or more layers of the first PCB, the second PCB comprising the sense coil trace printed on one or more layers of the second PCB and the third PCB comprising the second field coil trace printed on one or more layers of the third PCB.

Clause 45: The method of any of the preceding clauses, wherein the PCB-based inductive sensor comprises a mesh structure, and wherein the first PCB, the second PCB and the third PCB comprise one or more apertures allowing the fluid to pass through.

Clause 46: The method of any of the preceding clauses, wherein the PCB-based inductive sensor further comprises at least one spacer component coupled to one or more of the first PCB, the second PCB and the third PCB, and wherein each spacer component is implemented in a substantially ring-shaped configuration with an aperture to allow the fluid to pass through.

Clause 47: The method of any of the preceding clauses, wherein the PCB-based inductive sensor comprises a bypass channel formed in the at least one PCB to allow larger of the one or more metallic particles to pass through.

Clause 48: The method of any of the preceding clauses, wherein the PCB-based inductive sensor further comprises a flow conditioner adjacent to the at least one PCB to guide the fluid to pass through the one or more apertures.

Clause 49: The method of any of the preceding clauses, further comprising an oil containment tube (OCT) for insertion into the corresponding one or more apertures to provide a sealed pathway for the fluid to pass through.

Clause 50: The method of any of the preceding clauses, wherein each oil containment tube has a curved opening.

Clause 51: The method of any of the preceding clauses, wherein the sensor comprises a plurality of coil triplets, each coil triplet comprising the first field coil trace of a corresponding first PCB, the sense coil trace of a corresponding second PCB and the second field coil trace of a corresponding third PCB, and wherein the plurality of coil triplets are coupled in a parallel configuration such that each coil triplet functions as an independent sensing element.

Clause 52: The method of any of the preceding clauses, wherein the sensor comprises a plurality of first PCBs, a plurality of second PCBs and a plurality of third PCBs, and wherein the first field coil traces of the plurality of first PCBs are connected in series, the sense coil traces of the plurality of second PCBs are connected in series and the second field coil traces of the plurality of third PCBs are connected in series.

Clause 53: The method of any of the preceding clauses, wherein the at least one PCB is configured in a split-PCB configuration comprising two PCBs, wherein a first PCB comprises one or more layers of the sense coil trace and one or more layers of one of the first field coil trace and the second field coil trace, and wherein a second PCB comprises one or more layers of the sense coil trace and one or more layers of the other of the first field coil trace and the second field coil trace.

Clause 54: The method of any of the preceding clauses, wherein an output signal from each sense coil trace of the corresponding PCB is connected in parallel.

Clause 55: The method of any of the preceding clauses, wherein an output signal from each sense coil trace of the corresponding PCB is connected in series.

Clause 56: The method of any of the preceding clauses, wherein the at least one PCB is configured in a double-D configuration comprising one PCB, wherein the first field coil trace is printed on one or more layers of the one PCB in a D-configuration, the second field coil trace is printed on one or more layers of the one PCB in a reversed-D configuration, and wherein the sense coil is printed on one or more layers of the one PCB in a substantially ring-shaped configuration.

Clause 57: The method of any of the preceding clauses, wherein the first field coil trace and the second field coil trace are configured to generate magnetic fields of opposite polarity, and wherein when the one or more metallic particles interact with the sense coil trace, a double-lobed voltage signal is generated.

Clause 58: The method of any of the preceding clauses, wherein the PCB-based inductive sensor comprises a bypass channel formed in the at least one PCB to allow larger of the one or more metallic particles to pass through.

Clause 59: The method of any of the preceding clauses, wherein the PCB-based inductive sensor further comprises a flow conditioner adjacent to the at least one PCB to guide the fluid to pass through the one or more apertures.

Clause 60: The method of any of the preceding clauses, wherein the at least one PCB is fabricated from a chemically inert material configured to tolerate exposure to the fluid.

Clause 61: The method of any of the preceding clauses, wherein the at least one PCB comprises a flexible substrate configured to be wrapped around a pipe carrying the fluid in the mechanical device.

Clause 62: The method of any of the preceding clauses, wherein the PCB-based inductive sensor comprises a hydrodynamic profile to reduce pressure drop in the fluid flowing through the PCB-based inductive sensor.

Clause 63: The method of any of the preceding clauses, wherein the PCB-based inductive sensor comprises one or more Faraday shield traces printed on one or more layers of the at least one PCB to attenuate electromagnetic interference.

Clause 64: The method of any of the preceding clauses, wherein the PCB-based inductive sensor further comprises one or more auxiliary sensors selected from a group consisting of: temperature sensors, pressure sensors, acceleration sensors, force sensors, or electrical property sensors, the auxiliary sensors being hermetically sealed to the at least one PCB.

Clause 65: The method of any of the preceding clauses, further comprising a processor coupled to the PCB-based inductive sensor, wherein the processor is configured to: receive an output signal from the PCB-based inductive sensor; and analyze the output signal using a machine learning model to estimate one or more of a size, position and material type of the one or more metallic particles in the fluid.

Clause 66: The method of any of the preceding clauses, wherein the comprises a lubricant oil.

Clause 67: The method of any of the preceding clauses, wherein the fluid comprises a fuel.

Clause 68: The method of any of the preceding clauses, wherein the fluid comprises a hydraulic oil.

Clause 69: The method of any of the preceding clauses, wherein the fluid comprises a transmission oil.

Clause 70: The method of any of the preceding clauses, wherein the fluid comprises a coolant.

Clause 71: The method of any of the preceding clauses, further comprising an optical sensor comprising an excitation light aperture and an emission light aperture, wherein the excitation light aperture transmits an excitation light to the fluid and the emission light aperture receives an emission light from the fluid.

Clause 72: The method of any of the preceding clauses, wherein the optical sensor comprises a fluorescence sensor.

Clause 73: The method of any of the preceding clauses, further comprising one or more of a temperature sensor, an inductive sensor, an electrical properties sensor, and a viscosity sensor.

Clause 74: The method of any of the preceding clauses, further comprising a probe, wherein the method comprises housing the printed circuit board (PCB)-based inductive sensor in the probe.

Clause 75: The method of any of the preceding clauses, wherein at least a portion of the probe is insertable into the fluid.

Clause 76: The method of any of the preceding clauses, wherein the probe is dimensionally complementary to at least a portion of an in-situ vessel of the fluid.

Clause 77: A method for monitoring one or more properties of a fluid in a mechanical device, the method comprising: providing a printed circuit board (PCB)-based inductive sensor for detecting one or more metallic particles in the fluid, the PCB-based inductive sensor comprising: at least one printed circuit board (PCB) comprising: one or more layers comprising a field coil trace; and one or more layers comprising each of a first sense coil trace and a second sense coil trace, wherein the field coil trace is configured to generate a magnetic field when electrically driven and each of the first sense coil trace and the second sense coil trace are configured to detect a change in the magnetic field produced by the one or more metallic particles in the fluid.

Clause 78: A method for monitoring one or more properties of a fluid in a mechanical device, the method comprising: providing a printed circuit board (PCB)-based inductive sensor for detecting one or more metallic particles in the fluid, the PCB-based inductive sensor comprising: one or more printed circuit board (PCBs) comprising one or more layers forming at least one field coil trace and at least one sense coil trace, wherein the at least one field coil trace is configured to generate a magnetic field when electrically driven and the at least one sense coil is configured to detect a change in the magnetic field produced by the one or more metallic particles in the fluid.

The invention claimed is:

1. A system for monitoring one or more properties of a fluid in a mechanical device, the system comprising:

a printed circuit board (PCB)-based inductive sensor for detecting one or more metallic particles in the fluid, the PCB-based inductive sensor comprising:

a first PCB, a second PCB and a third PCB, the first PCB comprising a first field coil trace printed on one or more layers of the first PCB, the second PCB comprising a sense coil trace printed on one or more layers of the second PCB and the third PCB comprising a second field coil trace printed on one or more layers of the third PCB, and a mesh structure, wherein the first PCB, the second PCB and the third PCB comprise one or more apertures, the one or more apertures being aligned and allowing the fluid to pass through, wherein the first field coil trace, the sense coil trace and the second field coil trace are wound around each aperture, wherein the first field coil trace and the second field coil trace generate a magnetic field when electrically driven and the sense coil trace detects a change in the magnetic field produced by the one or more metallic particles in the fluid.

2. The system of claim 1, wherein the PCB-based inductive sensor further comprises at least one spacer component coupled to one or more of the first PCB, the second PCB and the third PCB, and wherein each spacer component is implemented in a substantially ring-shaped configuration with at least one aperture to allow the fluid to pass through.

3. The system of claim 2, further comprising an oil containment tube (OCT) for insertion into the corresponding one or more apertures to provide a sealed pathway for the fluid to pass through.

4. The system of claim 3, wherein each oil containment tube has a fluid conditioning curved opening.

5. The system of claim 1, wherein the PCB-based inductive sensor comprises a bypass channel formed in one or more of the first PCB, the second PCB and the third PCB to allow larger of the one or more metallic particles to pass through.

6. The system of claim 1, wherein the PCB-based inductive sensor further comprises a flow conditioner adjacent to one or more of the first PCB, the second PCB and the third PCB to guide the fluid to pass through the one or more apertures.

7. The system of claim 1, wherein the PCB-based inductive sensor comprises a plurality of coil triplets, each coil triplet comprising the first field coil trace of the first PCB, the sense coil trace of the second PCB and the second field coil trace of the third PCB, and wherein the plurality of coil triplets are coupled in a parallel configuration such that each coil triplet functions as an independent sensing element.

8. The system of claim 1, wherein the PCB-based inductive sensor comprises a plurality of first PCBs, a plurality of second PCBs and a plurality of third PCBs, and wherein the first field coil traces of the plurality of first PCBs are connected in series, the sense coil traces of the plurality of second PCBs are connected in series and the second field coil traces of the plurality of third PCBs are connected in series.

9. The system of claim 1, wherein the first field coil trace and the second field coil trace are configured to generate magnetic fields of opposite polarity, and wherein when the one or more metallic particles interact with the sense coil trace, a double-lobed voltage signal is generated.

10. The system of claim 1, wherein the PCB-based inductive sensor comprises one or more Faraday shield traces printed on one or more layers of at least one of the first PCB, the second PCB and the third PCB to attenuate electromagnetic interference.

11. The system of claim 1, wherein the fluid comprises a lubricant oil.

12. The system of claim 1, wherein the fluid comprises a fuel.

13. The system of claim 1, wherein the fluid comprises a transmission oil.

14. The system of claim 1, further comprising a probe, wherein the printed circuit board (PCB)-based inductive sensor is housed in the probe.

15. The system of claim 14, wherein at least a portion of the probe is insertable into the fluid.

16. The system of claim 1, wherein the PCB-based inductive sensor comprises a hydrodynamic profile to reduce pressure drop in the fluid flowing through the PCB-based inductive sensor.

17. The system of claim 1, wherein the PCB-based inductive sensor comprises one or more auxiliary sensors, the auxiliary sensors being hermetically sealed to one or more of the first PCB, the second PCB and the third PCB.

18. The system of claim 1, wherein the first PCB, the second PCB and the third PCB are fabricated from a chemically inert material configured to tolerate exposure to the fluid.

19. The system of claim 1, wherein the fluid comprises a hydraulic oil.

* * * * *